United States Patent [19]

Sato et al.

[11] Patent Number: 4,963,582
[45] Date of Patent: Oct. 16, 1990

[54] MACROLIDE COMPOUNDS, THEIR PREPARATION AND THEIR USE

[75] Inventors: Kazuo Sato; Toshiaki Yanai; Takao Kinoto; Keiji Tanaka; Akira Nishida, all of Shiga; Toshimitsu Toyama, Tokyo, all of Japan; Bruno Frei, Duebendorf; Anthony O'Sullivan, Basel, both of Switzerland

[73] Assignee: Sankyo Company Limited, Tokyo, Japan

[21] Appl. No.: 30,217

[22] Filed: Mar. 24, 1987

[30] Foreign Application Priority Data

Mar. 25, 1986 [JP] Japan .................................. 61-66315
Jun. 13, 1986 [JP] Japan ................................. 61-137568

[51] Int. Cl.$^5$ .................... A61K 31/365; C07D 493/22
[52] U.S. Cl. ...................................... 514/450; 549/264
[58] Field of Search ......................... 549/264; 514/450

[56] References Cited

U.S. PATENT DOCUMENTS

| 4,093,629 | 6/1978 | Fisher | 548/407 |
| 4,201,861 | 5/1980 | Mrozik et al. | 549/264 |
| 4,423,209 | 12/1983 | Mrozik | 549/264 |
| 4,547,520 | 10/1985 | Ide et al. | 549/264 |

FOREIGN PATENT DOCUMENTS

| 0001689 | 5/1979 | European Pat. Off. | 549/264 |
| 0184308 | 11/1986 | European Pat. Off. | |
| 0203832 | 12/1986 | European Pat. Off. | |
| 2168345 | 7/1986 | United Kingdom | 549/264 |

Primary Examiner—Glennon H. Hollrah
Assistant Examiner—Mark W. Russell
Attorney, Agent, or Firm—Frishauf, Holtz, Goodman & Woodward

[57] ABSTRACT

Compounds having a 16-membered macrolide ring, and related to the milbemycins and avermectins, with substituents at positions 5, 13, 25 and optionally also 23, have acaricidal, insecticidal and anthelmintic properties. They are useful for treating various pests in plants and animals.

12 Claims, No Drawings

MACROLIDE COMPOUNDS, THEIR PREPARATION AND THEIR USE BACKGROUND OF THE INVENTION

The present invention is concerned with a series of new macrolide compounds which are chemically related to certain known classes of macrolides including the milbemycins and avermectins. These compounds have valuable acaricidal, insecticidal and anthelmintic activities. The invention also provides methods of preparing these compounds and compositions and methods for using them.

There are several classes of known compounds with a structure based on a 16-membered macrolide ring, which are obtained by fermentation of various microorganisms or semi-synthetically by chemical derivatization of such natural fermentation products, and which exhibit acaricidal, insecticidal, anthelmintic and antiparasitic activities. The milbemycins and avermectins are examples of two such classes of known compounds, but various others also exist and are identified by different names or code numbers. The names for these various macrolide compounds have generally been taken from the names or code numbers of the microorganisms which produce the naturally occurring members of each class, and these names have then been extended to cover the chemical derivatives of the same class, with the result that there has been no standardized systematic nomenclature for such compounds generally.

In order to avoid confusion. a standardized system of nomenclature will be used herein, which follows the normal rules for naming derivatives of organic compounds and which is based on the hypothetical parent compound hereby defined as "milbemycin" represented by formula (A):

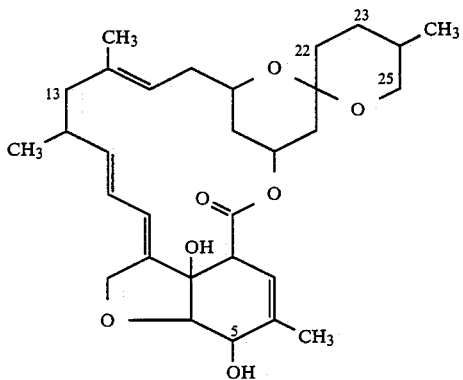

For the avoidance of doubt, formula (A) also shows the numbering of positions of the macrolide ring system applied to those positions most relevant to the compounds of the present invention.

The naturally produced milbemycins are a series of macrolide compounds known to have anthelmintic, acaricidal and insecticidal activities. Milbemycin D was disclosed in U.S. Pat. No. 4,346,171, where it was referred to as "Compound B-41D", and milbemycins $A_3$ and $A_4$ were disclosed in U.S. Pat. No. 3,950,360. These compounds may be represented by the above formula (A) in which position 25 is substitured with a methyl group, an ethyl group or an isopropyl group, these compounds being designated as milbemycin $A_3$, milbemycin $A_4$ and milbemycin D, respectively. The milbemycin analogue substituted at position 25 with a sec-butyl was disclosed in U.S. Pat. No. 4,173,571.

Subsequently, various derivatives of the original milbemycins have been prepared and their activities investigated. For example, epoxy milbemycins have been disclosed in Japanese Patent Application Kokai (i.e. laid open to public inspection) Nos. 57-139079, 57-139080, 59-33288 and 59-36681 and in U.S. Pat. No. 4,530,921. 5-Esterified milbemycins have been disclosed in U.S. Pat. Nos. 4,201,861, 4,206,205, 4,173,571, 4,171,314, 4,203,976, 4,289,760, 4,457,920, 4,579,864 and 4,547,491, in European Patent Publications Nos. 8184, 102,721, 115,930, 180,539 and 184,989 and in Japanese Patent Application Kokai Nos. 57-120589 and 59-16894.

13-Hydroxy-5-ketomilbemycin derivatives have been disclosed in U.S. Pat. No. 4,423,209. Milbemycin 5-oxime derivatives were disclosed in U.S. Pat. No. 4,547,520 and European Patent Publication No. 203 832.

Milbemycin derivatives esterified at position 13 are of particular relevance to the present invention and have been disclosed in U.S. Pat. No. 4,093,629 and European Patent Publication No. 186403, as well as in published British Patent Application No. 2,168,345 which discloses milbemycin derivatives having a carboxy or esterified carboxy substituent at position 13 in combination with a hydroxy or esterified hydroxy substituent at position 5.

Like the milbemycins, the avermectins are based upon the same 16-membered ring macrolide compound. The avermectins are disclosed, for example in J. Antimicrob. Agents Chemother., 15(3), 361–367 (1979). These compounds may be represented by the above formula (A) but with a carbon-carbon double bond at positions 22 and 23, and having position 13 substituted with a 4'-(α-L-oleandrosyl)-α-L-oleandrosyloxy group. Position 25 may be substituted with an isopropyl group or a sec-butyl group these compounds being designated as avermectin $B_{1b}$ and avermectin $B_{1a}$, respectively. 22,23-Dihydroavermectins $B_{1a}$ and $B_{1b}$ may be obtained by reduction of the double bond between the 22 and 23 positions and are disclosed in U.S. Pat. No. 4,199,569. The aglycone derivatives of the avermectins, which are milbemycin analogues, have sometimes been referred to in the literature as C-076 compounds, and various derivatives of these are known. For example, U.S. Pat. No. 4,201,861 discloses such derivatives substituted with a lower alkanoyl group at position 13.

Published European Patent Application No. 170006 discloses a family of bioactive compounds produced by fermentation, identified collectively by the code number LL-F28249. Some of these have a 16-membered macrolide structure corresponding to the above formula (A), substituted with hydroxy at position 23 and with 1-methyl-1-propenyl, 1-methyl-1-butenyl or 1,3-dimethyl-1-butenyl at position 25. In these compounds, the hydroxy at position 5 may also be replaced by methoxy.

Published British Patent Application No. 2,176,182 discloses another group of macrolide antibiotics corresponding to the above formula (A) with a hydroxy or substituted hydroxy group at position 5, a hydroxy substituted hydroxy or keto group at position 23, and an α-branched alkenyl group at position 25.

A yet further group of related macrolide derivatives is disclosed in Japanese Patent Application Kokai No. 62-29590. These have a structure corresponding to the above formula (A), with a hydroxy or methoxy group at position 5. position 13 of the ring can be substituted with a 4'-(α-L-oleandrosyl)-α-L-oleandrosyloxy group, as in the avermectins, and there may be a carbon-carbon double bond between positions 22 and 23, or alternatively position 23 may be substituted with hydroxy. The substituent at position 25 is of a type not found in the naturally produced avermectins and milbemycins, and includes various α-branched alkyl, alkenyl, alkynyl, alkoxyalkyl, alkylthioalkyl and cycloalkylalkyl groups, or cycloalkyl, cycloalkenyl or heterocyclic groups. This 25-substituent is introduced by adding the corresponding carboxylic acid or derivative thereof to the fermentation broth of an avermectin-producing microorganism.

SUMMARY OF THE INVENTION

The various classes of milbemycin-related macrolide compounds described above are all disclosed as having one or more types of activity as antibiotic, anthelmintic, ectoparasiticidal, acaricidal or other pesticidal agents. However there is still a continuing need to provide such agents with improved activity against one or more classes of pests.

It has now been discovered that the activity of such milbemycin-related derivatives can be improved by appropriately selecting the combination of substituents on the macrolide ring system, especially the substituents at positions 5 and 13. In particular, it has now been found that the activity of the 13-esterified derivatives in the above-mentioned prior art can be improved upon by appropriate selection of certain ester groups at this position, as specified below.

Accordingly, it is an object of the present invention to provide such macrolide compounds having improved activity. It is another object of the invention to provide methods for preparing such compounds. It is a still further object of the invention to provide pesticidal compositions and methods containing the said compounds.

In accordance with these objects, the invention provides compounds having the formula

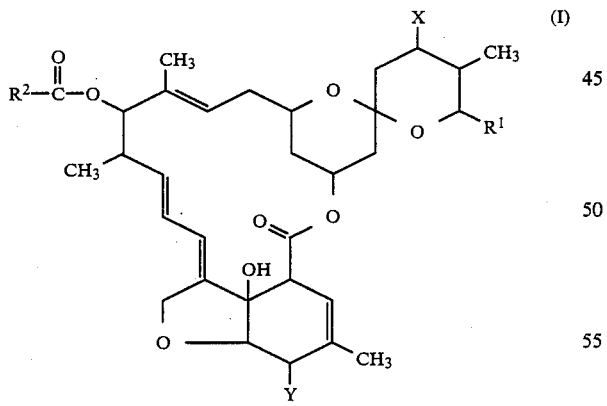

in which:
the broken line represents a carbon-carbon single or double bond between the atoms at the 22 and 23 positions;
X represents a hydrogen atom or a hydroxyl group, or together with the carbon atom to which it is attached represents the group C=O; provided that X represents a hydrogen atom when the broken line represents a double bond between the carbon atoms at the 22 and 23 positions;

Y represents the group =N—OR$^3$, or the group —OR$^4$, wherein R$^3$ represents a hydrogen atom, an alkyl group having from 1 to 6 carbon atoms and which may optionally be substituted with at least one carboxy group, a cycloalkyl group having from 3 to 10 ring carbon atoms, or an aralkyl group having from 6 to 10 ring carbon atoms in the aryl moiety and from 1 to 6 carbon atoms in the alkyl moiety; and R$^4$ represents a hydrogen atom, or an ester-forming carboxylic or carbonic acid residue;

R$^1$ represents an alkyl, alkenyl, alkynyl, alkoxyalkyl or alkylthioalkyl group, each having up to 8 carbon atoms; a cycloalkyl-substituted alkyl group wherein the cycloalkyl moiety has from 3 to 6 ring carbon atoms and the alkyl moiety has from 1 to 5 carbon atoms; a cycloalkyl or cycloalkenyl group having from 3 to 8 ring carbon atoms and optionally substituted with at least one substituent selected from halogen atoms and alkyl groups having from 1 to 4 carbon atoms; a heterocyclic group having from 3 to 6 ring atoms of which at least one is an oxygen or sulfur atom and which may optionally be substituted with at least one substituent selected from halogen atoms and alkyl groups having from 1 to 4 carbon atoms;

R$^2$ represents the group R$^5$—(O)$_n$— (when Y represents said group =N—OR$^3$) or the group A—(W-)$_n$—C(R$^6$R$^7$)— (when Y represents said group —OR$^4$) wherein n=0 or 1;

R$^5$ represents a hydrogen atom, an alkyl group having from 1 to 22 carbon atoms an alkenyl or alkynyl group having from 2 to 6 carbon atoms, a cycloalkyl group having from 3 to 10 carbon atoms, an aryl group having from 6 to 10 ring carbon atoms, an aralkyl group having from 6 to 10 ring carbon atoms in the aryl moiety and from 1 to 6 carbon atoms in the alkyl moiety, or a heterocyclic group having from 4 to 14 ring carbon atoms of which at least one is an oxygen, sulfur or nitrogen atom; wherein said alkyl group of R$^5$ may optionally be substituted with at least one substituent selected from:
(a) cycloalkyl groups having from 3 to 10 carbon atoms; alkoxy groups having from 1 to 6 carbon atoms; alkoxycarbonyl groups having from 2 to 7 carbon atoms; halogen atoms; aryloxy and arylthio groups having from 6 to 10 ring carbon atoms, which may themselves optionally be substituted with at least one halogen atom; protected or unprotected hydroxy, carboxy; amino; monoalkylamino and dialkylamino groups having from 1 to 6 carbon atoms in the or each alkyl moiety; aliphatic acylamino groups having from 1 to 6 carbon atoms; aromatic acylamino groups; cyano; carbamoyl; monoalkylcarbamoyl and dialkylcarbamoyl groups having from 1 to 6 carbon atoms in the or each alkyl moiety; mercapto; alkylthio, alkylsulfinyl and alkylsulfonyl groups, in each case having from 1 to 6 carbon atoms; nitro; and heterocyclic groups having from 4 to 14 ring carbon atoms of which at least one is an oxygen, sulfur or nitrogen atom;
and wherein said alkenyl and alkynyl groups of R$^5$ may optionally be substituted with at least one substituent selected from the group consisting of:
(b) the said substituents (a); and aryl groups having from 6 to 10 ring carbon atoms;

and wherein the said cycloalkyl, aryl, aralkyl and heterocyclic groups of $R^5$ may optionally be substituted with at least one substituent selected from:
(c) the said substituents (a); alkyl groups having from 1 to 6 carbon atoms each in the alkoxy and alkyl moieties; haloalkyl groups having from 1 to 6 carbon atoms; and haloalkenyl groups having from 2 to 6 carbon atoms;

$R^6$ represents an alkyl group having from 1 to 6 carbon atoms, a haloalkyl group having from 1 to 4 carbon atoms, an alkoxy group having from 1 to 4 carbon atoms an alkoxyalkyl group having from 1 to 4 carbon atoms, a phenyl group, or a cyano group;

$R^7$ represents a hydrogen atom or an alkyl group having from 1 to 4 carbon atoms;

or $R^6$ and $R^7$, together with the carbon atom to which they are attached, jointly represent a cyoloalkyl group having from 3 to 6 ring carbon atoms;

W represents a methylene group, or an oxygen or sulfur atom; and

A represents a phenyl group, a naphthyl group, or a heterocyclic group having from 5 to 10 ring atoms of which at least one is a nitrogen, oxygen or sulfur atom; and said phenyl, naphthyl or heterocyclic group may optionally be substituted with at least one substituent selected from alkyl, alkoxy and alkylthio groups each having from 1 to 4 carbon atoms, halogen atoms, trifluoromethyl, amino, nitro, cyano, keto, phenoxy (which may itself optionally be substituted with at least one substituent selected from halogen atoms and trifluoromethyl), and heterocyclyloxy groups having from 5 to 10 ring atoms of which at least one is a nitrogen, oxygen or sulfur atom;

and salts and esters of said compounds of formula (I).

The invention still further provides an anthelmintic, acaricidal and insecticidal composition comprising an anthelmintic, acaricidal and insecticidal compound in admixture with a pharmaceutically, agriculturally, veterinarily or horticulturally acceptable carrier or diluent, wherein said compound is selected from the group consisting of compounds of formula (I).

The invention still further provides the use for the manufacture of a medicament for treating an animal which may be human or non-human, parasitized by a parasite selected from helminths acarids and insects of at least one compound of formula (I).

The invention still further provides a method of protecting animals or plants from damage by parasites selected from acarids, helminths and insects, which comprises applying an active compound to said animals, to said plants or to seeds of said plants or to a locus including said animals plants or seeds, wherein the active compound is at least one compound of formula (I).

DETAILED DESCRIPTION OF THE INVENTION

In the compounds of formula (I), where $R^1$ represents an alkyl group having from 1 to 8 carbon atoms, this may be straight or branched chain alkyl group and examples of such groups include the methyl, ethyl, propyl, isopropyl, butyl, isobutyl, sec-butyl, t-butyl, pentyl, isopentyl, heptyl and octyl groups. According to one preferred embodiment of the invention, this alkyl group may be methyl ethyl isopropyl or sec-butyl. In accordance with another embodiment of the invention, the α-branched alkyl groups having from 3 to 8 carbon atoms are preferred.

Where $R^1$ represents an alkenyl group, this may be a straight or branched chain group containing from 2 to 8 carbon atoms and having at least one double bond, for example vinyl, 1-propenyl, 2-propenyl, isopropenyl, 1-methyl-1-propenyl, 1-methyl-1-butenyl and 1,3-dimethyl-1-butenyl. The α-branched alkenyl groups are particularly preferred.

Where $R^1$ represents an alkynyl group having from 2 to 8 carbon atoms, this may be a straight or branched chain group, for example ethynyl, 1-propynyl or 2-propynyl.

Where $R^1$ represents an alkoxyalkyl group or alkylthioalkyl group, this may have a total of from 2 to 8 carbon atoms and may be straight or branched, for example merhoxymethyl, ethoxymethyl, 1-methoxyethyl, 2-methoxyethyl, 2-ethoxyethyl, isopropoxymethyl, and the thio analogues of each of these groups. The methoxymethyl, 1-methoxyethyl, methylthiomethyl and 1-(methylthio)ethyl groups, respectively, are preferred.

Where $R^1$ represents a cycloalkyl or cycloalkenyl group, this may have a monocyclic or fused polycyclic (preferably bicyclic) ring system containing from 3 to 8 ring carbon atoms. Examples include the cyclopropyl, cyclobutyl, cyclopentyl, cyclohexyl, cycloheptyl, cyclooctyl, bicyclo[2.2.1]heptyl and norbornarnyl groups and the analogues thereof containing one or more double bonds. It should be understood that this definition also includes partly aromatic fused polycyclic ring systems for example the tetrahydronaphthyl and trimethylenephenyl groups.

Where $R^1$ represents a cycloalkyl-substituted alkyl group, the cycloalkyl moiety thereof may be any of the above-mentioned cycloalkyl groups which have from 3 to 6 ring carbon atoms and the alkyl moiety may be any of the above-mentioned straight or branched chain alkyl groups which have from 1 to 5 carbon atoms.

Where $R^1$ represents a heterocyclic group, this may have from 3 to 6 ring atoms, of which at least one is an oxygen or sulfur hetero-atom. The ring system may be unsaturated, or partly or wholly saturated. Examples of such heterocyclic groups include the oxiranyl, oxetanyl, thiranyl, thietanyl, (2,2-dimethyl)-1,3-dioxoranyl, furyl, thienyl, thiazolyl, isothiazolyl, oxazolyl, isoxazolyl and pyranyl groups.

Where $R^1$ represents a cycloalkyl, cycloalkenyl or heterocyclic group, this may optionally be substituted with at least one halogen atom (e.g. fluorine, chlorine, bromine or iodine) and/or at least one alkyl group having from 1 to 4 carbon atoms (e.g. any of those straight or branched chain alkyl groups mentioned above which have up to 4 carbon atoms).

The most preferred groups for $R^1$ are methyl, ethyl, isopropyl, sec-butyl, 1-methyl-1-propenyl, 1-methyl-1-butenyl and 1,3-dimethyl-1-butenyl.

In the above formula (I), where $R^3$ represents an alkyl group having from 1 to 6 carbon atoms, this may have a straight or branched chain and may be for example any of those alkyl groups mentioned above for $R^1$ and having up to 6 carbon atoms. The alkyl group $R^3$ may also optionally be substituted with one or more carboxy groups.

Where $R^3$ represents a cycloalkyl group having from 3 to 10 ring carbon atoms, this may have a monocyclic or fused polycyclic (preferably bicyclic) ring system and examples include those cycloalkyl groups mentioned above for $R^1$ as well as the cyclononyl, cyclodecyl and adamantyl groups.

Where R³ represents an aralkyl group, it may have from 6 to 10 ring carbon atoms in the aryl moiety and from 1 to 6 carbon atoms in the alkyl moiety. The alkyl moiety may have a straight or branched chain and may be, for example, any of those alkyl groups having up to 6 carbon atoms mentioned above for R¹. The aralkyl group preferably has from 7 to 12 carbon atoms in total, and examples include benzyl, α-methylbenzyl, α,α-dimethylbenzyl, phenethyl, phenylpropyl, naphthylmethyl and naphthylethyl.

The compounds of formula (I) where R³ is a hydrogen atom are oximes and can therefore form ester derivatives. The biological activity of the compounds of the invention arises from the structure shown in formula (I) and is not essentially dependent on the nature of any ester group, so there is no particular restriction on the acids which may be chosen to form such esters, provided that the activity of the resulting compound remains acceptable. Examples include carboxylic acid esters, carbamic acid esters, carbonic acid esters, sulfonic acid esters and phosphoric acid esters.

Such oxime esters are preferably compounds having the following formula (X):

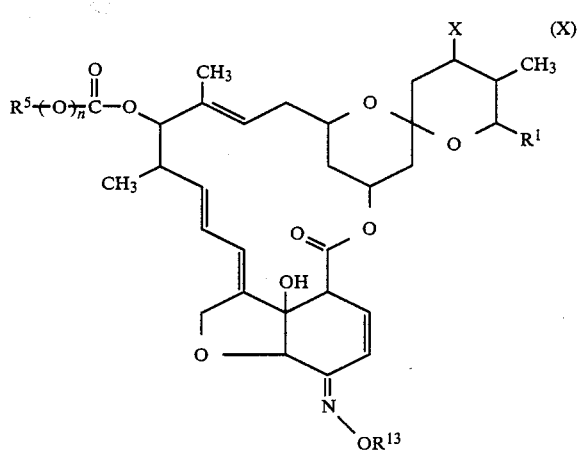

where R¹, R⁵, and n have the meanings previously defined and R¹³ represents one of the following groups (a)–(e):

(a) the group —COR¹⁴, wherein R¹⁴ represents an alkyl group which may optionally be substituted, a cycloalkyl group an aralkyl group which may optionally be substituted on its aryl ring or an aryl group which may optionally be substituted on its ring;

(b) the group —CQ—NR¹⁵R¹⁶ wherein Q represents an oxygen atom or a sulfur atom; and R¹⁵ and R¹⁶ may be the same or different and each represents a hydrogen atom, an alkyl alkenyl or alkynyl group in each case having up to 6 carbon atoms, or an aryl group which may optionally be substituted on its ring;

(c) the group —CQ—QR¹⁷, wherein Q is as previously defined; and R¹⁷ represents an alkyl group having from 1 to 6 carbon atoms, an aralkyl group which may optionally be substituted on its ring an aryl group which may optionally be substituted on its ring or a carboxy-protecting group capable of being hydrolyzed in vivo;

(d) the group —SO₂R¹⁸, wherein R¹⁸ represents an alkyl group having from 1 to 6 carbon atoms or an aryl group which may optionally be substituted on its ring; or (e) the group —PQ—(OR¹⁹)(OR²⁰), wherein Q is as previously defined; and R¹⁹ and R²⁰ may be the same or different and each represents an alkyl group having from 1 to 6 carbon atoms.

Where R¹⁴ or R¹⁷ represents an aralkyl group substituted on its aryl ring the substituent or substituents may suitably be selected from $C_{1-6}$ alkyl, halogen atoms, and the nitro group. Preferred aralkyl groups include alkyl-substituted benzyl groups having from 1 to 6 carbon atoms in the alkyl moiety, such as 3-or 4-methylbenzyl; halogenated benzyl groups, such as 4-chlorobenzyl, 4-bromobenzyl and 4-fluorobenzyl; and the 4-nitrobenzyl group.

Where any of R¹⁴ to R¹⁸ represents an aryl group substituted on its ring, the substituent or subtituents may be selected from alkyl groups having from 1 to 6 carbon atoms, halogen atoms, nitro, carboxyl, and alkoxycarbonyl groups having from 2 to 7 carbon atoms. Preferred aryl groups include alkyl-substituted phenyl groups having from 1 to 6 carbon atoms in the alkyl moiety, such as 2-tolyl, 3-tolyl, 4-tolyl or 2,4,6-trimethylphenyl; halogenated phenyl groups, such as 2-chlorophenyl, 3-chlorophenyl, 4-chlorophenyl, 2-bromophenyl, 3-bromophenyl or 4-bromophenyl; nitrophenyl groups, such as 4-nitrophenyl; carboxyphenyl groups, such as 2-carboxyphenyl, 3-carboxyphenyl or 4-carboxyphenyl; and alkoxycarbonylphenyl groups such as 2-methoxycarbonylphenyl, 3-methoxycarbonylphenyl, 4-methoxycarbonylphenyl, 2-ethoxycarbonylphenyl, 3-ethoxycarbonylphenyl or 4-ethoxycarbonylphenyl.

Where R¹⁵ or R¹⁶ represents an alkenyl or alkynyl group, this is preferably vinyl alyl, 1-propynyl, 2-propynyl or isopropenyl.

Where R¹⁷ is a carboxy-protecting group capable of being hydrolyzed in vivo, this may be for example an aliphatic acyloxymethyl group, such as acetoxymethyl, propionyloxymethyl, butyryloxymethyl or pivaloyloxymethyl; a 1-(alkoxycarbonyloxy)ethyl group with a $C_{1-6}$ alkoxy moiety, such as 1-methoxycarbonyloxyethyl, 1-ethoxycarbonyloxyethyl, 1-propoxycarbonyloxyethyl, 1-isopropoxycarbonyloxyethyl, 1-butoxycarbonyloxyethyl or 1-isobutoxycarbonyloxyethyl; a phthalidyl group; a (2-oxo-5-methyl-1,3-dioxolanyl-4-yl)methyl group; a (2,2-dimethyl-1,3-dioxolan-4-yl)methyl group or a (3,4-dihydropyran-2-carbonyloxy)methyl group. The (2,2-dimethyl-1,3-dioxolan-4-yl)methyl and (3,4-dihydropyran-2-carbonyloxy)methyl groups are preferred.

A preferred group of compounds of formula (I) are those wherein R³ represents hydrogen, $C_{1-6}$ alkanoyl, $C_{1-6}$ haloalkanoyl or di($C_{1-6}$ alkyl)carbamoyl. Of these compounds, the more preferred ones are those in which R³ is hydrogen and the $C_{1-6}$ alkanoyl esters; and the most highly preferred are those in which R³ is hydrogen, and the propionyl and pivaloyl esters.

In the compounds of formula (I) where Y represents the group —OR⁴, R⁴ may represent a hydrogen atom, so that the substituent at position 5 is a hydroxy group. As will readily be appreciated by those skilled in the art, this hydroxy group can form esters with a wide variety of carboxylic and carbonic acids, without significantly adversely affecting the biological activity of the compound which is derived from the 5-hydroxy substituent. Accordingly, the invention also embraces such esters where $R^4$ represents an ester-forming carboxylic or carbonic acid residue.

Preferred compounds are those in which $R^4$ is the hydrogen atom or a group of the following formula:

—CO—(O)$_n$—R$^8$ wherein n=0 or 1; and $R^8$ represents a straight or branched chain $C_{1-18}$ alkyl group, a $C_{3-7}$ cycloalkyl group, a $C_{7-9}$ aralkyl group, a $C_{2-6}$ alkenyl or alkynyl group, a $C_{6-10}$ aryl group or a monocyclic or fused heterocyclic group having from 5 to 10 ring atoms and containing at least one oxygen, sulfur or nitrogen atom. The group $R^8$ may optionally have one or more substituents, such as for example alkyl, alkoxy, alkoxyalkyl, halogen, haloalkyl, alkoxycarbonyl, acyloxy, hydroxy, carboxy, amino, mono- to trialkyl-amino, acylamino, cyano, carbamoyl, mono- or di-alkyl-carbamoyl, mercapto, alkylthio, alkylsulfinyl, alkylsulfonyl, nitro, phenoxy, halophenoxy, alkylsulfonyloxy, arylsulfonyloxy, cyanothio, and 5- or 6-membered heterocyclic groups containing at least on oxygen, sulfur or nitrogen atom. Where the substituent contains a carbon atom or atoms, the number of the carbon atoms is from 1 to 9. Where R8 itself is an alkyl, alkenyl or alkynyl group, the above-described substituent cannot be an alkyl, alkoxyalkyl or haloalkyl group.

Where $R^8$ is a $C_{1-18}$ alkyl group, it may be, for example, methyl, ethyl, propyl, isopropyl, butyl, isobutyl, sec-butyl, t-butyl, pentyl, hexyl, heptyl, octyl, decyl, undecyl, dodecyl, pentadecyl, hexadecyl, cyclopropyl, cyclobutyl, cyclopentyl, cyclohexyl or bicyclo[2.2.1-]heptyl.

Where $R^8$ is a $C_{7-9}$ aralkyl group, it may be, for example, benzyl, phenethyl, phenylpropyl, α-methylbenzyl or α,α-dimethylbenzyl.

Where $R^8$ is a $C_{2-6}$ alkenyl or alkynyl group, it may be, for example, vinyl, propenyl, ethynyl or pynyl.

Where $R^8$ is a $C_{6-10}$ aryl group, it may be, for example, a phenyl or naphthyl group.

Where $R^8$ is a heterocyclic group, it may be, for example, furyl, thienyl, pyrrolyl, pyridyl, thiazolyl, isothiazolyl, oxazolyl, isoxazolyl, imidazolyl, pyrrazolyl, pyranyl, triazolyl, triazinyl, quinazolinyl, tetrahydrofuranyl, tetrahydrothienyl, pyrrolidinyl, thiazolidinyl, piperazyl, morpholinyl, thiomorpholinyl, tetrahydroquinolyl, quinuclidinyl or thienofuranyl.

Where $R^8$ is further substituted, such further substituents include, for example, methyl, ethyl, isopropyl, t-butyl, methoxy, ethoxy, isopropoxy, methoxymethyl, methoxycarbonyl, ethoxycarbonyl, chloromethyl, trichloromethyl, trifluoromethyl, 2-chloroethyl, fluorine, chlorine, bromine, iodine, hydroxy, carboxy, amino, methylamino, dimethylamino, diethylamino, diisopropylamino, (diethyl)methylamino, acetylamino, trifluoroacetylamino, cyano, carbamoyl, methylcarbamoyl, dimethylcarbamoyl, fluoroacetoxy, trichloroacetoxy, mercapto, methylthio, cyanothio, methylsulfinyl, methanesulfonyl, nitro, phenoxy, p-chlorophenoxy, the 5- or 6-membered heterocyclic heterocyclic groups set out above in the definitions of $R^8$, and the 2,2-dimethyl-1,3-dioxolanylmethoxy, 3,4-dihydro-2H- pyran-2-carbonyloxy and 3,4,5,6-diisopropylidene-D-galacturonyloxy groups.

Preferred compounds include those where $R^4$ represents hydrogen and the esters where $R^4$ represents the group —CO—R$^8$. In these esters, the group $R^8$ is preferably a ($C_{2-7}$ alkanoyl)oxymethyl group, a chloromethyl group, an iodomethyl group, a mono-, di- or trialkylaminomethyl group (and particularly a trialkylaminomethyl group, wherein the nitrogen is quarternized), a (heterocyclic amino)methyl group (such as 1-piperidylmethyl or 1-morpholinylmethyl), a 2-carboxyethyl or 3-carboxypropyl group, or the 2,2-dimethyl-1,3-dioxolan-4-ylmethoxy group. Compounds where $R^8$ is ($C_{2-7}$ alkanoyl)oxymethyl are particularly preferred. The most preferred values for $R^4$ are hydrogen, acetoxyacetyl and pivaloyloxyacetyl.

Where $R^2$ represents the group $R^5$—(O)$_n$— and $R^5$ represents an alkyl group, this may have a straight or branched chain with from 1 to 22 carbon atoms. Examples include methyl, ethyl, propyl, isopropyl, butyl, sec-butyl, isobutyl, t-butyl, pentyl, hexyl, heptyl, octyl, nonyl, decyl, 3-methylnonyl, 8-methylnonyl, 3-ethyloctyl, 3,7-dimethyloctyl, undecyl, dodecyl, tridecyl, tetradecyl, pentadecyl, hexadecyl, 1-methylpentadecyl, 14-methylpentadecyl, 13,13-dimethyltetradecyl, heptadecyl, 15-methylhexadecyl, octadecyl, 1-methylheptadecyl, nonadecyl, icosyl, henicosyl and docosyl. Alkyl groups having from 1 to 18 carbon atoms are preferred.

Where $R^5$ represents a cycloalkyl group, this may have a monocyclic or fused polycyclic (preferably bicyclic) ring system containing from 3 to 10 ring carbon atoms, and examples include those mentioned above for $R^3$.

Where $R^5$ represents an alkenyl or alkynyl group, this may have a straight or branched chain with from 2 to 6 carbon atoms and with one or more double or triple bonds, respectively. Examples include those already mentioned above for $R^1$ and having up to 6 carbon atoms.

Where $R^5$ represents an aryl group containing from 6 to 10 carbon atoms, examples of such groups include the phenyl, 1-naphthyl and 2-naphthyl groups. The phenyl group is preferred.

Where $R^5$ represents an aralkyl group, it may have from 6 to 10 ring carbon atoms in the aryl moiety and from 1 to 6 carbon atoms in the alkyl moiety, and it preferably has a total of from 7 to 12 carbon atoms. Examples include those already mentioned above for the aralkyl group of $R^3$.

Where $R^5$ represents a heterocyclic group, it contains from 4 to 14 ring atoms, of which at least one, and preferably from 1 to 3, are hetero-atoms selected from nitrogen oxygen and sulfur. The ring system may be monocyclic or fused polycyclic (preferably bicyclic), and may be unsarurated, or partly or completely saturated. Examples of such groups include oxiranyl, oxetanyl, aziridinyl, azetidinyl, thiranyl, thietanyl, (2,2-dimethyl)-1,3-dioxoranyl, furyl, thienyl, pyrrolyl, pyridyl, thiazolyl, isothiazolyl, oxazolyl, isoxazolyl, imidazolyl, pyrazolyl, pyranyl, pyrazinyl, pyridazinyl, pyrimidinyl, benzofuranyl, benzothiophenyl, indolyl, quinolyl, isoquinolyl, quinazolyl, quinoxalinyl, naphthyridinyl, xanthenyl, tetrahydrofuranyl, tetrahydrothienyl, pyrrolidinyl, thiazolidinyl, imidazolidinyl, imidazolinyl, oxazolinyl, oxazolidinyl, pyrazolidinyl, piperazyl, tetrahydropyrimidinyl, dihydropyridazinyl, morpholinyl, indolinyl and tetrahydroquinolyl. Preferred groups include oxiranyl, oxetanyl, aziridinyl, azetidinyl, furyl, thienyl, pyrrolyl, pyridyl, thiazolyl, oxazolyl, tetrahydrofuranyl, tetrahydrothienyl, pyrrolidinyl, morpholinyl, benzofuranyl, (2,2-dimethyl)-1,3-dioxoranyl and quinolyl.

The group $R^5$ may optionally carry one or more substituents, as set out in the definitions for formula (I). Where an alkyl group is present as a substituent, this may be any of the alkyl groups having from 1 to 6 carbon atoms mentioned above. Where there is an alkoxy substituent having from 1 to 6 carbon atoms, this may correspond to any of the said alkyl groups, for example methoxy or ethoxy. Where there is an alkoxycarbonyl substituent having from 2 to 7 carbon atoms, the alkoxy moiety of this may correspond to any of the said alkoxy groups, for example methoxycarbonyl, ethoxycarbonyl, propoxycarbonyl or t-butoxycarbonyl. Where the substituent is a halogen atom, it may be fluorine, chlorine, bromine or iodine. Where the substituent is an aryloxy or arylthio group, which may optionally itself be halogen-substituted, examples include phenoxy, phenylthio, chlorophenoxy, bromophenoxy, iodophenoxy, fluorophenoxy, dichlorophenoxy, chlorophenylthio and bromophenylthio groups.

Where $R^5$ is substituted with a protected hydroxy group, the hydroxy-protecting group may be any of those conventionally employed for this purpose. For example, the protecting group may be a tri-(lower)alkylsilyl group such as trimethylsilyl, triethylsilyl, isopropyldimethylsilyl, t-butyldimethylsilyl, merhyldiisopropylsilyl, methyldi-t-butylsilyl, or triisopropylsilyl; a lower aliphatic acyl group such as formyl, acetyl, chloroacetyl, dichloroacetyl, trichloroacetyl, trifluoroacetyl, methoxyacetyl, propionyl, n-butyryl, (E)-2-methyl-2-butenoyl, isobutyryl, penranoyl or pivaloyl; or an aromatic acyl group such as benzoyl, o-(dibromoethyl)-benzoyl, o-(merhoxycarbonyl)benzoyl, o-phenylbenzoyl, 2,4,6-trimethylbenzoyl, p-toluoyl, p-anisoyl, p-chlorobenzoyl, p-nitrobenzoyl, o-nitrobenzoyl or $\alpha$-naphthoyl. When the group protects two or more hydroxy groups simultaneously, it may be an alkylidene group such as isopropylidene.

Where the substituent on $R^5$ is a monoalkylamino or dialkylamino group, the or each alkyl moiety may be any of the alkyl groups having from 1 to 6 carbon atoms already mentioned above, and examples include methylamino, ethylamino, propylamino, isobutylamino, dimethylamino, diethylamino, methylethylamino and methylbutylamino groups. Where the substituent is an acylamino group, the acyl moiety may be aliphatic with from 1 to 6 carbon atoms, such as formyl, acetyl, propionyl, butyryl or hexanoyl, or it may be aromatic, such as benzoyl or naphthoyl; and the group is preferably an aliphatic acylamino group having from 2 to 4 carbon atoms, such as acetylamino, propionylamino or butyrylamino. Where the substituent is a monoalkylcarbamoyl or dialkylcarbamoyl group, the or each alkyl moiety may be any of the alkyl groups having from 1 to 6 carbon atoms already mentioned above, and examples include methylcarbamoyl, dimethylcarbamoyl and diethylcarbamoyl. Where there is a substituent on $R^5$ which is an alkylthio, alkylsulfinyl or alkylsulfonyl group having from 1 to 6 carbon atoms, the alkyl moiety thereof may be any of the alkyl groups already mentioned above having from 1 to 6 carbon atoms, and examples of these include, respectively, methylthio, ethylthio, propylthio, burylthio and sec-butylthio; methylsulfinyl and ethylsulfinyl; and methanesulfonyl and ethanesulfonyl.

Where $R^5$ has an alkoxyalkyl substituent, the alkoxy and alkyl moieties each having from 1 to 6 carbon atoms may be any of those already mentioned above, and each moiety preferably has from 1 to 4 carbon atoms, for example methoxymethyl, ethoxymethyl, propoxymethyl, 2-methoxyethyl, 2-ethoxyethyl, 2-butoxyethyl or 3-propoxypropyl. Where $R^5$ has as a substituent a haloalkyl group with from 1 to 6 carbon atoms or a haloalkenyl group with from 2 to 6 carbon atoms, this may correspond to any of the alkyl or alkenyl groups already mentioned above and preferably substituted with from 1 to 4 halogen atoms (selected from the halogen substituents already mentioned above), for example chloromethyl, bromomethyl, iodomethyl, fluoromethyl, dichloromethyl, trifluoromethyl, trichloromethyl, 2-chloroethyl, 2,3-dibromopropyl, 2,2,2-trichloroethyl, 1,2,2,2-tetrabromoethyl, 2,2-dibromovinyl or 2,2-dichlorovinyl.

Examples of preferred values for $R^5$ include the following: a hydrogen atom; an alkyl group having from 1 to 22 carbon atoms such as methyl ethyl isopropyl, t-butyl, pentyl, heptyl or pentadecyl; an optionally condensed cycloalkyl group having from 3 to 12 carbon atoms such as cyclopropyl, cyclobutyl, cyclohexyl, 1-methylcyclopropyl, 1-methylcyclohexyl or adamantyl; a halogenated alkyl group having from 1 to 6 carbon atoms such as trifluoromethyl, iodomethyl, chloromethyl, bromomethyl, trichloromethyl, tribromomethyl, 2-chloroethyl, fluoromethyl, 2-fluoroethyl, 2-bromoethyl, 1,1-dichloroethyl, 1,1-dimethyl-2-chloroethyl, 2,2,2-trichloroethyl, 2,2,2-tribromoethyl or 2,2,2-trifluoroethyl; an alkoxyalkyl group having from 1 to 4 carbon atoms each in the alkyl and alkoxy moieties such as methoxymethyl, ethoxymethyl, methoxyethyl or 2-methoxyethyl; an aryloxyalkyl group having from 1 to 6 carbon atoms in the alkyl moiety wherein the ring may optionally be halogenated such as phenoxymethyl or 4-fluorophenoxymethyl; an optionally protected hydroxyalkyl group having from 1 to 6 carbon atoms such as 2-hydroxyethyl, hydroxymethyl, 2,3-dihydroxypropyl, acetoxymethyl or pivaroyloxymethyl; a mercaptoalkyl group having from 1 to 6 carbon atoms such as 2-mercaptoethyl; an alkylthloalkyl group having from 1 to 4 carbon atoms in each of the alkyl moieties such as methylthiomethyl; a dialkylaminoalkyl group having from 1 to 4 carbon atoms in each of the alkyl moieties such as dimethylaminomethyl; an alkenyl-substituted cycloalkyl group such as 2-isobutenyl-3,3-dimethylcyclopropyl; a haloalkyl-substituted cycloalkyl group having from 1 to 4 carbon atoms in the haloalkyl moiety such as 2-(1,2,2,2-tetrabromoethyl)-3,3-dimethylcyclopropyl; a haloalkenyl-substituted cycloalkyl group such as 2-(2,2-dichlorovinyl)-3,3-dimethylcyclopropyl; a heterocyclylalkyl group having from 1 to 6 carbon atoms in the alkyl moiety such as 2-furfuryl, imidazolylmethyl, 4-pyridylmethyl, 2-thienylmethyl or 2,2-dimethyl-1,3-dioxoran-4-ylmethyl; a halogenated alkenyl group such as 2,2-dichlorovinyl; an alkenyl group having from 2 to 4 carbon atoms such as vinyl, 1-propenyl or 1-isobutenyl; an alkynyl group having from 2 to 4 carbon atoms such as 1-propynyl or ethynyl; an aralkyl group having from 7 to 9 carbon atoms such as benzyl, phenethyl, $\alpha$-methylbenzyl or $\alpha,\alpha$-dimethylbenzyl; an aryl group such as phenyl; a halogenated aryl group, in particular a halophenyl group such as 2-, 3-or 4-bromophenyl, 2-, 3- or 4-fluorophenyl, 2,4-dichlorophenyl, 2,5-dichloro-6-methoxyphenyl, 2,3,4,5,6-pentafluorophenyl or 2,6-difluorophenyl; an alkoxyaryl group, in particular an alkoxyphenyl group having from 1 to 4 carbon atoms in the alkoxy moiety, such as methoxyphenyl; a nitroaryl group, in particular a nitrophenyl group such as 4-nitrophenyl; an alkylaryl group, in particular an alkylphenyl group having from 1 to 4 carbon atoms in the alkyl moiety such as 2-, 3- or 4-tolyl or 4-t-butylphenyl; a haloalkyl-substituted aryl group, in particular a haloalkyl-substituted phenyl group having from 1 to 4 carbon atoms in the haloalkyl moiety, such as 2-, 3- or 4-trifluoromethylphenyl or 2,5-di(trifluoromethyl)phenyl; a hydroxy-substituted aryl group, in particular a hydroxy-substituted phenyl group which may optionally be protected, such as 1-acetoxyphenyl; and a 5- or 6-membered heterocyclic group containing one or two hetero atoms in its ring such as 2-oxetanyl, 2-azetidinyl, 2- or 3-furyl, 2- or 3-thienyl, 1-isoquinolyl or 2- or 4-pyridyl.

$R^5$ is more preferably an α-branched alkyl or haloalkyl group having from 4 to 7 carbon atoms; or a phenyl or benzyl group which may be substituted with one or two substituents selected from trifluoromethyl, halogen (particularly fluorine or chlorine), methyl and amino. Most preferably, $R^5$ is a 2,6-difluorophenyl, o-(trifluoromethyl)phenyl, α-methylbenzyl, α,α-dimethylbenzyl, tert-butyl and fluoro-tert-butyl group.

In the compounds of formula (I) where $R^2$ represents the group $A-(W)_n-C(R^6R^7)-$, where $R^6$ is a $C_{1-6}$ alkyl group, it may be a straight or branched chain alkyl group, for example, a methyl, ethyl, propyl, isopropyl, butyl, isobutyl or sec-butyl group, and it is preferably the methyl or ethyl group.

Where $R^6$ is a $C_{1-4}$ haloalkyl group, it is a straight or branched chain alkyl group subsituted by a halogen atom or atoms and it includes, for example, a chloromethyl, fluoromethyl, trifluoromethyl, bromomethyl, 2-chloroethyl or 3-fluoropropyl group, preferably the chloromethyl group.

Where $R^6$ is a $C_{1-4}$ alkoxyalkyl group, it is an alkyl group subsituted by one or more of straight or branched chain alkoxy groups and it includes, for example, the methoxymethyl, ethoxymethyl, 2-methoxyethyl, 2-ethoxyethyl and isopropoxymethyl groups, preferably the methoxymethyl group.

Where $R^6$ is a $C_{1-4}$ alkoxy group, it is a straight or branched chain alkoxy group and it includes, for example, the methoxy, ethoxy, propoxy, isopropoxy, butoxy, isobutoxy and sec-butoxy group, preferably the methoxy group.

Where $R^6$ is a $C_{1-4}$ alkylthio group, it may have a straight or branched alkyl chain, for example the methylthio, ethylthio, propylthio, isopropylthio and butylthio groups, preferably the methylthio group.

$R^6$ is more preferably $C_{1-3}$ alkyl (particularly methyl or ethyl), or phenyl, and most preferably methyl or ethyl.

Where $R^7$ is a $C_{1-4}$ alkyl group, it may be a straight or branched chain alkyl group and it includes, for example, the methyl, ethyl, propyl, isopropyl and butyl groups, preferably the methyl group.

Compounds in which $R^7$ is hydrogen or methyl are most preferred.

Where A is a heterocyclic group, it may be, for example, a furyl, thienyl, pyrrolyl, pyridyl, imidazolyl, pyridazinyl, benzofuranyl, benzothiophenyl, indolyl, quinolyl, quinazolinyl or quinoxalinyl group, preferably a furyl, thienyl, pyridinyl, benzothiophenyl or quinolyl group.

Where A is further substituted, such further substituents may be selected, for example, from methyl, ethyl, propyl, isopropyl, butyl, sec-butyl, methoxy, ethoxy, propoxy, isopropoxy, fluorine, chlorine, bromine, iodine, trifluoromethyl, nitro, cyano, phenoxy, p-chlorophenoxy, p-fluorophenoxy, o-chlorophenoxy, o-fluorophenoxy, p-trifluorophenoxy, o-trifluorophenoxy, 2-furyloxy, 2-thienyloxy, 2-pyrrolyloxy, 2-pyridyloxy, 3-pyridyloxy, 2-quinolyloxy, 2-benzoxazolyloxy, 2-quinoxalyloxy, 2-quinazolinyloxy, 2,4-dichlorophenoxy, 5-trifluoromethyl-2-pyridyloxy, 5-trifluoromethyl-3-chloro-2-pyridyloxy, 3-chloro-2-furyloxy, 3-chlorothienyl-2-thienyloxy, 2-chloro-5-pyridyloxy, 6-chloro-2-benzoxazolyloxy and 6-chloro-2-quinoxalinyloxy. Preferred substituents are methyl, methoxy, trifluoromethyl, chloro, fluoro, 2-chloro-6-pyridyloxy and 6-chloro-2-benzoxazolyoxy.

The preferred groups $A-(W)_n-$ are those in which $n=0$, such as phenyl, halophenyl (e.g. chlorophenyl, fluorophenyl, trifluorophenyl and dichlorophenyl), tolyl, methoxyphenyl, phenoxy, chlorophenoxy, benzyl and phenoxyphenyl. Phenyl and halophenyl groups are more highly preferred, and in particular phenyl.

The compounds of formula (I) include some in which a carboxyl group may be present in the substituent $R^2$ or Y. As will be readily understood, esters and salts of such compounds may be formed by conventional techniques, and such esters and salts are also included within the scope of the invention.

In particular, such salts include those with alkali metals such as lithium, sodium or potassium, alkaline earth metals such as calcium or barium, other metals such as magnesium or aluminium, and organic amines, particularly tertiary amines such as triethylamine and triethanolamine. The alkali metal salts are preferred, and particularly the sodium and potassium salts.

It will also be appreciated from formula (I) that the compounds of the invention are capable of existing in the form of various isomers. Thus, the substituent at position 13 of the macrolide ring may be in either the alpha or beta configuration. The compounds which have beta-configuration at position 13 are preferred, but the invention includes both sets of stereoisomers, as well as mixtures thereof. Equally, those compounds having an oxime group at position 5, i.e. where Y represents the group $=N-OR^3$, can exist in the form of syn- and anti-isomers; and the individual syn- and anti-isomers are included within the scope of the invention, as well as mixtures thereof.

The following Tables give examples of individual compounds in accordance with the present invention, the compounds being identified by means of the substituent groups shown in formula (I) above. In all the compounds of Tables 1(A)–(H), Y in formula (I) represents the group $=N-OR^3$; whereas in all the compounds of Tables 2(A)–(D), Y represents the group $-OR^4$.

TABLE 1(A)

In all of the following compounds 1–194, there is a single carbon-carbon double bond between the atoms at positions 22 and 23, X represents a hydrogen atom, $R^1$ represents an ethyl group, and $R^2$ and $R^3$ have the meanings shown.

| No. | $R^2$ | $R^3$ |
|---|---|---|
| 1 | t-butyl | acetyl |
| 2 | t-butyl | propionyl |
| 3 | t-butyl | dimethylcarbamoyl |
| 4 | trichloromethyl | tosyl |
| 5 | dimethylaminomethyl | hydrogen |
| 6 | methylthiomethyl | carboxymethyl |
| 7 | 1-imidazolylmethyl | hydrogen |
| 8 | 2,2,2-trichloroethoxy | diethoxyphosphoryl |
| 9 | 2,2,2-trichloroethoxy | 2,3-dihydro-4H-pyran-2-yl-carboxymethoxycarbonyl |

TABLE 1(A)-continued

| | | |
|---|---|---|
| 10 | 2-chloroethyl | hydrogen |
| 11 | 2-thienyl | hydrogen |
| 12 | 3-thienyl | methyl |
| 13 | 4-pyridyl | hydrogen |
| 14 | 1-isoquinolyl | propionyl |
| 15 | p-fluorophenoxymethyl | hydrogen |
| 16 | p-fluorophenoxymethyl | pivaloyl |
| 17 | ethoxy | hydrogen |
| 18 | methyl | hydrogen |
| 19 | methoxy | hydrogen |
| 20 | ethoxy | pivaloyl |
| 21 | methoxy | dimethylcarbamoyl |
| 22 | ethyl | acetyl |
| 23 | ethoxy | palmitoyl |
| 24 | t-butyl | diethoxythiophosphoryl |
| 25 | t-butyl | methylcarbamoyl |
| 26 | t-butyl | hydrogen |
| 27 | 2,2,2-trichloroethoxy | hydrogen |
| 28 | 2,2-dichloroethyl | hydrogen |
| 29 | trichloromethyl | hydrogen |
| 30 | iodomethyl | hydrogen |
| 31 | 2,2,2-trichloroethoxy | dimethylcarbamoyl |
| 32 | 2,2,2-trichloroethyl | dimethylcarbamoyl |
| 33 | 2-chloroethyl | tosyl |
| 34 | trichloromethyl | propionyl |
| 35 | 2,2,2-trichloroethoxy | propionyl |
| 36 | 2,2,2-trichloroethoxy | isobutyryl |
| 37 | 2,2,2-trichloroethoxy | acetyl |
| 38 | benzyloxy | hydrogen |
| 39 | benzyl | hydrogen |
| 40 | benzyloxy | carboxymethyl |
| 41 | benzyl | dimethylcarbamoyl |
| 42 | 2-methoxyethoxy | hydrogen |
| 43 | 2-methoxyethoxy | dimethylcarbamoyl |
| 44 | 2-hydroxy-3-(t-butyl-dimethylsiloxy)propoxy | hydrogen |
| 45 | (2,2-dimethyl-1,3-dioxolanyl)methoxy | hydrogen |
| 46 | (2,2-dimethyl-1,3-dioxolanyl)methoxy | dimethylcarbamoyl |
| 47 | 2,3-dihydroxypropoxy | hydrogen |
| 48 | 2,3-dihydroxypropyl | hydrogen |
| 49 | 2,3-dihydroxypropyl | propionyl |
| 50 | 1-propenyl | hydrogen |
| 51 | hydrogen | hydrogen |
| 52 | p-chlorophenyl | hydrogen |
| 53 | p-t-butylphenyl | hydrogen |
| 54 | p-t-butylphenyl | dimethylcarbamoyl |
| 55 | o-trifluoromethylphenyl | hydrogen |
| 56 | o-trifluoromethylphenyl | dimethylcarbamoyl |
| 57 | p-bromophenyl | hydrogen |
| 58 | p-bromophenyl | octanoyl |
| 59 | p-trifluoromethylphenyl | benzyl |
| 60 | p-trifluoromethylphenyl | methyl |
| 61 | 2-furyl | hydrogen |
| 62 | 2-furyl | dimethylcarbamoyl |
| 63 | p-bromophenyl | hydrogen |
| 64 | iodomethyl | propionyl |
| 65 | acetoxymethyl | hydrogen |
| 66 | acetoxymethyl | propionyl |
| 67 | pivaloyloxymethyl | hydrogen |
| 68 | hydroxymethyl | hydrogen |
| 69 | 2-(2,2-dimethylvinyl)-3,3-dimethylcyclopropyl | hydrogen |
| 70 | 2-(2,2-dibromovinyl)-3,3-dimethylcyclopropyl | propionyl |
| 71 | 2-(1,2,2,2-tetrabromoethyl)-3,3-dimethylcyclopropyl | dimethylcarbamoyl |
| 72 | 2,2,2-trifluoroethyl | diethylcarbamoyl |
| 73 | 2,2-difluoroethoxy | diisopropylcarbamoyl |
| 74 | 2-fluoroethoxy | methylcarbamoyl |
| 75 | trifluoromethyl | ethylcarbamoyl |
| 76 | difluoromethyl | isopropylcarbamoyl |
| 77 | fluoromethoxy | methylethylcarbamoyl |
| 78 | 2,2,2-tribromoethoxy | methylisopropyl-carbamoyl |
| 79 | 2,2-dibromoethyl | acetyl |
| 80 | 2-bromoethyl | trifluoroacetyl |
| 81 | 2,2-dichloroethoxy | butyryl |
| 82 | pentafluoroethoxy | valeryl |
| 83 | 2,2,2-trichloroethyl | 3,3,3-trifluoropropionyl |
| 84 | methoxymethyl | carboxymethyl |
| 85 | ethoxymethoxy | propionyl |
| 86 | 2-(2,2-dichlorovinyl)-3,3-dimethylcyclopropyl | dimethylcarbamoyl |
| 87 | 2-(2,2-dichlorovinyl)-3,3-dimethylcyclopropyloxy | propionyl |
| 88 | 2-(2,2-dichlorovinyl)-3,3-dimethylcyclopropyl | pentaacetylgluconyl |
| 89 | t-butyl | pentaacetylgluconyl |
| 90 | 2-chloro-1,1-dimethylethyl | hydrogen |
| 91 | 2,2-dichloro-1,1-dimethyl-ethyl | hydrogen |
| 92 | 1,1-bis(chloromethyl)ethyl | hydrogen |
| 93 | α,α-dimethylbenzyl | hydrogen |
| 94 | α-methylbenzyl | hydrogen |
| 95 | 1,1-dichloroethyl | hydrogen |
| 96 | cyclopropyl | hydrogen |
| 97 | 1-methylcyclopropyl | hydrogen |
| 98 | cyclobutyl | hydrogen |
| 99 | cyclohexyl | hydrogen |
| 100 | 1-methylcyclohexyl | hydrogen |
| 101 | 3-oxacyclobutyl | hydrogen |
| 102 | 2-fluoro-1,1-dimethylethyl | hydrogen |
| 103 | heptanyl | hydrogen |
| 104 | pentadecyl | hydrogen |
| 105 | o-chlorophenyl | hydrogen |
| 106 | 2,4-dichlorophenyl | hydrogen |
| 107 | o-fluorophenyl | hydrogen |
| 108 | 2,6-difluorophenyl | hydrogen |
| 109 | o-bromophenyl | hydrogen |
| 110 | m-trifluoromethylphenyl | hydrogen |
| 111 | p-trifluoromethylphenyl | hydrogen |
| 112 | 3,5-bis(trifluoromethyl)-phenyl | hydrogen |
| 113 | 2,5-dichloro-6-methoxy-phenyl | hydrogen |
| 114 | m-tolyl | hydrogen |
| 115 | pentafluorophenyl | hydrogen |
| 116 | 4-pyridyl | hydrogen |
| 117 | o-acetoxyphenyl | hydrogen |
| 118 | o-allyloxyphenyl | hydrogen |
| 119 | 2-benzofuranyl | hydrogen |
| 120 | 1-adamantyl | hydrogen |
| 121 | o-trifluoromethylphenyl | pentaacetylgluconyl |
| 122 | α-methylbenzyl | hydrogen |
| 123 | α,α-dimethylbenzyl | hydrogen |
| 124 | 2-(2,2-dichlorovinyl)-3,3-dimethylcyclopropyl | hydrogen |
| 125 | methoxymethyl | hydrogen |
| 126 | 1-methoxy-1-methylethyl | hydrogen |
| 127 | 2,2,2-trifluoroethyl | hydrogen |
| 128 | 1-chloro-2,2,2-trifluoroethyl | hydrogen |
| 129 | 1,2,2,2-tetrachloroethyl | hydrogen |
| 130 | trichlorovinyl | hydrogen |
| 131 | 1,1-dichloro-2,2,2-trifluoroethyl | hydrogen |
| 132 | 1-chloro-1-methylethyl | hydrogen |
| 133 | 1,1-dichloroethyl | hydrogen |
| 134 | t-pentyl | hydrogen |
| 135 | 1,1,2,2-tetramethylpropyl | hydrogen |
| 136 | neopentyl | hydrogen |
| 137 | chloromethyl | hydrogen |
| 138 | 2-fluoro-1,1-dimethylethyl | hydrogen |
| 139 | 1-methylcyclobutyl | hydrogen |
| 140 | 1-methylcyclopentyl | hydrogen |
| 141 | 3-methyl-3-oxacyclobutyl | hydrogen |
| 142 | 3-methylcyclohexyl | hydrogen |
| 143 | 3,4-dimethylcyclohexyl | hydrogen |
| 144 | 4-t-butylcyclohexyloxy | hydrogen |
| 145 | cycloheptyl | hydrogen |
| 146 | 1,3-pentadienyl | hydrogen |
| 147 | 2,2-dichloro-3,3,3-trifluoropropoxy | hydrogen |
| 148 | 1-ethylvinyl | hydrogen |
| 149 | 1-propylbutyl | hydrogen |
| 150 | 1,1-difluoro-3-butenyl | hydrogen |
| 151 | 1-methyl-1-methylthioethyl | hydrogen |
| 152 | p-nitrophenyl | hydrogen |
| 153 | p-aminophenyl | hydrogen |
| 154 | o-phenoxyphenyl | hydrogen |
| 155 | 2-m-xylyl | hydrogen |

TABLE 1(A)-continued

| No. | R¹ | R² |
|---|---|---|
| 156 | 4-mesityl | hydrogen |
| 157 | m-phenoxyphenyl | hydrogen |
| 158 | 2,5,7,8-tetramethyl-6-methoxy-2-chromanyl | hydrogen |
| 159 | 9-fluorenyl | hydrogen |
| 160 | 2,3-dihydro-3-oxopyrido-[2,1-c]-1,2,4-triazol-2-yl | hydrogen |
| 161 | 9-xanthenyl | hydrogen |
| 162 | 3-chloro-2-benzothienyl | hydrogen |
| 163 | 2,6-dichloro-4-pyridyl | hydrogen |
| 164 | 3-methyl-3-oxacyclobutyl | hydrogen |
| 165 | 2-ethylthio-3-pyridyl | hydrogen |
| 166 | phenethyl | hydrogen |
| 167 | cyclohexylmethyl | hydrogen |
| 168 | 1-[(p-phenoxy)phenoxy]ethyl | hydrogen |
| 169 | 1-[(5-trifluoromethylpyrid-2-yl)oxyphenoxy]ethyl | hydrogen |
| 170 | α-methyl-p-nitrobenzyl | hydrogen |
| 171 | α-methyl-p-aminobenzyl | hydrogen |
| 172 | α-methyl-o-fluorobenzyl | hydrogen |
| 173 | αcyclohexylbenzyl | hydrogen |
| 174 | 1-phenylcyclopentyl | hydrogen |
| 175 | 1-(phenylthio)ethyl | hydrogen |
| 176 | α-sec-butylbenzyl | hydrogen |
| 177 | 1-phenylcyclopropyl | hydrogen |
| 178 | α-methyl-o-methylbenzyl | hydrogen |
| 179 | (S)-α-methylbenzyl | hydrogen |
| 180 | (R)-α-methylbenzyl | hydrogen |
| 181 | α,α-dimethyl-p-chlorobenzyl | hydrogen |
| 182 | α-methyl-p-chlorobenzyl | hydrogen |
| 183 | α-methyl-o-trifluoromethylbenzyl | hydrogen |
| 184 | α-methyl-o-chlorobenzyl | hydrogen |
| 185 | α-methoxybenzyl | hydrogen |
| 186 | α-methylbenzhydryl | hydrogen |
| 187 | α-ethyl-α-methylbenzyl | hydrogen |
| 188 | α,α-dimethyl-p-fluorobenzyl | hydrogen |
| 189 | 1-methyl-1-(p-chlorophenoxy)-ethyl | hydrogen |
| 190 | benzhydryl | hydrogen |
| 191 | α-ethylbenzyl | hydrogen |
| 192 | α-methylbenzyl | pivaloyl |
| 193 | 2,6-difluorophenyl | pivaloyl |
| 194 | 2-furyl | pentaacetylgluconyl |

TABLE 1(B)

Compounds 195-388.

In all of the compounds 195-388, there is a carbon-carbon single bond between the atoms at positions 22 and 23, X represents a hydrogen atom, R¹ represents a methyl group, and R² and R³ have the corresponding meanings as in compounds 1-194 above.

TABLE 1(C)

Compounds 389-582.

In all of the compounds 389-582, there is a carbon-carbon single bond between the atoms at positions 22 and 23, X represents a hydrogen atom, R¹ represents an isopropyl group, and R² and R³ have the corresponding meanings as in compounds 1-194 above.

TABLE 1(D)

Compounds 583-776.

In all of the compounds 583-776, there is a carbon-carbon single bond between the atoms at positions 22 and 23, X represents a hydrogen atom. R¹ represents a sec-butyl group, and R² and R³ have the corresponding meanings as in compounds 1-194 above.

TABLE 1(E)

In compounds 777-782, there is a carbon-carbon single bond between the atoms at positions 22 and 23, X represents a hydrogen atom, and the groups R¹, R² and R³ have the meanings shown below.

| No. | R¹ | R² | R³ |
|---|---|---|---|
| 777 | cyclopentyl | 2,6-difluorophenyl | pivaloyl |
| 778 | 2-methylcyclopropyl | o-trifluoromethylphenyl | hydrogen |
| 779 | butyl | α,α-dimethylbenzyl | hydrogen |
| 780 | 1-propenyl | α-methylbenzyl | pivaloyl |
| 781 | 2-methoxyethyl | α-methylbenzyl | hydrogen |
| 782 | isobutyl | α-methyl-o-fluorobenzyl | hydrogen |

TABLE 1(F)

In Compounds 783-786, there is a carbon-carbon single bond between the atoms at positions 22 and 23, X represents a hydroxy group, and R¹, R² and R³ have the meanings shown below.

| No. | R¹ | R² | R³ |
|---|---|---|---|
| 783 | cyclopentyl | 2,6-difluorophenyl | hydrogen |
| 784 | 2-cyclohexen-1-yl | α,α-dimethylbenzyl | hydrogen |
| 785 | 1-(methylthio)ethyl | t-butyl | hydrogen |
| 786 | ethynyl | α-methylbenzyl | hydrogen |

TABLE 1(G)

In compounds 787-793, there is a carbon-carbon double bond between the atoms at positions 22 and 23, X represents a hydrogen atom, and R¹, R² and R³ have the meanings shown below.

| No. | R¹ | R² | R³ |
|---|---|---|---|
| 787 | cyclobutyl | α-methylbenzyl | hydrogen |
| 788 | cyclohexyl | α,α-dimethylbenzyl | dimethylcarbamoyl |
| 789 | propyl | 2,6-difluorophenyl | hydrogen |
| 790 | pentyl | α-methylbenzyl | hydrogen |
| 791 | 2-(methylthio)ethyl | α,α-dimethylbenzyl | hydrogen |
| 792 | cyclopropylmethyl | α-methylbenzyl | hydrogen |
| 793 | cyclobutylmethyl | α,α-dimethylbenzyl | hydrogen |

TABLE 1(H)

In compounds 794-799, there is a carbon-carbon single bond between the atoms at positions 22 and 23, X and the ring carbon atom to which it is attached together represent the group C=0, and R¹, R² and R³ have the meanings shown below.

| No. | R¹ | R² | R³ |
|---|---|---|---|
| 794 | 1,3-dimethyl-1-butenyl | 2,6-difluorophenyl | hydrogen |
| 795 | 1,3-dimethyl-1-butenyl | 2,6-difluorophenyl | propionyl |
| 796 | 1,3-dimethyl-1-butenyl | α-methylbenzyl | hydrogen |
| 797 | 1-methyl-1-butenyl | α,α-dimethylbenzyl | hydrogen |
| 798 | 1,3-dimethyl-1-butenyl | o-trifluorophenyl | hydrogen |
| 799 | 1,3-dimethyl-1-butenyl | t-butyl | hydrogen |

TABLE 2(A)

In compounds 1-104, there is a carbon-carbon single bond between the atom at positions 22 and 23, X represents a hydrogen atom, and R¹, R² and Y have the meanings shown below.

| No. | R¹ | R² | Y |
|---|---|---|---|
| 1 | methyl | α-methylbenzyl | —OH |
| 2 | ethyl | α-methylbenzyl | —OH |
| 3 | isopropyl | α-methylbenzyl | —OH |

TABLE 2(A)-continued

In compounds 1-104, there is a carbon-carbon single bond between the atom at positions 22 and 23, X represents a hydrogen atom, and $R^1$, $R^2$ and Y have the meanings shown below.

| No. | $R^1$ | $R^2$ | Y |
|---|---|---|---|
| 4 | sec-butyl | α-methylbenzyl | —OH |
| 5 | ethyl | α-ethylbenzyl | —OH |
| 6 | ethyl | α-propylbenzyl | —OH |
| 7 | ethyl | α-isopropylbenzyl | —OH |
| 8 | ethyl | α-butylbenzyl | —OH |
| 9 | ethyl | α-sec-butylbenzyl | —OH |
| 10 | ethyl | benzhydryl | —OH |
| 11 | ethyl | α,α-dimethylbenzyl | —OH |
| 12 | sec-butyl | α,α-dimethylbenzyl | —OH |
| 13 | ethyl | α-ethyl-α-methylbenzyl | —OH |
| 14 | ethyl | α-isopropyl-α-methylbenzyl | —OH |
| 15 | ethyl | α-methylbenzhydryl | —OH |
| 16 | ethyl | α,α-diethylbenzyl | —OH |
| 17 | ethyl | α-methyl-p-chlorobenzyl | —OH |
| 18 | ethyl | α-methyl-m-chlorobenzyl | —OH |
| 19 | ethyl | α-methyl-o-chlorobenzyl | —OH |
| 20 | ethyl | α-methyl-p-fluorobenzyl | —OH |
| 21 | ethyl | α-methyl-p-trifluoromethylbenzyl | —OH |
| 22 | ethyl | α-methyl-o-trifluoromethylbenzyl | —OH |
| 23 | ethyl | α-methyl-p-cyanobenzyl | —OH |
| 24 | ethyl | α-methyl-p-methylbenzyl | —OH |
| 25 | ethyl | α-methyl-p-methoxybenzyl | —OH |
| 26 | ethyl | α-methyl-p-nitrobenzyl | —OH |
| 27 | ethyl | α,α-dimethyl-p-chlorobenzyl | —OH |
| 28 | ethyl | α,α-dimethyl-p-fluorobenzyl | —OH |
| 29 | ethyl | α,α-diethyl-p-chlorobenzyl | —OH |
| 30 | ethyl | α-methyl-2,4-dichlorobenzyl | —OH |
| 31 | ethyl | α-methyl-2,6-dichlorobenzyl | —OH |
| 32 | ethyl | α-methyl-2,4-difluorobenzyl | —OH |
| 33 | ethyl | α-methyl-2,6-difluorobenzyl | —OH |
| 34 | ethyl | α-methyl-3-nitro-4-chlorobenzyl | —OH |
| 35 | ethyl | α-methoxybenzyl | —OH |
| 36 | ethyl | α-ethoxybenzyl | —OH |
| 37 | ethyl | α-methoxymethylbenzyl | —OH |
| 38 | ethyl | α-methoxyethylbenzyl | —OH |
| 39 | ethyl | α-chloromethylbenzyl | —OH |
| 40 | ethyl | α-chloromethyl-α-methylbenzyl | —OH |
| 41 | ethyl | α-fluoromethylbenzyl | —OH |
| 42 | ethyl | α-fluoromethyl-α-methylbenzyl | —OH |
| 43 | ethyl | α-cyanobenzyl | —OH |
| 44 | ethyl | 1-(3-pyridyl)ethyl | —OH |
| 45 | ethyl | 1-(2-pyridyl)ethyl | —OH |
| 46 | ethyl | 1-(4-pyridyl)ethyl | —OH |
| 47 | ethyl | 1-(2-thienyl)ethyl | —OH |
| 48 | ethyl | 1-(2-furyl)ethyl | —OH |
| 49 | ethyl | 1-(2-benzothienyl)ethyl | —OH |
| 50 | ethyl | 1-(2-benzofuranyl)ethyl | —OH |
| 51 | ethyl | 1-methyl-2-phenylethyl | —OH |
| 52 | ethyl | 1,1-dimethyl-2-phenylethyl | —OH |
| 53 | ethyl | 1-phenoxyethyl | —OH |
| 54 | ethyl | 1-methyl-1-phenoxyethyl | —OH |
| 55 | ethyl | 1-(p-chlorophenoxy)ethyl | —OH |
| 56 | ethyl | 1-methyl-1-(p-chlorophenoxy)ethyl | —OH |
| 57 | ethyl | 1-[p-(phenoxy)phenoxy]ethyl | —OH |
| 58 | ethyl | 1-[p-(p-chlorophenoxy)phenoxy]ethyl | —OH |
| 59 | ethyl | 1-[p-(2,4-dichlorophenoxy)-phenoxy]ethyl | —OH |
| 60 | ethyl | 1-[p-(p-trifluoromethylphenoxy)-phenoxy]ethyl | —OH |
| 61 | ethyl | 1-[p-(5-trifluoromethyl-2-pyridyloxy)-phenoxy]ethyl | —OH |
| 62 | ethyl | 1-[p-(3-chloro-5-trifluoromethyl-2-pyridyloxy)phenoxy]ethyl | —OH |
| 63 | ethyl | 1-[3-chloro-4-(5-trifluoromethyl-2-pyridyloxy)phenoxy]ethyl | —OH |
| 64 | ethyl | 1-[p-(6-chloro-2-benzoxazolyloxy)-phenoxy]ethyl | —OH |
| 65 | ethyl | 1-[p-(6-chloro-1,4-dihydro-2-quinoxalinyloxy)phenoxy]ethyl | —OH |
| 66 | ethyl | α-methyl-o-fluorobenzyl | —OH |
| 67 | ethyl | α-cyclohexylbenzyl | —OH |
| 68 | ethyl | 1-phenylcyclopropyl | —OH |
| 69 | ethyl | 1-(phenylthio)ethyl | —OH |
| 70 | ethyl | 1-phenylcyclopropyl | —OH |
| 71 | ethyl | α-methyl-o-methylbenzyl | —OH |
| 72 | ethyl | (S)-α-methylbenzyl | —OH |
| 73 | ethyl | (R)-α-methylbenzyl | —OH |
| 74 | ethyl | α-methyl-p-aminophenyl | —OH |

TABLE 2(A)-continued

In compounds 1-104, there is a carbon-carbon single bond between the atom at positions 22 and 23, X represents a hydrogen atom, and $R^1$, $R^2$ and Y have the meanings shown below.

| No. | $R^1$ | $R^2$ | Y |
|---|---|---|---|
| 75 | ethyl | 1-(2-pyridon-1-yl)ethyl | —OH |
| 76 | ethyl | 1-(2-piperidon-1-yl)ethyl | —OH |
| 77 | ethyl | 1-(2-piridyl)ethyl | —OH |
| 78 | 1,3-dimethyl-1-butenyl | α-methylbenzyl | —OH |
| 79 | cyclopentyl | α,α-dimethylbenzyl | —OH |
| 80 | 2-methylcyclopropyl | α-methylbenzyl | —OH |
| 81 | butyl | α,α-dimethylbenzyl | —OH |
| 82 | 1-propenyl | α-methylbenzyl | —OH |
| 83 | 2-methoxyethyl | α-methylbenzyl | —OH |
| 84 | isobutyl | α-methyl-o-fluorobenzyl | —OH |
| 85 | ethyl | α-methylbenzyl | acetoxy |
| 86 | ethyl | α-methylbenzyl | chloroacetoxy |
| 87 | ethyl | α-methylbenzyl | propionyloxy |
| 88 | ethyl | α-methylbenzyl | acetoxyacetoxy |
| 89 | ethyl | α-methylbenzyl | ethoxycarbonyloxy |
| 90 | ethyl | α-methylbenzyl | 2,3-dihydroxypropoxycarbonyloxy |
| 91 | ethyl | α-methylbenzyl | 3,4-dihydro-2H-pyran-2-yl-carbonyloxymethoxycarbonyloxy |
| 92 | ethyl | α,α-dimethylbenzyl | propionyloxy |
| 93 | ethyl | α,α-dimethylbenzyl | chloroacetoxy |
| 94 | ethyl | α,α-dimethylbenzyl | pivaloyloxyacetoxy |
| 95 | ethyl | α,α-dimethylbenzyl | 3-carboxypropionyloxy |
| 96 | ethyl | α,α-dimethylbenzyl | ethoxycarbonyloxy |
| 97 | ethyl | α,α-dimethylbenzyl | (2,2-dimethyl-1,3-dioxolanyl)methoxycarbonyloxy |
| 98 | ethyl | α,α-dimethylbenzyl | imidazol-1-yl-methoxycarbonyloxy |
| 99 | ethyl | α-methyl-p-chlorobenzyl | chloroacetoxy |
| 100 | ethyl | α-methyl-p-phenoxybenzyl | trifluoroacetoxy |
| 101 | ethyl | α-methyl-o-chlorobenzyl | chloroacetoxy |
| 102 | ethyl | α-methyl-o-chlorobenzyl | ethoxycarbonyloxy |
| 103 | ethyl | α,α-dimethylbenzyl | chloroacetoxy |
| 104 | ethyl | α,α-dimethylbenzyl | acetoxyaceoxy |

TABLE 2(B)

In compounds 105-108, there is a carbon-carbon single bond between the atoms at positions 22 and 23, X represents a hydroxy group, and $R^1$, $R^2$ and Y have the meanings shown below.

| No. | $R^1$ | $R^2$ | Y |
|---|---|---|---|
| 105 | cyclopentyl | α-methylbenzyl | —OH |
| 106 | 1-(methylthio)ethyl | α-methylbenzyl | —OH |
| 107 | ethynyl | α-methylbenzyl | —OH |
| 108 | 2-cyclohexen-1-yl | α-methylbenzyl | acetoxycarbonyloxy |

TABLE 2(C)

In compounds 109-115, there is a carbon-carbon double bond between the atoms at positions 22 and 23, X represents a hydrogen and $R^1$, $R^2$ and Y have the meanings shown below.

| No | $R^1$ | $R^2$ | Y |
|---|---|---|---|
| 109 | cyclopentyl | α,α-dimethylbenzyl | —OH |
| 110 | cyclohexyl | α-methylbenzyl | —OH |
| 111 | propyl | α-methylbenzyl | —OH |
| 112 | 2-(methylthio)ethyl | α,α-dimethylbenzyl | —OH |
| 113 | cyclopropylmethyl | α,α-dimethylbenzyl | —OH |
| 114 | cyclobutylmethyl | α,α-dimethylbenzyl | —OH |
| 115 | cyclobutyl | α-methylbenzyl | chloroacetoxy |

TABLE 2(D)

In compounds 116-120, there is a carbon-carbon single bond between the atoms at positions 22 and 23, X and the ring carbon atom to which it is attached together represent the group C = 0, and $R^1$, $R^2$ and Y have the meanings shown below.

| No. | $R^1$ | $R^2$ | Y |
|---|---|---|---|
| 116 | 1,3-dimethyl-1-butenyl | α-methylbenzyl | —OH |
| 117 | 1,3-dimethyl-1-butenyl | α,α-dimethylbenzyl | —OH |
| 118 | 1-methyl-1-butenyl | α-methylbenzyl | —OH |
| 119 | 1,3-dimethyl-1-butenyl | α-methylbenzyl | chloroacetoxy |
| 120 | 1,3-dimethyl-1-butenyl | α-methylbenzyl | acetoxyacetoxy |

The most highly preferred compounds are those with numbers 1, 2, 3, 26, 45, 55, 61, 90, 102, 108, 122, 123, 171 and 191 in Table 1(A), and those with numbers 2, 5, 7, 11, 13, 19, 86 and 88 in Table 2(A).

The compounds of formula (I) wherein Y represents the group =N—OR$^3$ and R$^2$ represents the group R$^5$—(O)$_n$— can be prepared from the corresponding 13-substituted 5-ketomilbemycins of formula (III), by the processes shown in Reaction Scheme No. 1, in which R$^1$, R$^3$, R$^5$, X, n and the broken line have the meanings already defined.

REACTION SCHEME No. 1

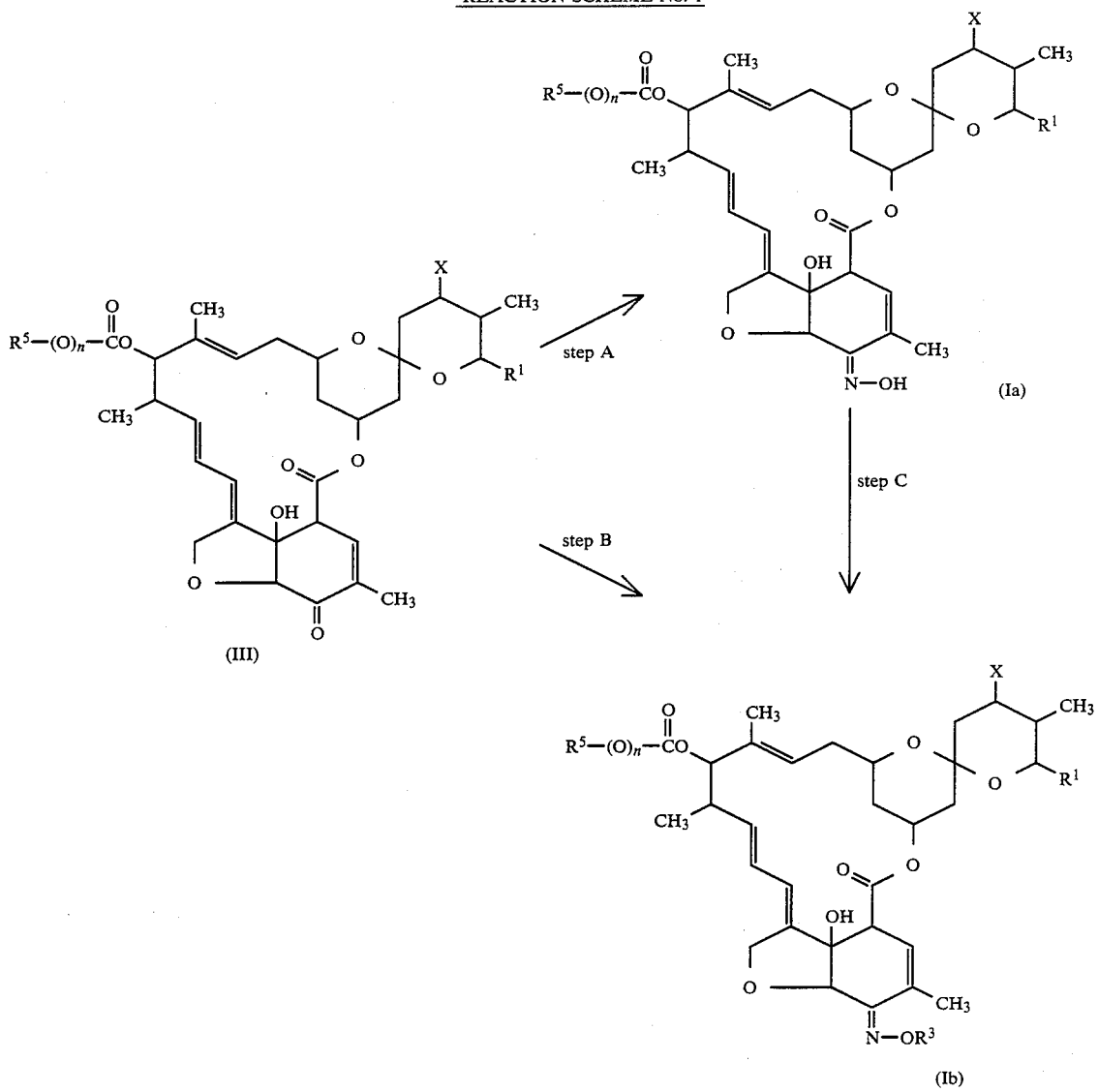

In reaction Scheme No. 1, Step A is for preparing a compound of the formula (Ia) by allowing a compound of the formula III) to react with hydroxylamine or with one of its salts (for example, the salt with a mineral acid such as hydrochloric acid, nitric acid or sulfuric acid) to introduce the oxime group at the 5 position. The reaction is usually carried out in an inert solvent, for example an alcohol such as merhanol or ethanol, an ether such as tetrahydrofuran or dioxane, an aliphatic acid such as acetic acid, water or a mixture of such solvents. The reaction temperature is preferably from 10° to 80° C. and the reaction usually requires from 1 hour to 24 hours to be complete.

Step B is for preparing a compound of the formula (Ib) by allowing the compound (III) to react with an oxime compound having the general formula $NH_2OR^3$ (wherein $R^3$ has the same meaning as before) or with one of its salts (e.g.the same salts as in Step A), to introduce the oxime group at the 5 position. The conditions required for this reaction are similar to those for Step A.

Step C is for preparing a compound of formula (Ib) by esterification of the oxime group of the compound (Ia). This reaction can be used to prepare the preferred compounds of formula (X) above, in which the group corresponding to $R^3$ is $R^{13}$ and represents an ester residue of a carboxylic acid, an N,N-di-substituted carbamic acid, a carbonic acid, a sulfonic acid or a phosphonic acid, by allowing a compound (Ia) in which $R^3$ is a hydrogen atom to react with a corresponding acid halide, usually in an inert solvent, preferably in the presence of a base. This method is a preferred embodiment of the invention.

The base employed is not particularly limited provided that it has an acid binding ability and an organic amine such as triethylamine, N,N-dimethylaniline, pyridine, 4-dimethylaminopyridine, 1,4-diazabicyclo[2.2.-2]octane, 5-diazabicyclo[4.3.0]nonene-5 or 1,8-diazabicyclo[5.4.0]undecene-7 is preferred.

The inert solvent employed is not particularly limited provided that it does not interfere with the reaction, and a hydrocarbon such as hexane, benzene, toluene or xylene, an ether such as diethyl ether, tetrahydrofuran or dioxane, or a halogenated hydrocarbon such as methylene chloride, chloroform or carbon tetrachloride is preferred.

The compound of the formula (X) in which $R^{13}$ is a residue of an N-substituted carbamic acid can be prepared by allowing a compound of the formula (I) in which $R^3$ is a hydrogen atom to react with a corresponding isocyanate in an inert solvent, in the presence of a base. The base and the inert solvent employed can be the same as in the steps mentioned before. The reaction is usually carried out at near room temperature and the reaction usually requires from 1 to 20 hours to be complete.

The compound in which $R^{13}$ is an N-trihaloacetylcarbamoyl group, obtained by the above reaction, can be converted into a compound in which $R^{13}$ is a carbamoyl group by reaction with zinc-acetic acid or zinc-methanol.

After completion of each of these reactions, the target compound of the reaction can be obtained easily from the reaction mixture by conventional means. For example, the reaction mixture is poured into water and, if necessary, after filtering off the insoluble matter followed by neutralization with an acid or an alkali, extracted with a water-immiscible organic solvent. The organic layer is dried and the solvent distilled off to give the desired product. If desired, purification by conventional means such as recrystallization, column chromatography, etc., may be applied.

The starting material of formula (III) can be prepared from a 13-hydroxy-5-ketomilbemycin compound having the general formula (IV) by the reaction shown in Reaction Scheme No. 3, in which $R^1$, $R^5$, X, n and the broken line have the meanings already defined.

REACTION SCHEME No. 3

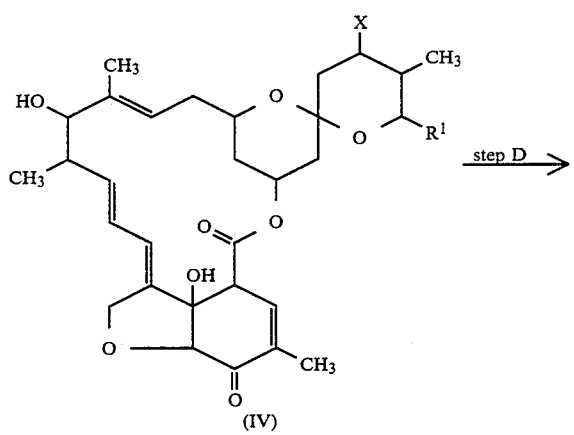

(IV)

-continued
REACTION SCHEME No. 3

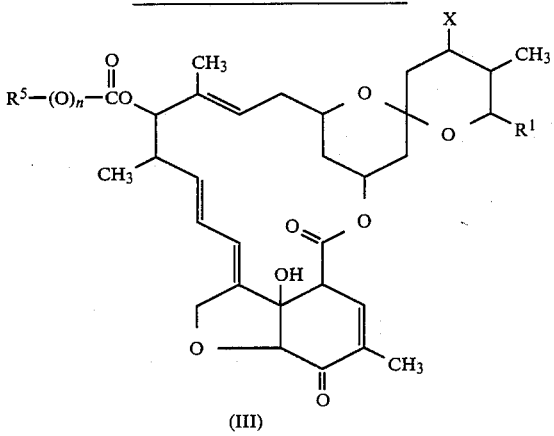

(III)

Step D is for preparing a compound of the formula (III) by allowing a 13-hydroxy-5-ketomilbemycin compound indicated by the formula (IV) to react with a carboxylic acid or its reactive derivative indicated by the formula (V). Compounds of formula (IV) are known from U.S. Pat. No. 4,423,209.

The reaction of Step D is an esterification of the hydroxyl group at position 13 of the compound (IV) with a carboxylic acid (V), and can be carried out according to any of the conventional procedures known for esterification reactions. The reactive derivative of a carboxylic acid employed may be for example an acid halide (an acid chloride, acid bromide or the like), an acid anhydride a mixed acid anhydride an active ester such as a p-nitrobenzyl ester, an active amide or the like, which can be conventionally used in esterifications.

When a carboxylic acid of the formula (V) is employed as such, it is preferred to use a dehydrating agent such as dicyclohexylcarbodiimide (DCC), p-toluenesulfonic acid or sulfuric acid. In particular, DCC is preferably used, and when DCC is used, preferably a catalytic amount of pyridine or 4-pyrrolidinopyridine may be jointly used.

When DCC is used as the dehydrating agent, its amount is usually from 1 to 5 equivalents, preferably from 1.5 to 4 equivalents.

The reaction is usually carried out in a solvent. The solvent employed is not particularly limited provided that it does not interfere with the reaction, and a hydrocarbon such as hexane, petroleum ether, benzene, toluene, xylene, chloroform, methylene chloride or o-chlorobenzene, an ether such as diethyl ether, tetrahydrofuran, dioxane or ethyleneglycol dimethyl ether, or an ester such as methyl acetate or ethyl acetate or the like may be employed.

The reaction is usually carried out at from 0° C. to 50° C., preferably from 0° C. to 20° C. The reaction usually requires from 30 minutes to 3 hours to be complete.

When an acid halide derived from a carboxylic acid of the formula (V) is employed, the reaction is preferably carried out in the presence of a base, preferably an organic base such as triethylamine, N,N-dimethylaniline, pyridine, 4-dimethylaminopyridine, 1,5-diazabicyclo[4.3.0]nonene-5 (DBN) or 1,8-diazabicyclo[5.4.0]undecene-7 (DBU).

The amount of this acid halide is usually from 1 to 10 equivalents, and from 2 to 5 equivalents of the base is usually used.

The solvent, reaction temperature and reaction time employed for this reaction are similar to those when a carboxylic acid is used.

After completion of the reaction, the target compound having the formula (III) can be isolated from the reaction mixture by conventional means and, if desired, further purified by conventional means such as column chromatography.

The starting material of formula (IV) can be derived from one of the milbemycins or milbemycin analogues of natural origin, by per se known methods, such as those described in the various prior art references mentioned earlier in this specification. Natural milbemycins are produced as mixtures of various compounds, the different compounds being produced at different rates. Each fraction may be subjected to reaction after isolation thereof, or in the form of mixtures of the individual products. Therefore, the compound having the formula (IV) may be either a single compound or a mixture thereof, which may result in forming the compound (I) either as a single compound or as a mixture.

The compounds of formula (I) wherein Y represents the group -OR$^4$ and R$^2$ represents the group A—(W-)$_n$—C(R$^6$R$^7$)— can be prepared from the corresponding 13-hydroxy-5-ketomilbemycins of formula (II), by the processes shown in Reaction Scheme No. 2, in which R$^1$, R$^6$, R$^7$, X, A, W, n and the broken line have the meanings already defined, and R$^{4a}$ represents a carboxylic or carbonic acid residue.

REACTION SCHEME No. 2
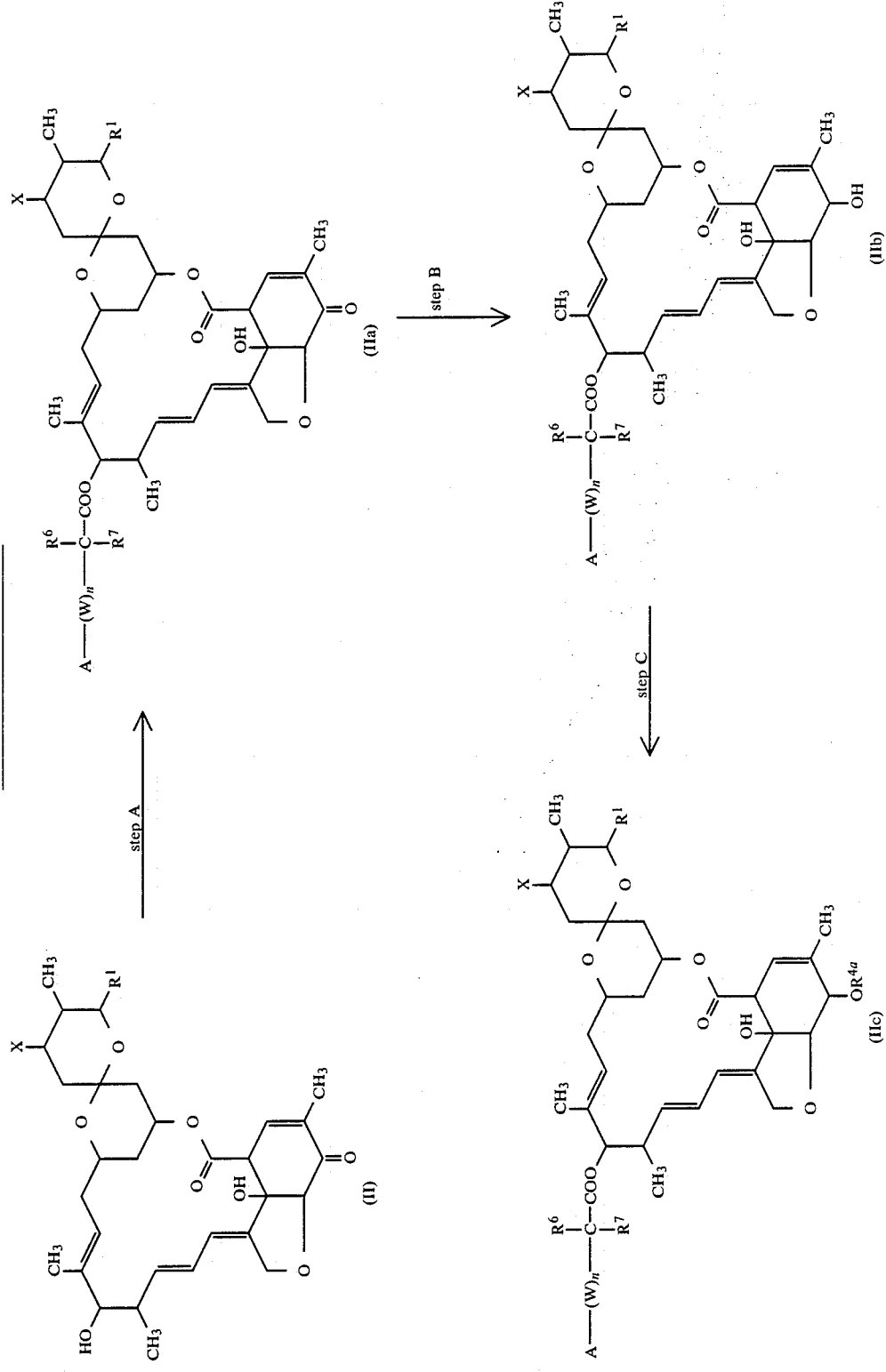

Of the starting compounds (II), those in which $R^1$ is the methyl, ethyl, isopropyl or sec-butyl group may be prepared by the methods disclosed in U.S. Pat. No. 4,423,209 or Japanese Patent Kokai 61-103884. Compounds in which $R^1$ is the 1-methyl-1-propenyl 1-methyl-1-butenyl or 1,3-dimethyl-1-butenyl group may be prepared by dehydrating compound LL-F28249 in which the 23-position is OH, disclosed in European Patent Publication No. 170 006, by the method described in "Pesticide Chemistry", by J. Miyamoto and P. C. Kearny, Pergamon Press, Vol. 1, pp 83 (1983) to give the corresponding compound whose 22- and 23-positions are the double bond, and then by reducing this compound. Alternatively, it may be prepared by converting the OH group at the 23-position to a suitable thioester, by conventional techniques, and then reducing the resulting compound by the same method as before.

Step A in Reaction Scheme 2 comprises reacting a compound of formula (II) with a carboxylic acid of formula (VI):

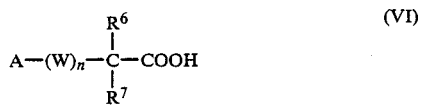

$$A-(W)_n-\underset{\underset{R^7}{|}}{\overset{\overset{R^6}{|}}{C}}-COOH \qquad (VI)$$

(wherein, $R^6$, $R^7$, W, n and A are as defined above) or a reactive derivative thereof to give the 13-ester compound of formula (IIa).

Step A consists in an esterification reaction between the hydroxy group at the 13-position of compound (II) and the carboxylic acid (VI), and hence it may be performed by any conventional method known per se.

The reactive derivative of the carboxylic acid (VI) includes, for example, acid halides (such as the acid chloride, acid bromide or acid iodide), acid anhydrides, mixed acid anhydrides, active esters (such as p-nitrobenzyl ester) and active amides that may be normally used in esterification reactions.

Where a carboxylic acid of formula (VI) is used as such, there is preferably used a dehydrating agent such as dicyclohexylcarbodiimide (DCC), p-toluenesulfonic acid or sulfuric acid more preferably DCC. Where DCC is used, there is preferably used a catalytic amount of pyridine, 4-pyrrolidinopyridine or the like. The amount of DCC is normally from 1 to 5 equivalents, preferably from 1.5 to 4 equivalents.

The reaction is normally effected in the presence of a solvent, the nature of which is not critical, provided that it has no adverse effect upon the reaction. Suitable solvents include, for example, hydrocarbons such as hexane, petroleum ether, benzene, toluene, xylene, chloroform methylene chloride or o-chlorobenzene, ethers such as diethyl ether, tettrahydrofuran, dioxane or ethylene glycol dimethyl ether, and esters such as methyl acetate or ethyl acetate. Normally, the reaction is carried out at a temperature in the range of from 0° C. to 100° C., preferably from 20° C. to 50° C. for a period of from 30 minutes to 3 hours.

Where an acid halide of the carboxylic acid (VI) is used, the reaction is preferably carried out in the presence of a base.

Suitable bases include, for example, triethylamine, N,N-dimethylaniline, pyridine, 4-dimethylaminopyridine, 1,5-diazabicyclo[4.3.0]nonene-5 (DBN) and 1,8-diazabicyclo[5.4.0]-undecene-7 (DBU).

Normally, the amount of the acid halide of the carboxylic acid (VI) is from 1 to 10 equivalents and the amount of the base is from 2 to 8 equivalents.

The nature of solvents used, the reaction temperature and the reaction time are similar to those when a carboxylic acid itself is used.

Step B consists in reducing the carbonyl group at the 5-position of the compound (IIa) to the hydroxy group, and this may be effected by any reducing method known per se (see Japanese Patent Application 60-210748). However, it is necessary not to damage any part of the molecule other than the 5-position and hence it is desirable that the reduction is carried out with anionic hydrogen. Reagents capable of liberating anionic hydrogen include, for example, sodium borohydride and diborane, of which sodium borohydride is most preferred. The amount of reducing agent is normally from 1 to 5 equivalents, preferably from 1 to 2 equivalents.

The reaction is normally carried out in the presence of a solvent, the nature of which is not critical, provided that it does not have any adverse effect upon the reaction. Examples of suitable solvents include, for example, methanol, ethanol, diethyl ether, tetrahydrofuran and benzene.

Normally, the reaction is performed at a temperature in the range of from $-10°$ C. to 50° C., preferably from 0° C. to 20° C. for a period of from 30 minutes to 3 hours.

Step C consists in reacting a compound of formula (IIb) with a carboxylic acid or carbonic acid, or a reactive derivative thereof, to give a 5-ester derivative of formula (IIc). This reaction is an esterification reaction between the hydroxy group at the 5-position of the compound (IIb) and an acid, and therefore, it may be performed by any esterification reaction known per se as in Step A.

The nature of the reactive derivative of the acid, the dehydrating agent, the solvent, the reaction temperature, the reaction period and the base can all be the same as in Step A.

After completion of the reaction in each step, the desired compound of formulae (IIa), (IIb) and (IIc) may be recovered from the reaction mixture by well known means and, if necessary, further purified by such conventional techniques as column chromatography.

The compounds of formula (II) which are used as starting materials are milbemycin compounds or milbemycin analogues which are fermentation products, or can be obtained from the natural products by known techniques, such as those mentioned in the prior art references set out earlier in this specification. Normally, the milbemycins are produced as mixtures of several compounds, the different compounds being produced at different rates. Each compound may be isolated and subsequently subjected to the reactions. Alternatively, mixtures of the compounds may be subjected to the reactions.

Thus, the compound of formula (II) may be either a single compound or a mixture of compounds, and hence, the compound of formula (I) may be either a single compound or a mixture of compounds.

The compounds of the invention having a 23-keto group can be obtained from the corresponding natural product, for example, by the following sequence of steps. The natural product having a 5-hydroxy group is oxidized to the corresponding 5-oxo compound e.g. with manganese dioxide. The 5-oxo derivative is treated with a lower alkanoic acid (e.g. formic acid) and selenium dioxide, and then with aqueous hydrochloric acid, giving the corresponding 13-hydroxy-5-oxo derivative—i.e. a compound of formula (II) above. The 13-hydroxy group can then be acylated with the appropriate carboxylic acid or reactive derivative thereof, in the manner already described, to give the corresponding 13-esterified-5-oxo compound, such as a compound of formula (Ia) or (IIa) above. The 5-oxo group can then be converted to the 5-oxime, using the methods already described; or it can be converted to a 5-hydroxy group by reducing it e.g. with sodium borohydride.

The compounds of the invention have a strong acaricidal activity against, for example, adults, imagos and eggs of Tetranychus, Panonychus (e.g. *Panonychus ulmi* and *Panonychus citri*), *Aculopa pelekassi* and rust mites, which are parasitic to fruit trees, vegetables and flowers. They are also active against Ixodidae, Dermanyssidae and Sarcoptidae, which are parasitic to animals. Further, they are active against: exoparasites, such as Oestrus, Lucilia, Hypoderma Gautrophilus, lice and fleas which are parasitic to animals and birds, particularly livestock and poultry; domestic insects, such as cockroaches and houseflies; and various harmful insects in agricultural and horticultural areas, such as aphids and larval Lepidoptera. They are also effective against Meloidogyne in the soil, Bursaohelenchus and Rhizoglyphus. They are also effective against insects of the orders Coleoptera Homoptera, Heteroptera, Diptera, Thysanoptera, Orthoptera, Anoplura, Siphonaotera, Mallophage Thysanura, Isoptera, Psocoptera, and Hymenoptera.

The compounds of the invention equally can be used to control other plant-damaging insects, particularly insects that damage plants by eating them. The compounds can be used to protect both ornamental plants and productive plants, particularly cotton (e.g. against *Spodoptera littoralis* and *Heliothis virescens*), as well as vegetable crops (e.g. against *Leptinotarsa decemlineata* and *Myzus persicae*) and rice crops (e.g. against *Chilo suppressalis* and Laodelphax).

The activity of the compounds of the invention is pronounced, both systemically and by contact. Accordingly, the compounds are very effective against sucking insects, especially sucking insects of the order Homoptera and most particularly the family Aphididae (such as *Aphis fabae*, *Aphis craccivora* and *Myzus persicae*), which are difficult to control with known compositions.

Accordingly, the compounds of the invention can be used to treat all manner of plants (as well as the seeds from which such plants are grown and the environment, whether for growth or storage, containing such plants) to protect them from insects such as those exemplified above. Such plants include cereals (e.g. maize or rice), vegetables (e.g. potatoes or soybeans), fruits and other plants (e.g. cotton).

The compounds of the invention can similarly be used to protect animals from a variety of ectoparasites, by applying the compounds to the animals or to the animals environment, e.g. livestock housing, animal boxes, abattoirs, pasture land and other grasslands, as well as to any other places liable to be infested. The compounds may also be applied to external parts of the animals, preferably before they are infested.

Moreover, the compounds of the invention are effective against various parasitical helminths. These parasites can attack livestock, poultry and pet animals (such as pigs, sheep, goats, cows, horses, dogs, cats and fowl) and can cause grave economic damage. Among the helminths, the nematodes in particular often cause serious infection. Typical genera of nematodes which are parasitic on these animals and against which the compounds of the invention are effective include:
Haemonchus,
Trichostrongylus,
Ostertagia.
Nematodirus,
Cooperia,
Ascaris,
Bunostomum,
Oesophagostomum,
Chabertia,
Trichuris,
Strongylus,
Trichonema,
Dictyocaulus,
Capillaria,
Heterakis,
Toxocara,
Ascaridia,
Oxyuris,
Ancylostoma,
Uncinaria,
Toxascaris and
Parascaris.

Certain parasitical species of the genera Nemarodirus, Cooperia and Oesophagostomum attack the intestines, while certain species of the genera Haemonchus and Ostertagia parasitize the stomach, and parasites belonging to the genus Dictyocaulus are found in the lungs. Parasites belonging to the families Filariidae and Setariidae are found in internal tissues and organs, for example, the heart, the blood vessels, the subcutaneous tissues and the lymphatic vessels. The compounds of the invention are active against all these parasites.

The compounds of the invention are also effective against parasites which infect humans. Typical of the parasites which may most commonly be found in the digestive tracts of human beings are parasites of the genera Ancylostoma, Necator, Ascaris, Strongyloides, Trichinella, Capillaria, Trichuris and Enterobius. The compounds are also active against parasites of the genera Wuchereria, Brugia, Onchocerca and Loa of the family Filariidae (which are found in blood tissues and organs other than the digestive tract and are medically important), parasites of the genus Dracunculus of the family Dracunculidae and parasites of the genera Strongyloides and Trichinella, which in a particular state may parasitize outside the intestinal tract, although they are essentially intestinal parasites.

The form of the compositions of the invention and the nature of the carriers or diluents employed in them will vary depending upon the intended use of the composition. For example, where the compounds of the invention are to be employed as anthelmintics, they are preferably administered orally, parenterally or topically and the form of compositions chosen will be appropriate to the intended route of administration.

For oral administration, the composition of the invention is preferably in the form of a liquid drink comprising a non-toxic solution, suspension or dispersion of the active compound in admixture with a suspending agent (such as bentonite), a wetting agent or other diluents, preferably in water or another non-toxic solvent. The drink, in general, also contains an anti-foaming agent. The active compound would normally be present in the drink in an amount of from 0.01 to 0.5% by weight, more preferably from 0.01 to 0.1% by weight.

Compositions for oral administration may also be in the form of dry solids, preferably in unit dosage form, such as capsules, pills or tablets containing the desired amount of the active compound. These compositions may be prepared by mixing the active compound uniformly with suitable diluents, fillers disintegrators and/or binding agents, for example starch, lactose, talc, magnesium stearate and vegetable gum. The weight and contents of the preparation will vary widely, depending upon the nature of the animal to be treated, the degree of infection, the nature of the parasite and the body weight of the animal to be treated.

The compounds may also be administered as an additive to animal feedstuffs, in which case they may be dispersed uniformly in the feedstuffs used as a top dressing or used in the form of pellets. The content of active compound in the feedstuff is preferably from 0.0001 to 0.02%, in order to achieve the desired anthelmintic activity.

For parenteral administration, the compound of the invention is preferably dissolved or suspended in a liquid vehicle, preferably a vegetable oil, such as peanut oil or cottonseed oil. Where the compound is a salt of a compound of formula (II), the liquid vehicle may be water or another aqueous medium. Depending upon the animal to be treated, the injection may be subcutaneous or into the proventriculus, a muscle or the trachea. Such preparations would normally contain the active compound at a concentration of from 0.05 to 50% by weight.

The compounds of the invention may also be administered topically in admixture with a suitable carrier, such as dimethyl sulphoxide or a hydrocarbon solvent. Such preparations would be applied directly to the outside of the animal by spraying (e.g. by a hand spray or in spray races), by dipping (e.g. in a plunge dip), by a pour-on solution or by manual methods (e.g. hand-dressing).

The dose of active compound may be varied, depending upon the nature of the animal to be treated, and the nature and degree of parasitic infection. However, best results for oral administration are achieved when the dose is from 0.01 to 100 mg, more preferably from 0.5 to 50 mg. per 1 kg body weight. The compound may be administered in a single dose or in divided doses for a relatively short period, such as from 1 to 5 days.

Where the composition of the invention is intended for agricultural or horticultural use, a variety of forms and formulations is possible. For example, the composition may be formulated as dusts, coarse dusts, soluble powders, microgranules, fine microgranules, wettable powders, dilute emulsions, emulsifiable concentrates, aqueous or oily suspensions, dispersions or solutions (which may be directly sprayable or for dilution), aerosols or capsules in, for example, polymeric substances. The carrier employed may be natural or synthetic and organic or inorganic; it is generally employed to assist the active compound to reach the substrate to be treated, and to make it easier to store, transport or handle the active compound. Solid, liquid and gaseous carriers may be employed, chosen from carriers well known in the art for use with compositions of this type.

Such formulations may be prepared by conventional means, e.g. by intimate mixing and/or grinding of the active ingredient(s) with the carrier or diluent, e.g. solvent, solid carrier or, optionally, surface-active agent.

Suitable solvents include: aromatic hydrocarbons, preferably the $C_8$ to $C_{12}$ fractions from petroleum distillation, such as xylene mixtures or substituted naphthalenes; esters of phthalic acid, such as dibutyl or dioctyl phthalate; aliphatic hydrocarbons, such as cyclohexane or the paraffins; alcohols and glycols or esters thereof, such as ethanol, ethylene glycol, ethylene glycol monomethyl ether or ethylene glycol monoethyl ether; ketones, such as cyclohexanone; strongly polar solvents, such as N-methyl-2-pyrrolidone, dimethyl sulfoxide or N,N-dimethylformamide; optionally epoxidized vegetable oils, such as epoxidized coconut oil or soybean oil; and water.

Solid carriers, which may be used, for example, in dusts and dispersible powders, include natural mineral fillers, such as calcite, talc, kaolin, montmorillonite or attapulgite. In order to improve the physical properties of the composition, it is also possible to add highly dispersed silicic acid or highly dispersed absorbent polymers. Suitable granulated adsorptive carriers may be porous (such as pumice, ground brick, sepiolite or bentonite) or non-porous (such as calcite or sand). A wide variety of pregranulated materials, organic or inorganic, may also be used; examples include dolomite and ground plant residues.

Surface-active agents which may be used are well known in the art and may be non-ionic, cationic or anionic agents having good emulsifying, dispersing and wetting properties. Mixtures of such agents may also be used.

Compositions may also contain stabilizers, anti-foaming agents, viscosity regulators, binders or adhesives or any combination thereof, as well as fertilizers or other active substances to achieve special effects.

Pesticidal compositions will generally contain: from 0.01 to 99%, more preferably from 0.1 to 95%, by weight of the active compound; from 1 to 99.99% of a solid or liquid additive; and from 0 to 25%, more preferably from 0.1 to 25%, of a surface-active agent. Whereas commercial products are generally sold as concentrated compositions, they are generally diluted by the end-user to a concentration of from 0.001 to 0.0001% by weight (from 10 to 1 ppm).

The invention is further illustrated by the following non-limiting Examples and Preparations.

Examples 1 to 128 illustrate the preparation of compounds of formula (I) wherein Y represents the group $=N-OR^3$ and $R^2$ represents the group $R^5-(O)_n-$.

Examples 129 to 163 illustrate the preparation of compounds of formula (I) wherein Y represents the group $-OR^4$ and $R^2$ represents the group $A-(W)_n-C(R^6R^7)-$, but for brevity the symbol Z has been used in place of $A-(W)_n-C(R^6R^7)-$ in these Examples.

Preparations 1 to 4 illustrate the synthesis of starting materials for use in preparing the compounds of the invention.

Examples 164 to 168 illustrate the activity of the compounds of the invention against various pests.

Unless otherwise specified, the group X at position 23 always represents a hydrogen atom, throughout all of the Examples. Examples 1 to 94 illustrate the preparation of compounds of formula (Ia) from starting materials of formula (III), by the reaction of Step A in the above Reaction Scheme No. 1.

EXAMPLE 1

13-p-Fluorophenoxyacetoxy-5-keto-25-ethylmilbemycin 5-oxime (Compound of formula (Ia) wherein: $R^1$=ethyl, $R^5$=p-fluorophenoxymethyl, n=0).

A solution of 121 mg of 13-p-fluorophenoxyacetoxy-5-keto-25-ethylmilbemycin in a mixture of 4 ml of methanol and 4 ml of dioxane was added dropwise to 3 ml of an aqueous solution containing 59 mg of hydroxylamine hydrochloride, and the resulting mixture was stirred at room temperature for 8 hours. After completion of the reaction, the mixture was poured into water and extracted with ethyl acetate. The ethyl acetate extracts were washed with saturated aqueous sodium chloride solution, dried over anhydrous sodium sulfate, and then concentrated. The residue was subjected to column chromatography over silica gel, giving 76 mg of the target product (yield: 61.8 %).

Mass Spectrum (m/z): 709(M+), 675.

Nuclear Magnetic Resonance Spectrum (270 MHz, CDCl$_3$) δ ppm: 3.97 (1H, singlet, OH at the 7 position); 4.67 (1H, singlet, H at the 6 position); 5.06 (1H, doublet, H at the 13 position, J=10.6 Hz).

By following the procedure of Example 1, the compounds of the following Examples 2 to 94 were obtained, having the characteristics shown.

EXAMPLE 2

13-Ethoxycarbonyloxy-5-keto-25-isopropylmilbemycin 5-oxime (Compound of formula (Ia) wherein: $R^1$=isopropyl, $R^5$=ethyl, n=1).

Mass Spectrum (m/z): 657(M+), 639.

Nuclear Magnetic Resonance Spectrum (270 MHz, CDCl$_3$) δ ppm: 3.94 (1H, singlet, OH at the 7 position); 4.46 (1H, singlet, H at the 6 position); 4.49 (1H, doublet, H at the 13 position, J=11.7 Hz).

EXAMPLE 3

13-Acetoxy-5-keto-25-isopropylmilbemycin 5-oxime (Compound of formula (Ia) wherein: $R^1$=isopropyl, $R^5$=methyl, n=0).

Mass Spectrum (m/z): 618(M+).

Nuclear Magnetic Resonance Spectrum (270 MHz, CDCl$_3$) δ ppm: 3.92 (1H, singlet, OH at the 7 position); 4.66 (1H, singlet, H at the 6 position); 4.95 (1H, doublet, H at the 13 position, J=10.8 Hz).

EXAMPLE 4

13-p-Chlorobenzoyloxy-5-keto-25-ethylmilbemycin 5-oxime (Compound of formula (Ia) wherein: $R^1$=ethyl, $R^5$=p-chlorophenyl, n=0).

Mass Spectrum (m/z): 709(M+), 675.

Nuclear Magnetic Resonance Spectrum (270 MHz, CDCl$_3$) δ ppm: 3.97 (1H, singlet, OH at the 7 position); 4.70 (1H, singlet, H at the 6 position); 5.20 (1H, doublet, H at the 13 position, J=10.6 Hz).

EXAMPLE 5

13-p-t-Butylbenzoyloxy-5-keto-25-ethylmilbemycin 5-oxime (Compound of formula (Ia) wherein: $R^1$=ethyl, $R^5$=p-t-butylphenyl, n=0).

Mass Spectrum (m/z): 731(M+), 713, 553.

Nuclear Magnetic Resonance Spectrum (270 MHz, CDCl$_3$) δ ppm: 3.98 (1H, singlet, OH at the 7 position); 4.69 (1H, singlet, H at the 6 position); 5.19 (1H, doublet, H at the 13 position, J=10.6 Hz).

EXAMPLE 6

13-o-Trifluoromethylbenzoyloxy-5-keto-25-ethylmilbemycin 5-oxime (Compound of formula (Ia) wherein: $R^1$=ethyl, $R^5$=o-trifluoromethylphenyl, n=0).

Mass Spectrum (m/z): 743(M+), 725, 709.

Nuclear Magnetic Resonance Spectrum (270 MHz, CDCl$_3$) δ ppm: 3.98 (1H, singlet, OH at the 7 position); 4.68 (1H, singlet, H at the 6 position); 5.23 (1H, doublet, H at the 13 position, J=10.3 Hz).

EXAMPLE 7

13-(2-Furoyloxy)-5-keto-25-ethylmilbemycin 5-oxime (Compound of formula (Ia) Wherein; $R^1$=ethyl, $R^5$=2-furyl, n=0).

Mass Spectrum (m/z): 665(M+), 647, 631.

Nuclear Magnetic Resonance Spectrum (270 MHz, CDCl$_3$) δ ppm: 3.96 (1H, singlet, OH at the 7 position); 4.68 (1H, singlet, H at the 6 position); 5.17 (1H, doublet, H at the 13 position, J=10.6 Hz).

EXAMPLE 8

13-Benzyloxycarbonyloxy-5-keto-25-ethylmilbemycin 5-oxime (Compound of formula (Ia) wherein: $R^1$=ethyl, $R^5$=benzyl, n=1).

Mass Spectrum (m/z): 705(M+), 553.

Nuclear Magnetic Resonance Spectrum (270 MHz, CDCl$_3$) δ ppm: 3.96 (1H, singlet, OH at the 7 position); 4.67 (1H, singlet, H ar the 6 position); 4.76 (1H, doublet, H at the 13 position, J=10.3 Hz).

EXAMPLE 9

13-Methoxycarbonyloxy-5-keto-25-ethylmilbemycin and -25-methylmilbemycin 5-oxime (mixture of two compounds in the ratio 8:2)

(Compound of formula (Ia) wherein: $R^1$=ethyl or methyl, $R^5$=methyl, n=1).

Mass Spectrum (m/z): 629(M+).

Nuclear Magnetic Resonance Spectrum (270 MHz, CDCl$_3$) δ ppm: 3.97 (1H, singlet, OH at the 7 position); 4.67 (1H, singlet, H at the 6 position); 4.7–4.85 (3H, multiplet, CH$_2$ at the 27 position, H at the 13 position).

EXAMPLE 10

13-(2,2,2-Trichloroethoxycarbonyloxy)-5-keto-25-ethylmilbemycin 5-oxime (Compound of formula (Ia) wherein: $R^1$=ethyl, $R^5$=2,2,2-trichloroethyl, n=1).

Mass Spectrum (m/z): 745(M+), 727.

Nuclear Magnetic Resonance Spectrum (270 MHz, CDCl$_3$) δ ppm: 3.97 (1H, singlet, OH at the 7 position); 4.67 (1H, singlet, H at the 6 position); 4.80 (1H, doublet, H at the 13 position, J=10.3 Hz).

EXAMPLE 11

13-(2-Butenoyloxy)-5-keto-25-ethylmilbemycin and -25-methylmilbemycin 5-oxime (mixture of two compounds in the ratio 2.6:1)

(compound of formula (Ia) wherein: R$^1$=ethyl or methyl, R$^5$=propenyl, n=0).

Mass Spectrum (m/z): 639(M+).

Nuclear Magnetic Resonance Spectrum (270 MHz, CDCl$_3$) δ ppm: 3.95 (1H, singlet, OH at the 7 position); 4.67 (1H, singlet, H at the 6 position); 5.01 (1H, doublet, H at the 13 position, J=10.6 Hz).

EXAMPLE 12

13-[2-(2,2-Dichlorovinyl)-3,3-dimethylcycloproylcarbonyloxy]-5-keto-25-ethylmilbemycin and -25-methylmilbemycin 5-oxime (mixture of two compounds in the ratio 2.6:1)

(Compound of formula (Ia) wherein: R$^1$=ethyl or methyl, R$^5$=2-(2,2-dichlorovinyl)-3,3-dimethylcyclopropyl, n=0).

Mass Spectrum (m/z): 761(M+).

Nuclear Magnetic Resonance Spectrum (270 MHz, CDCl$_3$) δ ppm: 3.97 (1H, singlet, OH at the 7 position); 4.67 (1H, singlet, H at the 6 position); 5.40 (1H, doublet, H at the 13 position, J=11 Hz).

EXAMPLE 13

13-phenylacetoxy-5-keto-25-ethylmilbemycin and -25-methylmilbemycin 5-oxime (mixture of two compounds in the ratio 2.8:1)

(Compound of formula (Ia) wherein: R$^1$=ethyl or methyl, R$^5$=benzyl, n=0).

Mass Spectrum (m/z): 689(M+), 655.

Nuclear Magnetic Resonance Spectrum (270 MHz, CDCl$_3$) δ ppm: 3.95 (1H, singlet, OH at the 7 position); 4.66 (1H, singlet, H at the 6 position); 4.93 (1H, doublet, H at the 13 position, J=10.6 Hz).

EXAMPLE 14

13-[2-Hydroxy-3-(t-butyldimethylsiloxy)propoxycarbonyloxy]-5-keto-25-ethylmilbemycin and -25-methylmilbemycin 5-oxime (mixture of two compounds in the ratio 3.4:1)

(Compound of formula (Ia) wherein: R$^1$=ethyl or methyl, R$^5$=2-hydroxy-3-(t-butyldimethylsiloxy)propyl, n=1).

Mass Spectrum (m/z): 803(M+).

Nuclear Magnetic Resonance Spectrum (270 MHz, CDCl$_3$) δ ppm: 3.97 (1H, singlet, OH ar the 7 position); 4.67 (1H, singlet, H at the 6 position); 4.74 (1H, doublet, H at the 13 position, J=9.7 Hz).

EXAMPLE 15

13-(2,2-Dimethyl-1,3-dioxolanylmethoxycarbonyloxy)-5-keto-25-ethylmilbemycin and -25-methylmilbemycin 5-oxime mixture of two compounds in the ratio 2.3:1

(Compound of formula (Ia) wherein: R$^1$=ethyl or methyl, R$^5$=2,2-dimethyl-1,3-dioxolanylmethyl, n=1).

Mass Spectrum (m/z): 729 and 715(M+).

Nuclear Magnetic Resonance Spectrum (270 MHz, CDCl$_3$) δ ppm: 3.97 (1H, singlet, OH at the 7 position); 4.69 (1H, singlet, H at the 6 position); 4.65–4.85 (3H, multiplet, CH$_2$ at the 27 position, H at the 13 position).

EXAMPLE 16

13-(2,3-Dihydroxypropoxycarbonyloxy)-5-keto-25-ethylmilbemycin and -25-methylmilbemycin 5-oxime (mixture of two compounds in the ratio 2.3:1)

(Compound of formula (Ia) wherein: R$^1$=ethyl or methyl, R$^5$=2,3-dihydroxypropyl, n=1).

Mass Spectrum (m/z): 689 and 675(M+).

Nuclear Magnetic Resonance Spectrum (270 MHz, CDCl$_3$) δ ppm: 3.96 (1H, singlet, OH at the 7 position); 4.67 (1H, singlet, H at the 6 position); 4.74 (1H, doublet, H at the 13 position, J=10.3 Hz).

EXAMPLE 17

13-(3-Chloropropionyloxy)-5-keto-25-ethylmilbemycin and -25-methylmilbemycin 5-oxime (mixture of two compounds in the ratio 2.7:1)

(Compound of formula (Ia) wherein: R$^1$=ethyl or methyl, R$^5$=2-chloroethyl, n=0).

Mass Spectrum (m/z): 662(M+).

Nuclear Magnetic Resonance Spectrum (270 MHz, CDCl$_3$) δ ppm: 3.96 (1H, singlet, OH at the 7 position); 4.67 (1H, singlet, H ar the 6 position); 5.00 (1H, doublet, H at the 13 position, J=10.6 Hz).

EXAMPLE 18

13-(2-Methoxyethoxycarbonyloxy)-5-keto-25-ethylmilbemycin 5-oxime (Compound of formula (Ia) wherein: R$^1$=ethyl, R$^5$=2-methoxyethyl, n=1).

Mass Spectrum (m/z): 673(M+), 655, 640.

Nuclear Magnetic Resonance Spectrum (270 MHz, CDCl$_3$) δ ppm: 3.95 (1H, singlet, OH at the 7 position); 4.67 (1H, singlet, H at the 6 position); 4.75 (1H, doublet, H at the 13 position, J=10.6 Hz).

EXAMPLE 19

13-Pivaloyloxy-5-keto-25-ethylmilbemycin 5-oxime (Compound of formula (Ia) wherein: R$^1$=ethyl, R$^5$=t-butyl, n=0).

Mass Spectrum (m/z): 655(M+), 637, 621.

Nuclear Magnetic Resonance Spectrum (270 MHz, CDCl$_3$) δ ppm: 3.97 (1H, singlet, OH at the 7 position); 4.66 (1H, singlet, H at the 6 position); 4.91 (1H, doublet, H at the 13 position, J=10.2 Hz).

EXAMPLE 20

13-Trichloroacetoxy-5-keto-25-ethylmilbemycin 5-oxime (Compound of formula (Ia) wherein: R$^1$=ethyl, R$^5$=trichloromethyl, n=0).

Mass Spectrum (m/z): 715(M+), 697.

Nuclear Magnetic Resonance Spectrum (270 MHz, CDCl$_3$) δ ppm: 3.96 (1H, singlet, OH at the 7 position); 4.68 (1H, singlet, H at the 6 position); 4.99 (1H, doublet, H at the 13 position, J=10.6 Hz).

EXAMPLE 21

13-Iodoacetoxy-5-keto-25-ethylmilbemycin 5-oxime (Compound of formula (Ia) wherein: R$^1$=ethyl, R$^5$=iodomethyl, n=0).

Mass Spectrum (m/z): 739(M+), 721.

Nuclear Magnetic Resonance Spectrum (270 MHz, CDCl$_3$) δ ppm: 3.97 (1H, singlet, OH at the 7 position); 4.66 (1H, singlet, H at the 6 position); 4.94 (1H, doublet, H at the 13 position, J=10.8 Hz).

EXAMPLE 22

13-Formyloxy-5-keto-25-ethylmilbemycin 5-oxime (Compound of formula (Ia) wherein: $R^1$=ethyl, $R^5$=hydrogen, n=0).

Mass Spectrum (m/z): 599(M+), 585, 581.

Nuclear Magnetic Resonance Spectrum (270 MHz, CDCl$_3$) δ ppm: 3.97 (1H, singlet, OH at the 7 position); 4.68 (1H, singlet, H at the 6 position); 5.05 (1H, doublet, H at the 13 position, J=10.6 Hz).

EXAMPLE 23

13-p-Bromobenzoyloxy-5-keto-25-ethylmilbemycin 5-oxime (Compound of formula (Ia) wherein: $R^1$=ethyl, $R^5$=p-bromophenyl, n=0).

Mass Spectrum (m/z): 753(M+, with Br$^{79}$), 735, 719.

Nuclear Magnetic Resonance Spectrum (270 MHz, CDCl$_3$) δ ppm: 3.98 (1H, singlet, OH at the 7 position); 4.69 (1H, singlet, H at the 6 position); 5.19 (1H, doublet, H at the 13 position, J=10.4 Hz).

EXAMPLE 24

13-Cyclobutylcarbonyloxy-5-keto-25-ethylmilbemycin 5-oxime (Compound of formula (Ia) wherein: $R^1$=ethyl, $R^5$=cycloburyl, n=0).

Mass Spectrum (m/z): 653(M+).

Nuclear Magnetic Resonance Spectrum (270 MHz, CDCl$_3$) δ ppm: 3.95 (1H, singlet, OH at the 7 position); 4.67 (1H, singlet, H at the 6 position); 4.94 (1H, doublet, H at the 13 position, J=10.6 Hz).

EXAMPLE 25

13-o-Chlorobenzoyloxy-5-keto-25-ethylmilbemycin and -25-methylmilbemycin 5-oxime (mixture of two compounds in the ratio 2.3:1)

(Compound of formula (Ia) wherein: $R^1$=ethyl or methyl, $R^5$=o-chlorophenyl, n=0).

Mass Spectrum (m/z): 709(M+).

Nuclear Magnetic Resonance Spectrum (270 MHz, CDCl$_3$) δ ppm: 3.97 (1H, singlet, OH at the 7 position); 4.67 (1H, singlet, H at the 6 position); 5.23 (1H, doublet, H at the 13 position, J=10.6 Hz).

EXAMPLE 26

13-(2,4-Dichlorobenzoyloxy)-5-keto-25-ethylmilbemycin and -25-methylmilbemycin 5-oxime (mixture of two compounds in the ratio 2.3:1)

(Compound of formula (Ia) wherein: $R^1$=ethyl or methyl, $R^5$=2,4-dichlorophenyl, n=0).

Mass Spectrum (m/z): 743(M+).

Nuclear Magnetic Resonance Spectrum (270 MHz, CDCl$_3$) δ ppm: 3.98 (1H, singlet, OH at the 7 position); 4.66 (1H, singlet, H at the 6 position); 5.23 (1H, doublet, H at the 13 position, J=10.6 Hz).

EXAMPLE 27

13-m-Fluorobenzoyloxy-5-keto-25-ethylmilbemycin and -25-methylmilbemycin 5-oxime (mixture of two compounds in the ratio 2.3:1)

(Compound of formula (Ia) wherein: $R^1$=ethyl or methyl, $R^5$=m-fluorophenyl, n=0).

Mass Spectrum (m/z): 693(M+).

Nuclear Magnetic Resonance Spectrum (270 MHz, CDCl$_3$) δ ppm: 3.71 (1H, singlet, OH at the 7 position); 4.69 (1H, singlet, H at the 6 position); 5.21 (1H, doublet, H at the 13 position, J=10.6 Hz).

EXAMPLE 28

13-m-Trifluoromethylbenzoyloxy-5-keto-25-ethylmilbemycin and -25-methylmilbemycin 5-oxime (mixture of two compounds in the ratio 2.3:1)

(Compound of formula (Ia) wherein: $R^1$=ethyl or methyl, $R^5$=m-trifluoromethylphenyl, n=0).

Mass Spectrum (m/z): 743(M+).

Nuclear Magnetic Resonance Spectrum (270 MHz, CDCl$_3$) δ ppm: 4.0 (1H, singlet, OH at the 7 position); 4.69 (1H, singlet, H at the 6 position); 5.24 (1H, doublet, H at the 13 position, J=10.3 Hz).

EXAMPLE 29

13-(2,5-Dichloro-6-methoxybenzoyloxy)-5-keto-25-ethylmilbemycin and -25-methylmilbemycin 5-oxime (mixture of two compounds in the ratio 2.3:1)

(Compound of formula (Ia) wherein: $R^1$=ethyl or methyl, $R^5$=2,5-dichloro-6-methoxyphenyl, n=0).

Mass Spectrum (m/z): 773(M+).

Nuclear Magnetic Resonance Spectrum (270 MHz, CDCl$_3$) δ ppm: 3.90 (1H, singlet, OH at the 7 position); 4.69 (1H, singlet, H at the 6 position); 5.20 (1H, doublet, H at the 13 position, J=10.6 Hz).

EXAMPLE 30

13-Cyclohexylcarbonyloxy-5-keto-25-ethylmilbemycin and -25-methylmilbemycin 5-oxime (mixture of two compounds in the ratio 2.3:1)

(Compound of formula (Ia) wherein: $R^1$=ethyl or methyl, $R^5$=cyclohexyl, n=0).

Mass Spectrum (m/z): 681(M+).

Nuclear Magnetic Resonance Spectrum (270 MHz, CDCl$_3$) δ ppm: 3.90 (1H, singlet, OH at the 7 position); 4.68 (1H, singlet, H at the 6 position); 4.93 (1H, doublet, H at the 13 position, J=10.6 Hz).

EXAMPLE 31

13-(2-Phenylpropionyloxy)-5-keto-25-ethylmilbemycin and -25-methylmilbemycin 5-oxime (mixture of two compounds in the ratio 2.3:1)

(Compound of formula (Ia) wherein: $R^1$=ethyl or methyl, $R^5$=α-methylbenzyl, n=0).

Mass Spectrum (m/z): 703(M+).

Nuclear Magnetic Resonance Spectrum (270 MHz, CDCl$_3$) δ ppm: 3.98 (1H, singlet, OH at the 7 position); 4.66 (1H, singlet, H at the 6 position); 4.89 (1H, doublet, H at the 13 position, J=10.6 Hz).

EXAMPLE 32

13-o-Bromobenzoyloxy-5-keto-25-ethylmilbemycin 5-oxime (Compound of formula (Ia) wherein: $R^1$=ethyl, $R^5$=o-bromophenyl, n=0).

Mass Spectrum (m/z): 753(M+, with Br$^{79}$).

Nuclear Magnetic Resonance Spectrum (270 MHz, CDCl$_3$) δ ppm: 3.71 (1H, singlet, OH at the 7 position); 4.68 (1H, singlet, H at the 6 position); 4.94 (1H, doublet, H at the 13 position, J=10.6 Hz).

EXAMPLE 33

13-(2,2-Dichloropropionyloxy)-5-keto-25-ethylmilbemycin and -25-methylmilbemycin 5-oxime (mixture of two compounds in the ratio 2.3:1)

(Compound of formula (Ia) wherein: $R^1$=ethyl or methyl, $R^5$=1,1-dichloroethyl, n=0).

Mass Spectrum (m/z): 695(M+).

Nuclear Magnetic Resonance Spectrum (270 MHz, $CDCl_3$) δ ppm: 3.95 (1H, singlet, OH at the 7 position); 4.68 (1H, singlet, H at the 6 position); 4.95 (1H, doublet, H at the 13 position, J=10.3 Hz).

EXAMPLE 34

13-Cyclopropylcarbonyloxy-5-keto-25-ethylmilbemycin 5-oxime (Compound of formula (Ia) wherein: $R^1$=ethyl, $R^5$=cyclopropyl, n=0).

Mass Spectrum (m/z): 639(M+).

Nuclear Magnetic Resonance Spectrum (270 MHz, $CDCl_3$) δ ppm: 3.90 (1H, singlet, OH at the 7 position); 4.57 (1H, singlet, H at the 6 position); 4.98 (1H, doublet, H at the 13 position, J=10.6 Hz).

EXAMPLE 35

13-(1-Methylcyclohexylcarbonyloxy)-5-keto-25-ethylmilbemycin and -25-methylmilbemycin 5-oxime (mixture of two compounds in the ratio 2.3:1)

(Compound of formula (Ia) wherein: $R^1$=ethyl or methyl, $R^5$=1-methylcyclohexyl, n=0).

Mass Spectrum (m/z): 695(M+).

Nuclear Magnetic Resonance Spectrum (270 MHz, $CDCl_3$) δ ppm: 3.97 (1H, singlet, OH at the 7 position); 4.67 (1H, singlet, H at the 6 position); 4.94 (1H, doublet, H at the 13 position, J=10.6 Hz).

EXAMPLE 36

13-Octanoyloxy-5-keto-25-ethylmilbemycin and -25-methylmilbemycin 5-oxime (mixture of two compounds in the ratio 2.3:1)

(Compound of formula (Ia) wherein: $R^1$=ethyl or methyl, $R^5$=heptyl, n=0).

Mass Spectrum (m/z): 697(M+).

Nuclear Magnetic Resonance Spectrum (270 MHz, $CDCl_3$) δ ppm: 3.96 (1H, singlet, OH at the 7 position); 4.68 (1H, singlet, H at the 6 position); 4.95 (1H, doublet, H at the 13 position, J=10.2 Hz).

EXAMPLE 37

13-Palmitoyloxy-5-keto-25-ethylmilbemycin and -25-methylmilbemycin 5-oxime (mixture of two compounds in the ratio 2.3:1)

(Compound of formula (Ia) wherein: $R^1$ethyl or methyl, $R^5$=pentadecyl, n=0).

Mass Spectrum (m/z): 809(M+).

Nuclear Magnetic Resonance Spectrum (270 MHz, $CDCl_3$) δ ppm: 3.95 (1H, singlet, OH at the 7 position); 4.68 (1H, singlet, H at the 6 position); 4.96 (1H, doublet, H at the 13 position, J=10.3 Hz).

EXAMPLE 38

13-Isonicotinyloxy-5-keto-25-ethylmilbemycin 5-oxime (Compound of formula (Ia) wherein: $R^1$=ethyl, $R^5$=4-pyridyl, n=0).

Mass Spectrum (m/z): 676(M+).

Nuclear Magnetic Resonance Spectrum (270 MHz, $CDCl_3$) δ ppm: 4.01 (1H, singlet, OH at the 7 position); 4.70 (1H, singlet, H at the 6 position); 5.22 (1H, doublet, H at the 13 position, J=10.6 Hz).

EXAMPLE 39

13-m-Toluoyl-5-keto-25-ethylmilbemycin and -25-methylmilbemycin 5-oxim (mixture of two compounds in the ratio 2.3:1)

(Compound of formula (Ia) wherein: $R^1$=ethyl or methyl, $R^5$=m-tolyl, n=0).

Mass Spectrum (m/z): 689(M+).

Nuclear Magnetic Resonance Spectrum (270 MHz, $CDCl_3$) δ ppm: 3.99 (1H, singlet, OH at the 7 position); 4.69 (1H, singlet, H at the 6 position); 5.21 (1H, doublet, H at the 13 position, J=10.3 Hz).

EXAMPLE 40

13-Pentafluorobenzoyloxy-5-keto-25-ethylmilbemycin and -25-methylmilbemycin 5-oxime (mixture of two compounds in the ratio 2.3:1)

(Compound of formula (Ia) wherein: $R^1$=ethyl or methyl, $R^5$=pentafluorophenyl, n=0).

Mass Spectrum (m/z): 765(M+).

Nuclear Magnetic Resonance Spectrum (270 MHz, $CDCl_3$) δ ppm: 3.97 (1H, singlet, OH at the 7 position); 4.68 (1H, singlet, H at the 6 position); 5.21 (1H, doublet, at the 13 position, J=10.6 HZ).

EXAMPLE 41

13-(3-Adamantylcarbonyloxy)-5-keto-25-ethylmilbemycin 5-oxime (Compound of formula (Ia) wherein: $R^1$=ethyl, $R^5$=3-adamantyl, n=0).

Mass Spectrum (m/Z): 733(M+).

Nuclear Magnetic Resonance Spectrum (270 MHz, $CDCl_3$) δ ppm; 3.95 (1H, singlet, OH at the 7 position); 4.67 (1H, singlet, H at the 6 position); 4.92 (1H, doublet, H at the 13 position, J=10.6 Hz).

EXAMPLE 42

13-[3,5-Bis(trifluoromethyl)benzoyloxy]-5-keto-25-ethylmilbemycin 5-oxime (Compound of formula (Ia) Wherein: $R^1$=ethyl, $R^5$=3,5-bis(trifluoromethyl)phenyl, n=0).

Mass Spectrum (m/z): 811(M+).

Nuclear Magnetic Resonance Spectrum (270 MHz, $CDCl_3$) δ ppm: 3.97 (1H, singlet, OH at the 7 position); 4.69 (1H, singlet, H at the 6 position); 5.26 (1H, doublet, H at the 13 position, J=10.6 Hz).

EXAMPLE 43

13-(2-Thenoyloxy)-5-keto-25-ethylmilbemycin and -25-methylmilbemycin 5-oxime (mixture of two compounds in the ratio 1.2:1)

(Compound of formula (Ia) wherein: $R^1$=ethyl or methyl, $R^5$=2-thienyl, n=0).

Mass Spectrum (m/z): 681(M+).

Nuclear Magnetic Resonance Spectrum (270 MHz. $CDCl_3$) δ ppm: 3.97 (1H, singlet, OH at the 7 position); 4.68 (1H, singlet, H at the 6 position); 5.14 (1H, doublet, H at the 13 position, J=10.6 Hz).

EXAMPLE 44

13-(2,6-Difluorobenzoyloxy)-5-keto-25-ethylmilbemycin and -25-methylmilbemycin 5-oxime (mixture of two compounds in the ratio 2.6:1)

(Compound of formula (Ia) wherein: $R^1$=ethyl or methyl, $R^5$=2,6-difluorophenyl, n=0).

Mass Spectrum (m/z): 711(M+).

Nuclear Magnetic Resonance Spectrum (270 MHz, $CDCl_3$) δ ppm: 3.98 (1H, singlet, OH at the 7 position); 4.68 (1H, singlet, H at the 6 position); 5.21 (1H, doublet, H at the 13 position, J=10.6 Hz).

EXAMPLE 45

13-Chloropiyaloyloxy-5-keto-25-ethylmilbemycin and -25-methylmilbemycin 5-oxime (mixture of two compounds in the ratio 2.3:1)

(Compound of formula (Ia) wherein: $R^1$=ethyl or methyl, $R^5$=1,1-dimethyl-2-chloroethyl, n=0).

Mass Spectrum (m/z): 689(M+).

Nuclear Magnetic Resonance Spectrum (270 MHz, $CDCl_3$) δ ppm: 3.96 (1H, singlet, OH at the 7 position); 4.67 (1H, singlet, H at the 6 position); 4.95 (1H, doublet, H at the 13 position, J=10.6 Hz).

EXAMPLE 46

13-(1-Methylcyclopropylcarbonyloxy)-5-keto-25-ethylmilbemycin 5-oxime (Compound of formula (Ia) wherein: $R^1$=ethyl, $R^5$1-methylcyclopropyl, n=0).

Mass Spectrum (m/z): 653(M+).

Nuclear Magnetic Resonance Spectrum (270 MHz, $CDCl_3$) δ ppm: 3.96 (1H, singlet, OH at the 7 position); 4.67 (1H, singlet, H at the 6 position); 4.95 (1H, doublet, H at the 13 position, J=10.6 Hz).

EXAMPLE 47

13-(α,α-Dimethylbenzoyloxy-5-keto-25-ethylmilbemycin 5-oxime (Compound of formula (Ia) wherein: $R^1$=ethyl, $R^5$=α,α-dimethylbenzyl, n=0).

Mass Spectrum (m/z): 717(M+).

Nuclear Magnetic Resonance Spectrum (270 MHz, $CDCl_3$) δ ppm: 3.96 (1H, singlet, OH at the 7 position); 4.65 (1H, singlet, H at the 6 position); 4.87 (1H, doublet, H at the 13 position, J=10.3 Hz).

EXAMPLE 48

13-o-Acetoxybenzoyloxy-5-keto-25-ethylmilbemycin 5-oxime (Compound of formula (Ia) wherein: $R^1$=ethyl, $R^5$=o-acetoxyphenyl, n=0).

Mass Spectrum (m/z): 699(M+ −34).

Nuclear Magnetic Resonance Spectrum (270 MHz, $CDCl_3$) δ ppm: 3.8 (1H, broad singlet, OH at the 7 position); 4.68 (1H, singlet, H at the 6 position); 5.18 (1H, doublet H at the 13 position, J=10.6 Hz).

EXAMPLE 49

13-Methoxycarbonylacetoxy-5-keto-25-ethylmilbemycin 5-oxime (Compound of formula (Ia) wherein: $R^1$=ethyl, $R^5$=methoxycarbonylmethyl, n=0).

Mass Spectrum (m/z): 671(M+), 653, 629.

Nuclear Magnetic Resonance Spectrum (270 MHz, $CDCl_3$) δ ppm: 3.96 (1H, singlet, OH at the 7 position); 5.02 (1H, doublet, H at the 13 position, J=10.7 Hz).

EXAMPLE 50

13-t-Butoxycarbonylacetoxy-5-keto-25-ethylmilbemycin 5-oxime (Compound of formula (Ia) wherein: $R^1$=ethyl, $R^5$=t-butoxycarbonylmethyl, n=0).

Mass Spectrum (m/z): 713(M+), 695, 679.

Nuclear Magnetic Resonance Spectrum (270 MHz, $CDCl_3$) δ ppm: 3.96 (1H, singlet, OH at the 7 position); 5 00 (1H, doublet, H at the 13 position, J=10.6 Hz).

EXAMPLE 51

13-(3-Fluoro-2,2-dimethylpropionyloxy)-5-keto-25-ethylmilbemycin 5-oxime (Compound of formula (Ia) wherein: $R^1$=ethyl, $R^5$=2-fluoro-1,1-dimethylethyl, n=0).

Mass Spectrum (m/z): 658, 640, 538, 520.

Nuclear Magnetic Resonance Spectrum (270 MHz, $CDCl_3$) δ ppm: 4.67 (1H, singlet, H at the 6 position); 4.95 (1H, doublet, H at the 13 position, J=10.3 Hz).

EXAMPLE 52

13-p-(Trifluoromethyl)benzoyloxy-5-keto-25-ethylmilbemycin 5-oxime (Compound of formula (Ia) wherein: $R^1$=ethyl, $R^5$=p-(trifluoromethyl)phenyl, n=0).

Mass Spectrum (m/z): 743(M+), 725, 709, 553.

Nuclear Magnetic Resonance Spectrum (270 MHz, $CDCl_3$) δ ppm: 4.69 (1H, singlet, H at the 6 position); 5.23 (1H, doublet, H at the 13 position, J=10.6 Hz).

EXAMPLE 53

13-(3,3,3-Trifluoropropionyloxy)-5-keto-25-ethylmilbemycin 5-oxime (Compound of formula (Ia) wherein: $R^1$=ethyl, $R^5$=2,2,2-trifluoroethyl, n=0).

Mass Specttum (m/z): 681(M+), 663, 647.

Nuclear Magnetic Resonance Spectrum (270 MHz, $CDCl_3$) δ ppm: 4.67 (1H, singlet, H at the 6 position); 5.02 (1H, doublet, H at the 13 position, J=10.6 Hz).

EXAMPLE 54

13-p-Nitrobenzoyloxy-5-keto-25-ethylmilbemycin 5-oxime (Compound of formula (Ia) wherein: $R^1$=ethyl, $R^5$=p-nitrophenyl, n=0).

Mass Spectrum (m/z): 720(M+), 702, 589, 553, 519.

Nuclear Magnetic Resonance Spectrum (270 MHz, $CDCl_3$) δ ppm: 4.69 (1H, singlet, H at the 6 position); 5.23 (1H, doublet, H at the 13 position, J TM 10.9 Hz).

EXAMPLE 55

13-p-Phenoxybenzoyloxy-5-keto-25-ethylmilbemycin 5-oxime (Compound of formula (Ia) wherein: $R^1$=ethyl, $R^5$=o-phenoxyphenyl, n=0).

Mass Spectrum (m/z): 767(M+), 733, 707, 553, 519.

Nuclear Magnetic Resonance Spectrum (270 MHz, $CDCl_3$) δ ppm: 4.68 (1H, singlet, H at the 6 position); 5.14 (1H, doublet, H at the 13 position, J=10.3 Hz).

EXAMPLE 56

13-(2,6-Dimethylbenzoyloxy)-5-keto-25-ethylmilbemycin 5-oxime (Compound of formula (Ia) wherein: $R^1$=ethyl, $R^5$=2,6-xylyl, n=0).

Mass Spectrum (m/z): 703(M+), 685, 669, 645, 553, 536.

Nuclear Magnetic Resonance Spectrum (270 MHz, CDCl$_3$) δ ppm: 4.68 (1H, singlet, H at the 6 position); 5.26 (1H, doublet, H at the 13 position, J=10.3 Hz).

EXAMPLE 57

13-(2,4,6-Trimethylbenzoyloxy)-5-keto-25-ethylmilbemycin 5-oxime (Compound of formula (Ia) wherein: $R^1$=ethyl, $R^5$=mesityl, n=0).

Mass Spectrum (m/z): 717(M+), 699, 683, 519.

Nuclear Magnetic Resonance Spectrum (270 MHz, CDCl$_3$) δ ppm: 4.68 (1H, singlet, H at the 6 position); 5.25 (1H, doublet, H at the 13 position, J=10.7 Hz).

EXAMPLE 58

13-m-Phenoxybenzoyloxy-5-keto-25-ethylmilbemycin 5-oxime (Compound of formula (Ia) wherein: $R^1$=ethyl, $R^5$=m-phenoxyphenyl, n=0).

Mass Spectrum (m/z): 767(M+), 749, 733, 553, 535, 519.

Nuclear Magnetic Resonance Spectrum (270 MHz, CDCl$_3$) δ ppm: 4.68 (1H, singlet, H at the 6 position); 5.18 (1H, doublet, H at the 13 position, J=10.6 Hz).

EXAMPLE 59

13-(2,5,7,8-Tetramethyl-6-methoxy-2-chromanylcarbonyloxy)-5-keto-25-ethylmilbemycin 5-oxime (Compound of formula (Ia) wherein: $R^1$=ethyl, $R^5$=2,5,7,8-tetramethyl-6-methoxy-2-chromanyl, n=0).

Mass Spectrum (m/z): 817(M+), 799, 783, 589, 571.

Nuclear Magnetic Resonance Spectrum (270 MHz, CDCl$_3$) δ ppm: 4.65–4.85 (5H, multiplet).

EXAMPLE 60

13-(9-Fluorenylcarbonyloxy)-5-keto-25-ethylmilbemycin 5-oxime (Compound of formula (Ia) wherein: $R^1$=ethyl, $R^5$=9-fluorenyl, n=0).

Mass Spectrum (m/z): 763(M+), 745.

Nuclear Magnetic Resonance Spectrum (270 MHz, CDCl$_3$) δ ppm: 4.67 (1H, singlet, H at the 6 position); 4.80 (1H, doublet, H at the 13 position, J=10.4 Hz).

EXAMPLE 61

13-(2,3-Dihydro-3-oxopyrido-[2,1-c]-1,2,4-triazol-2-yl-carbonyloxy)-5-keto-25-ethylmilbemycin 5-oxime (Compound of formula (Ia) wherein: $R^1$=ethyl, $R^5$=2,3-dihydro-3-oxopyrido-[2,1-c]-1,2,4-triazol-2-yl, n=0).

Mass Spectrum (m/z): 688(M+−44), 676, 571, 553, 537, 519.

Nuclear Magnetic Resonance Spectrum 270 MHz, CDCl$_3$) δ ppm: 4.70 (1H, singlet, H at the 6 position); 5.16 (1H, doubler, H at the 13 position, J=10.6 Hz).

EXAMPLE 62

13-(9-Xanthenylcarbonyloxy)-5-keto-25-ethylmilbemycin 5-oxime (Compound of formula (Ia) wherein: $R^1$=ethyl, $R^5$=9-xanthenyl, n=0).

Mass Spectrum (m/z): 779(M+), 761, 745, 701, 553, 535, 519.

Nuclear Magnetic Resonance Spectrum (270 MHz, CDCl$_3$) δ ppm: 4.64 (1H, singlet, H at the 6 position); 4.76 (1H, doublet, H at the 13 position, J=10.3 Hz).

EXAMPLE 63

13-(3-Chloro-2-benzothenoyloxy)-5-keto-25-ethyl-milbemycin 5-oxime (Compound of formula (Ia) wherein: $R^1$=ethyl, $R^5$=3-chloro-2-benzothienyl, n=0).

Mass Spectrum (m/z): 765(M+), 749, 731, 553, 535, 519.

Nuclear Magnetic Resonance Spectrum (270 MHz, CDCl$_3$) δ ppm: 4.69 (1H, singlet, H at the 6 position); 5.22 (1H, doublet, H at the 13 position, J=10.6 Hz).

EXAMPLE 64

13-(2,6-Dichloroisonicotinoyloxy)-5-keto-25-ethyl-milbemycin 5-oxime (Compound of formula (Ia) wherein: $R^1$=ethyl, $R^5$=2,6-dichloro-4-pyridyl, n=0).

Mass Spectrum (m/z): 744(M+), 726, 710, 553, 535, 519.

Nuclear Magnetic Resonance Spectrum (270 MHz, CDCl$_3$) δ ppm: 4.69 (1H, singlet, H at the 6 position); 5.21 (1H, doublet, H at the 13 position, J=10.6 Hz).

EXAMPLE 65

13-(3-Methyl-1-oxa-3-cyclobutylcarbonyloxy)-5-keto-25-ethylmilbemycin 5-oxime (Compound of formula (Ia) wherein: $R^1$=ethyl, $R^5$=3-methyl-1-oxa-3-cyclobutyl, n=0).

Mass Spectrum (m/z): 669(M+) 651, 635.

Nuclear Magnetic Resonance Spectrum (270 MHz, CDCl$_3$) δ ppm: 4.67 (1H, singlet, H at the 6 position); 5.00 (1H, doublet, H at the 13 position, J=10.6 Hz).

EXAMPLE 66

13-(2-Ethylthionicotinoyloxy)-5-keto-25-ethylmilbemycin 5-oxime (Compound of formula (Ia) wherein: Rhu 1=ethyl, $R^5$=2-ethylthio-3-pyridyl, n=0).

Mass Spectrum (m/z): 736(M+), 720, 702, 553, 535, 519.

Nuclear Magnetic Resonance Spectrum (270 MHz, CDCl$_3$) δ ppm: 4.69 (1H, singlet, H at the 6 position); 5.22 (1H, doublet, H at the 13 position, J=10.6 Hz).

EXAMPLE 67

13-(3-Phenylpropionyloxy)-5-keto-25-ethylmilbemycin 5-oxime (Compound of formula (Ia) wherein: $R^1$=ethyl, $R^5$=phenethyl, n=0).

Mass Spectrum (m/z): 703(M+), 685, 645, 553, 536, 519.

Nuclear Magnetic Resonance Spectrum (270 MHz, CDCl$_3$) δ ppm: 4.68 (1H, singlet, H at the 6 position); 4.96 (1H, doublet, H at the 13 position, J=10.4 Hz).

EXAMPLE 68

13-Cyclohexylacetoxy-5-keto-25-ethylmilbemycin 5-oxime (Compound of formula (Ia) wherein: $R^1$=ethyl, $R^5$=cyclohexylmethyl, n=0).

Mass Spectrum (m/z): 695(M+), 677, 662, 519.

Nuclear Magnetic Resonance Spectrum (270 MHz, CDCl$_3$) δ ppm: 4.67 (1H, singlet, H at the 6 position); 4.95 (1H, doublet, H at the 13 position, J=10.6 Hz).

EXAMPLE 69

13-{2-[(p-phenoxy)phenoxy]propionyloxy}-5-keto-25-ethylmilbemycin 5-oxime (Compound of formula (Ia) wherein: $R^1$=ethyl, $R^5$=1-[(p-phenoxy)phenoxy]ethyl, n=0).

Mass Spectrum (m/z): 811(M+), 793, 777, 603, 552, 519.

Nuclear Magnetic Resonance Spectrum (270 MHz, CDCl$_3$) δ ppm: 4.67 (1H, singlet, H at the 6 position); 4.96 (1H, doublet, H at the 13 position, J=10.6 Hz).

EXAMPLE 70

13-{2-[p-(5-trifluoromethyl-2-pyridyloxy)phenoxy]propionyloxy}-5-keto-25-ethylmilbemycin 5-oxime (Compound of formula (Ia) wherein: $R^1$=ethyl, $R^5$=1-[p-(5-trifluoromethyl-2-pyridyloxy)phenoxy]ethyl, n=0).

Mass Spectrum (m/z): 880(M+), 537, 368, 327.

Nuclear Magnetic Resonance Spectrum (270 MHz, CDCl$_3$) δ ppm: 4.67 (1H, singlet, M at the 6 position); 4.98 (1H, doublet, H at the 13 position, J=10.6 Hz).

EXAMPLE 71

13-(2-p-Nitrophenylpropionyloxy)-5-keto-25-ethylmilbemycin 5-oxime (Compound of formula (Ia) wherein: $R^1$=ethyl, $R^5$=α-methyl-p-nitrobenzyl, n=0).

Mass Spectrum (m/z): 748(M+), 730, 714, 553, 519.

Nuclear Magnetic Resonance Spectrum (270 MHz, CDCl$_3$) δ ppm: 4.66 (1H, singlet, H at the 6 position); 4.92 (0.5H, doublet, H at the 13 position, J=10.6 Hz); 4.93 (0.5H, doublet, H at the 13 position, J=10.6 Hz).

EXAMPLE 72

13-(2-o-Fluorophenylpropionyloxy)-5-keto-25-ethylmilbemycin 5-oxime (Compound of formula (Ia) wherein: $R^1$=ethyl, $R^5$=α-methyl-o-fluorobenzyl, n=0).

Mass pectrum (m/z): 721(M+), 703, 687.

Nuclear Magnetic Resonance Spectrum (270 MHz, CDCl$_3$) δ ppm: 4.67 (1H, singlet, H at the 6 position); 4.95 (1H, doublet, H at the 13 position, J=10.7 Hz).

EXAMPLE 73

13-(α-Cyclohexylbenzylcarbonyloxy)-5-keto-25-ethylmilbemycin 5-oxime (Compound of formula (Ia) wherein: $R^1$=ethyl $R^5$=α-cyclohexylbenzyl, n=0).

Mass Spectrum (m/z): 771(M+), 755, 737, 553, 535, 519.

Nuclear Magnetic Resonance Spectrum (270 MHz, CDCl$_3$) δ ppm: 4.66 (1H, singlet, H at the 6 position); 4.90 (1H, doublet, H at the 13 position, J=10.6 Hz).

EXAMPLE 74

13-(1-Phenylcyclopentylcarbonyloxy)-5-keto-25ethylmilbemycin 5-oxime (Compound of formula (Ia) wherein: $R^1$=ethyl, $R^5$=1-phenylcyclopentyl, n=0).

Mass Spectrum (m/z): 743(M+) 725, 709, 553, 519.

Nuclear Magnetic Resonance Spectrum (270 MHz, CDCl$_3$) δ ppm: 4.65 (1H, singlet, H at the 6 position); 4.80 (1H, doublet, H at the 13 position, J=10.3 Hz).

EXAMPLE 75

13-[2-(Phenylthio)propionyloxy]-5-keto-25-ethylmilbemycin 5-oxime (Compound of formula (Ia) wherein: $R^1$=ethyl, $R^5$=1-(phenylthio)ethyl, n=0).

Mass Spectrum (m/z): 735(M+), 717, 701, 553, 519.

Nuclear Magnetic Resonance Spectrum (270 MHz, CDCl$_3$) δ ppm: 4.67 (1H, singlet, H at the 6 position); 4.94 (1H, doublet, H at the 13 position, J=10.5 Hz).

EXAMPLE 76

13-(3-Methyl-2-phenylvaleryloxy)-5-keto-25-ethylmilbemycin 5-oxime (Compound of formula (Ia) wherein: $R^1$=ethyl, $R^5$=α-sec-butylbenzyl, n=0).

Mass Spectrum (m/z): 745(M+), 727, 711, 530, 515.

Nuclear Magnetic Resonance Spectrum (270 MHz, CDCl$_3$) δ ppm: 4.66 (1H, singlet, H at the 6 position); 4.87 (0.5H, doublet, M at the 13 position, J=10.6 Hz); 4.90 (0.5H, doublet, H ac the 13 position, J=10.6 Hz).

EXAMPLE 77

13-(1-Phenylcyclopropylcarbonyloxy)-5-keto-25ethylmilbemycin 5-oxime (Compound of formula (Ia) wherein: $R^1$=ethyl, $R^5$=1-phenylclopropyl, n=0).

Mass Spectrum (m/z): 715(M+), 697, 681, 553, 535, 519.

Nuclear Magnetic Resonance Spectrum (270 MHz, CDCl$_3$) δ ppm: 4.65 (1H, singlet, H at the 6 position); 4.87 (1H, doublet, H at the 13 position, J=10.6 Hz).

EXAMPLE 78

13-(2-o-Tolylpropionyloxy)-5-keto-25-ethylmilbemycin 5-oxime (Compound of formula (Ia) wherein: $R^1$=ethyl $R^5$=α-methyl-o-methylbenzyl n=0).

Mass Spectrum (m/z): 702(M+), 684, 670, 538, 520.

Nuclear Magnetic Resonance Spectrum (270 MHz, CDCl$_3$) δ ppm: 4.65 (1H, singlet, H at the 6 position); 4.90 (1H, doublet, H at the 13 position, J=10.6 Hz).

EXAMPLE 79

13-[2-(S)-Phenylpropionyloxy]-5-keto-25-ethylmilbemycin 5-oxime (Compound of formula (Ia) wherein: $R^1$=ethyl, $R^5$=(S)-α-methylbenzyl, n=0).

Mass Spectrum (m/z): 703(M+) 685, 670, 519.

Nuclear Maqnetic Resonance Spectrum 270 MHz, CDCl$_3$) δ ppm: 4.65 (1H, singlet, H at the 6 position); 4.89 (1H, doublet, H at the 13 position, J=10.6 Hz).

EXAMPLE 80

13-[2-(R)-Phenylpropionyloxy]-5-keto-25-ethylmilbemycin 5-oxime (Compound of formula (Ia) wherein: $R^1$=ethyl, $R^5$=(R)-α-methylbenzyl, n=0).

Mass Spectrum (m/z): 703(M+), 685, 669, 519.

Nuclear Magnetic Resonance Spectrum (270 MHz, CDCl$_3$) δ ppm: 4.66 (1H, singlet, H at the 6 position); 4.90 (1H, doublet, H at the 13 position, J=10.3 Hz).

EXAMPLE 81

13-(2-p-Chlorophenyl-2-methylpropionyloxy)-5-keto-25-ethylmilbemycin 5-oxime (Compound of formula (Ia) wherein: $R^1$=ethyl, $R^5$=α,α-dimethyl-p-chlorobenzyl, n=0).

Mass Spectrum (m/z): 751(M+), 717, 553, 535, 519.

Nuclear Magnetic Resonance Spectrum (270 MHz, CDCl$_3$) δ ppm: 4.66 (1H, singlet, H at the 6 position); 4.88 (1H, doublet, H at the 13 position, J=10.7 Hz).

EXAMPLE 82

13-(2-p-Chlorophenylpropionyloxy)-5-keto-25ethylmilbemycin 5-oxime (Compound of formula (Ia) wherein: $R^1$=ethyl, $R^5$=α-methyl-p-chlorobenzyl, n=0).

Mass Spectrum (m/z): 737(M+), 719, 703, 553, 535, 519.

Nuclear Magnetic Resonance Spectrum (270 MHz, CDCl$_3$) δ ppm: 4.66 (1H, singlet, H at the 6 position); 4.90 (1H, doublet, H at the 13 position, J=10.6 Hz).

EXAMPLE 83

13-[2-o-(Trifluoromethyl)phenylpropionyloxyl-5-keto-25-ethylmilbemycin 5-oxime (Compound of formula (Ia) wherein: $R^1$=ethyl, $R^5$=α-methyl-o-trifluoromethylbenzyl, n=0).

Mass Spectrum (m/z): 771(M+), 753, 737.

Nuclear Magnetic Resonance Spectrum (270 MHz, CDCl$_3$) δ ppm: 4.65 (1H, singlet, H at the 6 position); 4.88 (1H, doublet, H at the 13 position, J=10.6 Hz).

EXAMPLE 84

13-(2-o-Chlorophenylpropionyloxy)-5-keto-25ethylmilbemycin 5-oxime (Compound of formula (Ia) wherein: $R^1$=ethyl, $R^5$=α-methyl-o-chlorobenzyl, n=0).

Mass Spectrum (m/z): 737, 719, 703, 553.

Nuclear Magnetic Resonance Spectrum (270 MHz, CDCl$_3$) δ ppm: 4.66 (1H, singlet, H at the 6 position); 4.92 (1H, doublet, H at the 13 position, J=10.6 Hz).

EXAMPLE 85

13-(2-Methoxy-2-phenylacetoxy)-5-keto-25-ethylmilbemycin 5-oxime (Compound of formula (Ia) wherein: $R^1$=ethyl, $R^5$=α-methoxybenzyl, n=0).

Mass Spectrum (m/z): 719(M+), 701, 685, 553.

Nuclear Magnetic Resonance Spectrum (270 MHz, CDCl$_3$) δ ppm: 4.65 (1H, singlet, H at the 6 position); 4.94 (0.6H, doublet, H at the 13 position, J=10.3 Hz); 4.96 (0.4H, doublet, M at the 13 position, J=10.3 Hz).

EXAMPLE 86

13-(2,2-Diphenylpropionyloxy)-5-keto-25-ethylmilbemycin 5-oxime (Compound of formula (Ia) wherein: $R^1$=ethyl, $R^5$=α-methylbenzhydryl, n=0).

Mass Spectrum (m/z): 779(M+), 761, 745.

Nuclear Magnetic Resonance Spectrum (270 MHz, CDCl$_3$) δ ppm: 4.65 (1H, singlet, H at the 6 position); 4.98 (1H, douhlet, H at the 13 position, J=10.6 Hz).

EXAMPLE 87

13-(2-Methyl-2-phenylbutyryloxy)-5-keto-25-ethylmilbemycin 5-oxime (Compound of formula (Ia) wherein: $R^1$=ethyl, $R^5$=α-ethyl-α-methylbenzyl, n=0).

Mass Spectrum (m/z): 731(M+), 713, 589, 553, 535, 519.

Nuclear Magnetic Resonance Spectrum (270 MHz, CDCl$_3$) δ ppm: 4.65 (1H, sinqlet, H at the 6 position); 4.88 (0.5H, doublet, H at the 13 position, J=10.6 Hz); 4.90 (0.5H, doublet, H at the 13 position, J=10.6 Hz).

EXAMPLE 88

13-(2-p-Fluorophenyl-2-methylpropionyloxy)-5-keto-25-ethylmilbemycin 5-oxime (Compound of formula (Ia) wherein: $R^1$=ethyl, $R^5$=α,α-dimethyl-p-fluorobenzyl, n=0).

Mass Spectrum (m/z): 735(M+), 717, 701, 553, 519.

Nuclear Magnetic Resonance Spectrum (270 MHz, CDCl$_3$) δ ppm: 4.65 (1H, singlet, H at the 6 position); 4.87 (1H, doublet, H at the 13 position, J=10.6 Hz).

EXAMPLE 89

13-[2-Methyl-2-(p-chlorophenoxy)propionyloxy]-5-keto-25-ethylmilbemycin 5-oxime (Compound of formula (Ia) wherein: $R^1$=ethyl, $R^5$=1-methyl-1-(p-chlorophenoxy)ethyl, n=0).

Mass Spectrum (m/z): 767(M+), 733, 519.

Nuclear Magnetic Resonance Spectrum (270 MHz, CDCl$_3$) δ ppm: 4.66 (1H, singlet, H at the 6 position); 5.01 (1H, doublet, H at the 13 position, J=10.6 Hz).

EXAMPLE 90

13-Diphenylacetoxy-5-keto-25-ethylmilbemycin 5-oxime (Compound of formula (Ia) wherein: $R^1$=ethyl, $R^5$=benzhydryl, n=0).

Mass Spectrum (m/z): 765(M+), 747, 731.

Nuclear Magnetic Resonance Spectrum (270 MHz, CDCl$_3$) δ ppm: 4.66 (1H, singlet, H at the 6 position); 4.99 (1H, doublet, H at the 13 position, J=10.6 Hz).

EXAMPLE 91

13-(2-Phenylbutyryloxy)-5-keto-25-ethylmilbemycin 5-oxime (Compound of formula (Ia) wherein: $R^1$=ethyl, $R^5$=α-ethylbenzyl, n=0).

Mass Spectrum (m/z): 717(M+), 699, 683, 553, 536, 519.

Nuclear Magnetic Resonance Spectrum (270 MHz, CDCl$_3$) δ ppm: 4.66 (1H, singlet, H at the 6 position); 4.90 (0.2H, doublet, H at the 13 position, J=10.6 Hz); 4.91 (0.8H, doublet, H at the 13 position, J=10.6 Hz).

EXAMPLE 92

13-[2-(2-Pyridon-1-yl)propionyloxy]-5-keto-25ethylmilbemycin 5-oxime (Compound of formula (Ia) wherein: $R^1$=ethyl, $R^5$=1-(2-pyridon-1-yl)ethyl, n=0).

Mass Specttum (m/z): 720(M+), 702, 553, 520.

Nuclear Magnetic Resonance Spectrum (270 MHz, CDCl$_3$) δ ppm: 4.67 (1H, singlet, H at the 6 position); 4.95 (0.5H, doublet, H at the 13 position, J=10.5 Hz); 4.97 (0.5H, doublet, H at the 13 position, J=10.5 Hz).

EXAMPLE 93

13-(2,6-Difluorobenzoyloxy)-5-keto-23-hydroxy-25-(1,3-dimethyl-1-butenyl)milbemycin 5-oxime (Compound of formula (Ia) wherein: $R^1$=1,3-dimethyl-1-butenyl, $R^5$=2,6-difluorophenyl, X=—OH, n=0).

Mass Spectrum (m/z): 780(M+ −1), 762, 746, 744.

Nuclear Magnetic Resonance pectrum (270 MHz, CDCl$_3$) δ ppm: 4.67 (1H, singlet, H at the 6 position); 5.21 (1H, doublet, H at the 13 position, J=10.5 Hz).

EXAMPLE 94

13-(2-Phenylpropionyloxy)-5-keto-23-hydroxy-25-(1,3-dimethyl-1-butenyl)milbemycin 5-oxime (Compound of formula (Ia) wherein: $R^1$=1,3-dimethyl-1-butenyl, $R^5$=α-methylbenzyl, X=—OH, n=0).

Mass Spectrum (m/z): 773(M+), 755, 739, 331.

Nuclear Magnetic Resonance Spectrum (270 MHz, CDCl$_3$) δ ppm: 4.65 (1H, singlet, H at the 6 position); 4.89 (1H, doublet, H at the 13 position, J=10.5 Hz).

Examples 95 to 97 illustrate the preparation of compounds of formula (Ib) from starting materials of formula (III), by the reaction of Step B in the above reaction scheme.

EXAMPLE 95

13-Benzyloxycarbonyloxy-5-keto-25-ethylmilbemycin and -25-methylmilbemycin 5-O-carboxymethyloxime (mixture of two compounds in the ratio 2.5:1)

(Compound of formula (Ib) wherein: $R^1$=ethyl or methyl, $R^5$=benzyl, $R^3$=carboxymethyl, n=1).

By following the procedure of Example 1 and reacting 180 mg of a mixture of 13-benzyloxycarbonyloxy-5-keto-25-ethylmilbemycin and -25-methylmilbemycin (in the ratio of 2.3:1) with 340 mg of O-carboxymethylhydroxylamine hydrochloride, 198 mg of the target product were obtained (yield: 99%).

Mass Spectrum (m/z): 671(M+ −92), 627.

Nuclear Magnetic Resonance Spectrum (270 MHz, CDCl$_3$) δ ppm: 3.70 (1H, singlet, OH at the 7 position); 4.70 (1H, singlet, H at the 6 position); 4.72 (1H, doublet, H at the 13 position, J=10.6 Hz).

The compounds of Examples 96 and 97 were prepared from the corresponding hydroxylamine hydrochlorides, using the procedure of Example 95.

EXAMPLE 96

13-p-Trifluoromethylbenzoyloxy-5-keto-25-ethylmilbemycin and -25-methylmilbemycin 5-O-benzyloxime (mixture of two compounds in the ratio 3:1)

(Compound of formula (Ib) wherein: $R^1$=ethyl or methyl, $R^5$=p-trifluoromethylphenyl, $R^3$=benzyl, n=0).

Mass Spectrum (m/z): 833(M+).

Nuclear Magnetic Resonance Spectrum (270 MHz, CDCl$_3$) δ ppm: 3.89 (1H, singlet, OH at the 7 position); 4.61 (1H, singlet, H at the 6 position); 5.22 (1H, doublet, H at the 13 position, J=10.6 Hz).

EXAMPLE 97

13-p-Trifluoromethylbenzoyloxy-5-keto-25-ethylmilbemycin and -25-methylmilbemycin 5-O-methyloxime (mixture of two compounds in the ratio 2.6:1)

(Compound of formula (Ib) wherein: $R^1$=ethyl or methyl, $R^5$=p-trifluoromethylphenyl, $R^3$=methyl n=0).

Mass Spectrum (m/z): 758(M+), 743.

Nuclear Magnetic Resonance Spectrum (270 MHz, CDCl$_3$) δ ppm: 3.94 (1H, singlet, OH at the 7 position); 4.57 (1H, singlet, H at the 6 position); 5.22 (1H, doublet, H at the 13 position, J=10.6 Hz).

Examples 98 to 128 illustrate the preparation of compounds of formula (Ib) from starting materials of formula (Ia), by the reaction of Step C in Reaction Scheme No. 1.

EXAMPLE 98

13-Ethoxycarbonyloxy-5-keto-25-ethylmilbemycin 5-O-pivaloyloxime (Compound of formula (Ib) wherein: $R^1$=ethyl, $R^5$=ethyl, $R^3$=pivaloyl, n=1).

To a solution of 129 mg of 13-ethoxycarbonyloxy-5-keto-25-ethylmilbemycin 5 oxime in 5 ml of benzene were added 22 μl of piyaloyl chloride and 31 μl of triethylamine, under ice-cooling, and the resulting mixture was stirred at room temperature for 4 hours. After completion of the reaction, the mixture was poured into water and extracted with ethyl acetate. The extracts were washed with a saturated solution of sodium chloride, dried over anhydrous sodium sulfate and concentrated. The residue was subjected to column chromatography over silica gel, giving 113 mg of the target product (yield: 77.4%).

Mass Spectrum (m/z): 727(M+).

Nuclear Magnetic Resonance Spectrum (270 MHz, CDCl$_3$) δ ppm: 3.98 (1H, singlet, OH at the 7 position); 4.57 (1H, singlet, H at the 6 position); 4.75 (1H, doublet, H at the 13 position, J=10.6 Hz).

The compounds of Examples 99 to 127 were prepared from the corresponding acid halides by the procedure of Example 98.

EXAMPLE 99

13-p-Fluorophenoxyacetoxy-5-keto-25-ethylmilbemycin 5-O-pivaloyloxime (Compound of formula (Ib) wherein: $R^1$=ethyl, $R^5$=p-fluorophenoxymethyl, $R^3$=pivaloyl, n=0).

Mass Spectrum (m/z): 745(M+ −62), 689.

Nuclear Magnetic Resonance Spectrum (270 MHz, CDCl$_3$) δ ppm: 3.99 (1H, singlet, OH at the 7 position); 4.57 (1H, singlet, H at the 6 position); 5.05 (1H, doublet, H at the 13 position, J=10.3 Hz).

EXAMPLE 100

13-p-t-Butylbenzoyloxy-5-keto-25-ethylmilbemycin 5-O-(N,N-dimethylcarbamoyl)oxime (Compound of formula (ib) wherein; $R^1$=ethyl, $R^5$=p-t-butylphenyl, $R^3$=N,N-dimethylcarbamoyl, n=0).

Mass Spectrum (m/z): 697(M+ −106).

Nuclear Magnetic Resonance Spectrum (270 MHz, CDCl$_3$) δ ppm: 3.99 (1H, singlet, OH at the 7 position); 4.58 (1H, singlet, H at the 6 position); 5.20 (1H, doublet, H at the 13 position, J=10.6 Hz).

EXAMPLE 101

13-o-Trifluoromethylbenzoyloxy-5-keto-25-ethylmilbemycin 5-O-(N,N-dimethylcarbamoyl)oxime (Compound of formula (Ib) wherein: R$^1$=ethyl, R$^5$=o-trifluoromethylphenyl, R$^3$=N,N-dimethylcarbamoyl, n=0).

Mass Spectrum (m/z): 753(M$^+$ −61), 709.

Nuclear Magnetic Resonance Spectrum (270 MHz, CDCl$_3$) δ ppm: 3.99 (1H, singlet, OH at the 7 position); 4.58 (1H, singlet, H ar the 6 position); 5.24 (1H, doublet, H at the 13 position, J=10.6 Hz).

EXAMPLE 102

13-(2-Furoyloxy)-5-keto-25-ethylmilbemycin 5-O-(N,N-dimethylcarbamoyl)oxime (Compound of formula (Ib) wherein: R$^1$=ethyl, R$^5$=2-furyl, R$^3$=N,N-dimethylcarbamoyl, n=0).

Mass Spectrum (m/z): 675(M$^+$ −61), 649, 631.

Nuclear Magnetic Resonance Spectrum (270 MHz, CDCl$_3$) δ ppm: 3.96 (1H, singlet, OH at the 7 position); 4.58 (1H, singlet, H at the 6 position); 5.17 (1H, doublet, H at the 13 position, J=10.6 Hz).

EXAMPLE 103

13-Benzyloxycarbonyloxy-5-keto-25-ethylmilbemycin 5-O-(N,N-dimethylcarbamoyl)oxime (Compound of formula (Ib) wherein: R$^1$=ethyl, R$^5$=benzyl, R$^3$=N,N-dimethylcarbamoyl, n=1).

Mass Spectrum (m/z): 688(M$^+$ −88).

Nuclear Magnetic Resonance Spectrum (270 MHz, CDCl$_3$) δ ppm: 3.96 (1H, singlet, OH at the 7 position); 4.56 (1H, singlet, H at the 6 position); 4.76 (1H, doublet, H at the 13 position, J=10.6 Hz).

EXAMPLE 104

13-Methoxycarbonyloxy-5-keto-25-ethylmilbemycin 5-O-(N,N-dimethylcarbamoyl)oxime (Compound of formula (Ib) wherein: R$^1$=ethyl, R$^5$=methyl, R$^3$=N,N-dimethylcarbamoyl, n=1)

Mass Spectrum (m/z): 700(M$^+$).

Nuclear Magnetic Resonance Spectrum (270 MHz, CDCl$_3$) δ ppm: 3.95 (1H, singlet, OH at the 7 position); 4.57 (1H, singlet, H at the 6 position); 4.72 (1H, doublet, H at the 13 position, J=11 Hz).

EXAMPLE 105

13-(2,2,2-Trichloroethoxycarbonyloxy)-5-keto-25-ethylmilbemycin 5-O-(N,N-dimethylcarbamoyl)oxime (Compound of formula (Ib) wherein: R$^1$=ethyl, R$^5$=2,2,2-trichloroethyl, R$^3$=N,N-dimerhylcarbamoyl, n=1).

Mass Spectrum (m/z): 815(M$^+$).

Nuclear Magnetic Resonance Spectrum (270 MHz, CDCl$_3$) δ ppm: 3.97 (1H, singlet, OH at the 7 position); 4.59 (1H, singlet, H at the 6 position); 4.81 (1H, doublet, H at the 13 position, J=10.3 Hz).

EXAMPLE 106

13-(2,2-Dimethyl-1,3-dioxolanylmethoxycarbonyloxy)-5-keto-25-ethylmilbemycin and 25-methylmilbemycin 5-O-(N,N-dimethylcarbamoyl)oxime (mixture of two compounds in the ratio 2:1)

(Compound of formula (Ib) wherein: R$^1$=ethyl or methyl, R$^5$=2,2-dimethyl-1,3-dioxolanylmethyl, R$^3$=N,N-dimethylcarbamoyl, n=1).

Mass Specttum (m/z): 734(M$^+$ −66).

Nuclear Magnetic Resonance Spectrum (270 MHz, CDCl$_3$) δ ppm: 3.96 (1H, singlet, OH at the 7 position); 4 57 (1H, singlet, H at the 6 position); 4.74 (1H, doublet, H at the 13 position, J=12.8 Hz).

EXAMPLE 107

13-(3-Chloropropionyloxy)-5-keto-25-ethylmilbemycin 5-O-tosyloxime (Compound of formula (Ib) wherein: R$^1$=ethyl, R$^5$=2-chloroethyl, R$^3$=tosyl, n=0).

Mass Spectrum (m/z): 644(M$^+$ −155).

Nuclear Magnetic Resonance Spectrum (270 MHz, CDCl$_3$) δ ppm: 3.84 (1H, singlet, OH at the 7 position); 4.51 (1H, singlet, H at the 6 position); 5.00 (1H, doublet, H at the 13 position, J=10.6 Hz).

EXAMPLE 108

13-(3-Chloropropionyloxy)-5-keto-25-methylmilbemycin 5-O-tosyloxime (Compound of formula (Ib) wherein: R$^1$=methyl, R$^5$=2-chloroethyl, R$^3$=tosyl, n=0).

Mass Spectrum (m/z); 630(M$^+$ −155).

Nuclear Magnetic Resonance Spectrum (270 MHz, CDCl$_3$) δ ppm: 3.84 (1H, singlet, OH at the 7 position); 4.51 (1H, singlet, H at the 6 position); 5.00 (1H, doublet, H at the 13 position, J=10.6 Hz).

EXAMPLE 109

13-(2-Methoxyethoxycarbonyloxy)-5-keto-25-ethylmilbemycin 5-O-(N,N-dimethylcarbamoyl)oxime (Compound of formula (Ib) wherein: R$^1$=ethyl, R$^5$=2-methoxyethyl, R$^3$=N,N-dimethylcarbamoyl, n=1).

Mass Spectrum (m/z): 744(M$^+$), 640.

Nuclear Magnetic Resonance Spectrum (270 MHz, CDCl$_3$) δ ppm: 3.96 (1H, singlet, OH at the 7 position); 4.57 (1H, singlet, H at the 6 position); 4.75 (1H, doublet, H at the 13 position, J=10.6 Hz).

EXAMPLE 110

13-[2-(2,2-Dichlorovinyl)-3,3-dimethylcyclopropylcarbonyloxy-5-keto-25-ethylmilbemycin and -25-methylmilbemycin 5-O-propionyloxime (mixture of two compounds in the ratio 2.6:1)

(Compound of formula (Ib) wherein: R$^1$=ethyl or methyl, R$^5$=2-(2,2-dichloroyinyl)3,3-dimethylcyclopropyl, R$^3$=propionyl, n=0).

Mass Spectrum (m/z): 745(M$^+$ −72).

Nuclear Magnetic Resonance Spectrum (270 MHz, CDCl$_3$) δ ppm: 3.96 (1H, singlet, OH at the 7 position); 4.60 (1H, singlet, H at the 6 position); 5.43 (1H, doublet, H at the 13 position, J=10.6 Hz).

EXAMPLE 111

13-Trichloroacetoxy-5-keto-25-ethylmilbemycin 5-O-propionyloxime (Compound of formula (Ib) wherein: $R^1$=ethyl, $R^5$=trichloromethyl, $R^3$=propionyl, n=0).

Mass Spectrum (m/z): 771(M+).

Nuclear Magnetic Resonance Spectrum (270 MHz, $CDCl_3$) δ ppm: 3.96 (1H, singlet, OH at the 7 position); 4.61 (1H, singlet, H at the 6 position); 4.99 (1H, doublet, H at the 13 position, J=10.6 Hz).

EXAMPLE 112

13-Ethoxycarbonyloxy-5-keto-25-ethylmilbemycin and -25-methylmilbemycin 5-O-acetyloxime (mixture of two compounds in the ratio 2.8:1)

(Compound of formula (Ib) wherein: $R^1$=ethyl or methyl, $R^5$=ethyl, $R^3$=acetyl, n=1).

Mass Spectrum (m/z): 685(M+).

Nuclear Magnetic Resonance Spectrum (270 MHz, $CDCl_3$) δ ppm: 3.96 (1H, singlet, OH at the 7 position); 4.60 (1H, singlet, H at the 6 position); 4.75 (1H, doublet, H at the 13 position, J=11 Hz).

EXAMPLE 113

13-Ethoxycarbonyloxy-5-keto-25-ethylmilbemycin and -25-methylmilbemycin 5-O-palmitoyloxime (mixture of two compounds in the ratio 3.3:1)

(Compound of formula (Ib) wherein: $R^1$=ethyl or methyl, $R^5$=ethyl, $R^3$=palmitoyl, n=1).

Mass Spectrum (m/z): 610(M+ −271).

Nuclear Magnetic Resonance Spectrum (270 MHz, $CDCl_3$) δ ppm: 3.95 (1H, singlet, OH at the 7 position); 4.59 (1H, singlet, H at the 6 position); 4.70 (1H, doublet, H at the 13 position, J=10.6 Hz).

EXAMPLE 114

13-(2,2,2-Trichloroethoxycarbonyloxy)-5-keto-25-ethylmilbemycin 5-O-propionyloxime (Compound of formula (Ib) wherein: $R^1$=ethyl, $R^5$=2,2,2-trichloroethyl, $R^3$=propionyl, n=1).

Mass Spectrum (m/z): 801(M+).

Nuclear Magnetic Resonance Spectrum (270 MHz, $CDCl_3$) δ ppm: 3.96 (1H, singlet, OH at the 7 position); 4.60 (1H, singlet, H at the 6 position); 4.81 (1H, doublet, H at the 13 position, J=10.3 Hz).

EXAMPLE 115

13-(2,2,2-Trichloroethoxycarbonyloxy)-5-keto-25-ethylmilbemycin 5-O-(N,N-dimethylcabamoyl)oxime (Compound of formula (Ib) wherein: $R^1$=ethyl, $R^5$=2,2,2-trichloroethyl, $R^3$=N,N-dimethylcarbamoyl, n=1).

Mass Spectrum (m/z): 815(M+).

Nuclear Magnetic Resonance Spectrum (270 MHz, $CDCl_3$) δ ppm: 3.97 (1H, singlet, OH at the 7 position); 4.59 (1H, singlet, H at the 6 position); 4.81 (1H, doublet, H at the 13 position, J=10.8 Hz).

EXAMPLE 116

13-(2,2,2-Trichloroethoxycarbonyloxy)-5-keto-25-ethylmilbemycin 5-O-acetyloxime (Compound of formula (Ib) wherein: $R^1$=ethyl, $R^5$=2,2,2-trichloroethyl, $R^3$=acetyl, n=1).

Mass Spectrum (m/z): 787(M+).

Nuclear Magnetic Resonance Spectrum (270 MHz, $CDCl_3$) δ ppm: 3.96 (1H, singlet, OH at the 7 position); 4.60 (1H, singlet, H at the 6 position); 4.82 (1H, doublet, H at the 13 position, J=10.7 Hz).

EXAMPLE 117

13-p-Bromobenzoyloxy-5-keto-25-ethylmilbemycin 5-O-octanoyloxime (Compound of formula (Ib) wherein: $R^1$=ethyl, $R^5$=p-bromophenyl, $R^3$=octanoyl, n=0).

Mass Spectrum (m/z): 719(M+ −161, with $Br^{79}$).

Nuclear Magnetic Resonance Spectrum (270 MHz, $CDCl_3$) δ ppm: 3.6 (1H, broad singlet, OH at the 7 position); 4.61 (1H, singlet. H at the 6 position); 5.19 (1H, doublet, H at the 13 position, J=10.4 Hz).

EXAMPLE 118

13-Pivaloyl-5-keto-25-ethylmilbemycin 5-O-diethoxythiophosphoryloxime (Compound of formula (Ib) wherein: $R^1$=ethyl, $R^5$=t-butyl, $R^3$=diethoxythiophosphoryl, n=0).

Mass Spectrum (m/z): 649(M+ −158), 621.

Nuclear Magnetic Resonance Spectrum (270 MHz, $CDCl_3$) δ ppm: 3.85 (1H, singlet, OH at the 7 position); 4.70 (1H, singlet, H at the 6 position); 4.91 (1H, doublet, H at the 13 position, J=10.6 Hz).

EXAMPLE 119

13-o-Trifluoromethylbenzoyloxy-5-keto-25-ethylmilbemycin 5-O-pentaacetylgluconyloxime (Compound of formula (Ib) wherein: $R^1$=ethyl, $R^5$=o-trifluoromethylphenyl, $R^3$=pentaacetylgluconyl, n=0).

Mass Spectrum (m/z): 727(M+ −404).

Nuclear Magnetic Resonance Spectrum 270 MHz, $CDCl_3$) δ ppm: 3.93 (1H, singlet, OH at the 7 position); 4.54 (1H, singlet, H at the 6 position); 5.42 (1H, doublet, H at the 13 position, J=10.6 Hz).

EXAMPLE 120

13-[2-(2,2-Dichlorovinyl)-3,3-dimethylcyclopropylcarbonyloxy]-5-keto-25-ethylmilbemycin and -25-methylmilbemycin 5-O-(N,N-dimethylcarbamoyl)oxime (mixture of two compounds in the ratio 2.6:1)

(Compound of formula (Ib) wherein: $R^1$=ethyl or methyl, $R^5$=2-(2,2-dichlorovinyl)-3,3-dimethylcyclopropyl, $R^3$=N,N-dimethylcarbamoyl, n=0).

Nuclear Magnetic Resonance Spectrum (270 MHz, $CDCl_3$) δ ppm: 2.99 (6H, singlet, $N(CH_3)_2$); 3.98 (1H, singlet, OH at the 7 position); 4.57 (1H, singlet, H at the 6 position); 4.72 (2H, singlet, $CH_2$ at the 27 position); 4.96 (0.5H, doublet, H at the 13 position, J=10.3 Hz); 5.00 (0.5H, doublet, H at the 13 position, J=10.3 Hz).

EXAMPLE 121

13-Iodoacetoxy-5-keto-25-ethylmilbemycin and -25-methylmilbemycin 5-O-propionyloxime (mixture of two compounds in the ratio 2.3:1)

(Compound of formula (Ib) wherein: $R^1$=ethyl or methyl, $R^5$=iodomethyl, $R^3$=propionyl, n=0).

Mass Spectrum (m/z): 795(M+), 781, 703.

Nuclear Magnetic Resonance Spectrum (270 MHz, $CDCl_3$) δ ppm: 3.68 (1H, singlet, OH at the 7 position); 4.60 (1H, singlet, H at the 6 position); 4.93 (0.5H, doublet, H at the 13 position, J=10.5 Hz); 5.01 (0.5H, doublet, H at the 13 position, J=10.5 Hz).

EXAMPLE 122

13-Acetoxyacetoxy-5-keto-25-ethylmilbemycin and -25-methylmilbemycin 5-O-propionyloxime (mixture of two compounds in the ratio 2.3:1)

(Compound of formula (Ib) wherein: $R^1$=ethyl or methyl, $R^5$=acetoxymethyl, $R^3$=propionyl, n=0).

Mass Spectrum (m/z): 727($M^+$), 637.

Nuclear Magnetic Resonance Spectrum (270 MHz, CDCl$_3$) δ ppm: 3.94 (1H, singlet, OH at the 7 position); 5.03 (1H, doublet, H at the 13 position, J=10.3 Hz).

EXAMPLE 123

13-Propionyloxyacetoxy-5-keto-25-ethylmilbemycin and -25-methylmilbemycin 5-O-propionyloxime (mixture of two compounds in the ratio 2.3:1)

(Compound of formula (Ib) wherein: $R^1$=ethyl or methyl, $R^5$=propionyloxymethyl, $R^3$=propionyl, n=0).

Mass Spectrum (m/z): 741($M^+$), 703.

Nuclear Magnetic Resonance Spectrum (270 MHz, CDCl$_3$) δ ppm 3.95 (1H, singlet, OH at the 7 position); 5.02 (1H, doublet, H at the 13 position, J=10.6 Hz).

EXAMPLE 124

13-Pivaloyloxy-5-kero-25-ethylmilbemycin 5-O-pentaacetylgluconyloxime (Compound of formula (Ib) wherein: $R^1$=ethyl, $R^5$=t-butyl, $R^3$=pentaacetylgluconyl n=0).

Mass Spectrum (m/z): 1044($M^+$+1), 943, 941, 655, 639, 637.

Nuclear Magnetic Resonance Spectrum (270 MHz, CDCl$_3$) δ ppm: 4.53 (1H, singlet, H at the 6 position); 4.83 (1H, doublet, H at the 13 position, J=10.6 Hz).

EXAMPLE 125

13-(2-Phenylpropionyloxy)-5-keto-25-ethylmilbemycin 5-O-pivaloyloxime (Compound of formula (Ib) wherein: $R^1$=ethyl, $R^5$=α-methylbenzyl, $R^3$=pivaloyl, n=0).

Mass Spectrum (m/z): 801($M^+$), 536, 279.

Nuclear Magnetic Resonance Spectrum (270 MHz, CDCl$_3$) δ ppm: 4.55 (1H, singlet, H at the 6 position); 4.88 (1H, doublet, H at the 13 position, J=10.5 Hz).

EXAMPLE 126

13-(2,6-Difluorobenzoyloxy)-5-keto-25-ethylmilbemycin 5-O-pivaloyloxime (Compound of formula (Ib) wherein: $R^1$=ethyl, $R^5$=2,6-difluorophenyl, $R^3$=pivaloyl, n=0).

Mass Spectrum (m/z): 795($M^+$), 694, 676, 535.

Nuclear Magnetic Resonance Spectrum (270 MHz, CDCl$_3$) δ ppm: 4.58 (1H, singlet, H at the 6 position); 5.22 (1H, doublet, H at the 13 position, J=10.5 Hz).

EXAMPLE 127

13-(2-Furoyloxy)-5-keto-25-ethylmilbemycin 5-O-pentaacetyloluconyloxime (Compound of formula (Ib) wherein: $R^1$=ethyl, $R^5$=2-furyl. $R^3$=penraacetylgluconyl, n=0).

Mass Spectrum (m/z): 648($M^+$ −405), 646, 631, 535, 519.

Nuclear Magnetic Resonance Spectrum (270 MHZ, CDCl$_3$) δ ppm: 4.54 (1H, singlet, H at the 6 position); 5.18 (1H, doublet, H at the 13 position, J=10.6 Hz).

EXAMPLE 128

13-Pivaloyloxy-5-keto-25-ethylmilbemycin 5-O-(N-methylcarbamoyl)oxime (Compound of formula (Ib) wherein: $R^1$=ethyl, $R^5$=t-butyl, $R^3$=N-methylcarbamoyl, n=0).

To a solution of 131 mg of 13-pivaloyloxy-5-keto-25-ethylmilbemycin 5-oxime in 5 ml of tetrahydrofuran was added 1 ml of methylisocyanate and the mixture was allowed to stand for 8 hours. After completion of the reaction. the solyent was distilled off and the residue subjected to column chromatography oyer silica gel, giving 118 mg of the target product (yield: 83.1%).

Mass Spectrum (m/z): 655($M^+$ −57), 637, 553.

Nuclear Magnetic Resonance Spectrum (270 MHz, CDCl$_3$) δ ppm: 3.90 (1H, singlet, OH at the 7 position); 4.67 (1H, singlet, H at the 6 position); 4.91 (1H, doublet, H at the 13 position, J=10.6 Hz).

Examples 129 to 157 illustrate the preparation of compounds of formula (IIb) from starting materials of formula (IIa), by the reaction of Step B in Reaction Scheme No. 2 above.

EXAMPLE 129

13-(2-Methyl-2-phenylpropionyloxy)-25-ethylmilbemycin (Compound of formula (IIb) wherein: $R^1$=ethyl, Z=α,α-dimethylbenzyl, Y=—OH).

3.5 mg of sodium borohydride were added, under ice-cooling, to a solution of 123 mg of 13-(2-methyl-2-phenylpropionyloxy)-5-keto-25-ethylmilbemycin in 5 ml of methanol, and then the mixture was stirred at room temperature for 30 minutes. At the end of this time, the reaction mixture was poured into water and extracted with ethyl acetate. The extract was washed, in turn, with water and a saturated aqueous solution of sodium chloride, dried oyer magnesium sulfate and concentrated by eyaporation. The residue was purified by column chromatography through silica gel to give 85 mg (yield: 69%) of the title compound.

Mass Spectrum (M/z): 704($M^+$), 686, 646, 576, 540, 522.

Nuclear Magnetic Resonance Spectrum (CDCl$_3$) δ ppm: 3.94 (1H, doublet, H at the 6 position, J=6.6 Hz); 4.07 (1H, singlet, OH at the 7 position) 4.28 (1H, doublet of doublets, H at the 5 position, J=6.6, 6.6 Hz); 4.65 (2H, multiplet, H at the 27 position); 4.86 (1H, doublet, H at the 13 position, J=10.6 Hz); 7.28 (5H, multiplet).

By following the procedure of Example 129, the compounds of Examples 130 to 157 were prepared, having the characteristics shown.

EXAMPLE 130

13-(2-Phenylpropionyloxy)-25-ethylmilbemycin (Compound of formula (IIb) wherein: $R^1$=ethyl, Z=α-methylbenzyl, Y=—OH).

Mass Specrrum (m/z): 690($M^+$), 632, 562.

Nuclear Magnetic Resonance Spectrum (CDCl$_3$) δ ppm: 3.947 and 3.952 (1H, doublet, H at the 6 position, J=6.2 Hz); 4.05 and 4.08 (1H, singlet, OH at the 7 position); 4.89 (1H, singlet, H at the 13 position, J=10.6 Hz).

EXAMPLE 131

13-(2-Phenylbutyryloxy)-25-erhylmilbemycin (Compound of formula (IIb) wherein: R$^1$=ethyl, Z=α-ethylbenzyl, Y=—OH).

Mass Spectrum (m/z); 704(M+), 686.

Nuclear Magnetic Resonance pectrum (CDCl$_3$) δ ppm: 3.95 (1H, doublet, H at the 6 position, J=6.2 Hz); 4.05 and 4.08 (1H, singlet, OH at the 7 position); 4.89 and 4.90 (1H, doublet, H at the I3 position, J=10.6 Hz).

EXAMPLE 132

13-(3-Methyl-2-phenylvaleryloxy)-25-ethylmilbemycin (Compound of formula (IIb) wherein: R$^1$=ethyl, Z=α-sec-butylbenzyl, Y=—OH).

Mass Spectrum (m/Z): 732(M+), 714, 604, 540, 522, 504.

Nuclear Magnetic Resonance Spectrum (CDCl$_3$) δ ppm: 3.95 (1H, doublet, H are the 6 position J=6.1 Hz); 4.09 (1H, multiplet, OH at the 7 position), 4.86 and 4.89 (1H, doublet, H at the 13 position, J=10.5 Hz).

EXAMPLE 133

13-Benzhydrylcarbonyloxy-25-ethylmilbemycin (Compound of formula (IIb) wherein: R$^1$=ethyl, Z=benzhydryl, Y=—OH).

Mass Spectrum (m/z): 752(M+), 734, 716.

Nuclear Magneric Resonance pectrum (CDCl$_3$) δ ppm: 3.95 (1H, doublet, H at the 6 position, J=6.1 Hz); 4.07 (1H, singlet, OH at the 7 position); 4.98 (1H, doublet, H at the 13 position, J=9.2 Hz).

EXAMPLE 134

13-(2-Methyl-2-phenylbutyryloxy)-25-ethylmilbemycin (Compound of formula (IIb) wherein: R$^1$=ethyl, Z=α-ethyl-α-merhylbenzyl, Y=—OH).

Mass Specrrum (m/z): 718(M+), 700.

Nuclear Magnetic Resonance Spectrum (CDCl$_3$) δ ppm: 3.94 (1H, doublet, H at the 6 position, J=6.2 Hz); 4.08 (1H, broad singlet, OH at the 7 position); 4.87 and 4.90 (1H, doublet, H at the 13 position, J=10.6 Hz).

EXAMPLE 135

13-(2,2-Diphenylpropionyloxy)-25-ethylmilbemycin (Compound of formula (IIb) wherein: R$^1$=ethyl, Z=α-methylbenzhydryl, Y=—OH).

Mass Spectrum (m/z): 766(M+), 748, 730.

Nuclear Magnetic Resonance Spectrum (CDCl$_3$) δ ppm: 4.28 (1H, doublet, H at the 5 position, J=5.9 Hz); 4.61 (1H, doublet, H at the 27 position, J=15.2 Hz); 4.68 (1H, doublet, H at the 27 position, J=15.2 Hz); 4.97 (1H, doublet, H at the 13 position, J=10.6 Hz); 5.25–5.48 (4H, multiplet, H at the 3, 11, 15 and 19 position); 5.70–5.82 (2H, multiplet, H at the 9 and 10 position).

EXAMPLE 136

13-(2-o-Chlorophenylpropionyloxy)-25-ethylmilbemycin (Compound of formula (IIb) wherein: R$^1$=ethyl, Z=α-methyl-o-chlorobenzyl, Y=—OH).

Mass Spectrum (m/z): 724(M+), 706.

Nuclear Magnetic Resonance Spectrum (CDCl$_3$) δ ppm: 3.95 (1H, doublet, H at the 6 position, J=6.2 Hz); 4.08 (1H, singlet, OH at the 7 position); 4.92 and 4.94 (1H, doublet, H at the 13 position, J=10.3 Hz).

EXAMPLE 137

13-[2-o-(Trifluoromethyl)phenylpropionyloxy]-25-ethylmilbemycin (Compound of formula (IIb) wherein: R$^1$=ethyl, Z=α-methyl-o-(trifluoromethyl)benzyl, Y=—OH).

Mass Spectrum (m/z): 758(M+), 740, 722.

Nuclear Magnetic Resonance Spectrum (CDCl$_3$) δ ppm: 4.31 (1H, broad singlet, H at the 5 position); 4.67 (2H, broad singlet, 2H at the 27 position); 4.88 (1H, doublet, H at the 13 position, J=10.6 Hz); 5.25–5.41 (4H, multiplet, H at the 3, 11, 15 and 19 position); 5.70–5.86 (2H, multiplet, H at the 9 and 10 position).

EXAMPLE 138

13-(2-p-Nitrophenylpropionyloxy)-25-ethylmilbemycin (Compound of formula (IIb) wherein: R$^1$=ethyl, Z=α-methyl-p-nitrobenzyl, Y=—OH).

Mass Spectrum (m/z): 735(M+), 607, 589, 522.

Nuclear Magnetic Resonance Spectrum (CDCl$_3$) δ ppm: 3.95 (1H, doublet H at the 6 position, J=6.1 Hz); 4.07 (1H, singlet, OH at the 7 position); 4.91 and 4.92 (1H, doublet, H at the 13 position, J=10.3 Hz).

EXAMPLE 139

13-(2-Methyl-2-p-chlorophenylpropionyloxy)-25-ethylmilbemycin (Compound of formula (IIb) wherein: R$^1$=ethyl, Z=α,α-dimethyl-p-chlorobenzyl, Y=—OH).

Mass Spectrum (m/z): 738(M+), 610, 576.

Nuclear Magnetic Resonance Spectrum (CDClhd 3) δ ppm: 3.95 (1H, doublet, H at the 6 position, J=6.2 Hz); 4.07 (1H, singler, OH at the 7 position); 5.01 (1H, doublet, H at the 13 position, J=10.3 Hz).

EXAMPLE 140

13-(2-Methyl-2-p-fluorophenylpropionyloxy)-25-ethylmilbemycin (Compound of formula (IIb) wherein: R$^1$=ethyl, Z=α,α-dimethyl-p-fluorobenzyl, Y=—OH).

Mass Spectrum (m/z): 722(M+), 704, 686.

Nuclear Magnetic Resonance Spectrum (CDCl$_3$) δ ppm: 3.95 (1H, doublet, H at the 6 position, J=6.2 Hz); 4.07 (1H, broad singlet, OH at the 7 position); 4.86 (1H, doublet, H at the 13 position, J=10.3 Hz).

EXAMPLE 141

13-(α-Methoxybenzylcarbonyloxy)-25-ethylmilbemycin (Compound of formula (IIb) wherein: R$^1$=ethyl, Z=α-methoxybenzyl, Y=—OH).

Mass Spectrum (m/z): 706(M+), 688.

Nuclear Magnetic Resonance Spectrum (CDCl$_3$) δ ppm: 3.94 and 3.95 (1H, doublet, H at the 6 position, J=6.2 Hz); 4.10 (1H, broad singlet, OH at the 7 position); 4.94 and 4.95 (1H, doublet, H at the 13 position, J=10.6 Hz).

EXAMPLE 142

13-[2-Methyl-2-(p-chlorophenoxy)propionyloxy]-25-ethylmilbemycin (Compound of formula (IIb) wherein: R$^1$=ethyl, Z=1-methyl-1-(p-chlorophenoxy)ethyl, Y=—OH).

Mass Spectrum (m/z): 754(M+), 736, 718.

Nuclear Magnetic Resonance Spectrum (CDCl$_3$) δ ppm: 3.95 (1H, doublet, H at the 6 position, J=6.2 Hz); 4.07 (1H, singlet, OH at the 7 position); 5.01 (1H, doublet, H at the 13 position, J=10.3 Hz).

EXAMPLE 143

13-{2-[p-(phenoxy)phenoxy]propionyloxy}-25-ethylmilbemycin (Compound of formula (IIb) wherein: R$^1$=ethyl, Z=1-[p-(phenoxy)phenoxy]ethyl, Y=—OH).

Mass Spectrum (m/z): 798(M+), 780, 762, 670, 540, 522, 504.

Nuclear Magnetic Resonance Spectrum (CDCl$_3$) δ ppm: 3.96 (1H, doublet, H at the 6 position, J=6.2 Hz); 4.06 (1H, singlet, OH at the 7 position); 4.95 (1H, doublet, H at the 13 position, J=10.3 Hz).

EXAMPLE 144

13-{2-[p-(5-Trifluoromethyl-2-pyridyloxy)phenoxy]-propionyloxy}-25-ethylmilbemycin (Compound of formula (IIb) wherein: R$^1$=ethyl, Z=1-[p-(5-trifluoromethyl-2-pyridyloxy)phenoxy]ethyl, Y=—OH).

Mass Spectrum (m/z): 867(M+), 849, 831, 813, 540, 522, 504.

Nuclear Magnetic Resonance Spectrum (CDCl$_3$) δ ppm: 3.96 (1H, doublet, H at the 6 position, J=6.2 Hz); 4.10 (1H, broad singlet, OH at the 7 position); 4.98 (1H, doublet, H at the 13 position, J=10.3 Hz).

EXAMPLE 145

13-(2-o-Fluorophenylpropionyloxy)-25-ethylmilbemycin (Compound of formula (IIb) wherein: R$^1$=ethyl, Z=α-methyl-o-fluorobenzyl, Y=—OH).

Mass Spectrum (m/z): 708(M+), 694, 690, 580, 540, 523.

Nuclear Magnetic Resonance Spectrum (CDCl$_3$) δ ppm: 3.95 (1H, doublet, H at the 6 position, J=6.1 Hz); 4.29 (1H, doublet, H at the 5 position, J=6.1 Hz); 4.91 and 4.93 (1H, doublet, H at the 13 position, J=10.5 Hz).

EXAMPLE 146

13-(1-Phenylcyclohexylcarbonyloxy)-25-ethylmilbemycin (Compound of formula (IIb) wherein: R$^1$=ethyl, Z=α-cyclohexylbenzyl, Y=—OH).

Mass Spectrum (m/z): 758(M+), 740, 630, 540, 522.

Nuclear Magnetic Resonance Spectrum (CDCl$_3$) δ ppm: 3.95 (1H, doublet, H at the 6 position, J=6.4 Hz); 4.08 (1H, singlet, OH at the 7 position); 4.86 and 4.89 (1H, doublet, H at the 13 position, J=10.6 Hz).

EXAMPLE 147

13-(1-Phenylcyclopentylcarbonyloxy)-25-ethylmilbemycin (Compound of formula (IIb) wherein: R$^1$=ethyl, Z=1-phenylcyclopentyl, Y=—OH).

Mass Spectrum (m/z): 730(M+), 712, 602, 540, 522.

Nuclear Magnetic Resonance Spectrum (CDCl$_3$) δ ppm: 3.94 (1H, doublet, H at the 6 position, J=6.2 Hz); 4.07 (1H, singlet, OH at the 7 position); 4.80 (1H, doublet, H at the 13 position, J=10.6 Hz).

EXAMPLE 148

13-[2-(Phenylthio)propionyloxy]-25-ethylmilbemycin (Compound of formula (IIb) wherein: R$^1$=ethyl, Z=1-(phenylthio)ethyl, Y=—OH).

Mass Spectrum (m/z): 722(M+), 704, 594, 540, 522.

Nuclear Magnetic Resonance Spectrum (CDCl$_3$) δ ppm: 3.96 (1H, doublet, H at the 6 position, J=6.5 Hz); 4.04 (1H, broad singlet, OH at the 7 position); 4.93 (1H, doublet, H at the 13 position, J=10.5 Hz).

EXAMPLE 149

13-(1-Phenylcyclopropylcarbonyloxy)-25-ethylmilbemycin (Compound of formula (IIb) wherein: R$^1$=ethyl, Z=1-phenylcyclopropyl, Y=—OH).

Mass Spectrum (m/z): 702(M+), 684, 574, 540, 522, 504.

Nuclear Magnetic Resonance Spectrum (CDCl$_3$) δ ppm: 3.95 (1H, doublet, H at the 6 position, J=6.2 Hz); 4.02 (1H, singlet, OH at the 7 position); 4.87 (1H, doublet, H at the 13 position, J=10.6 Hz).

EXAMPLE 150

13-[2-o-Tolylpropionyloxy]-25-ethylmilbemycin (Compound of formula (IIb) wherein: R$^1$=ethyl, Z=α-methyl-o-methylbenzyl, Y=—OH).

Mass Spectrum (m/z): 704(M+), 690, 686, 646, 604, 576, 540, 522.

Nuclear Magnetic Resonance Spectrum (CDCl$_3$) δ ppm: 4.23 (1H, multiplet, H at the 5 position); 4.66 (2H, broad singlet, 2H at the 27 position); 4.89 (1H, doublet, H at the 13 position, J=10.6 Hz): 5.25–5.42 (4H, multiplet, H at the 3, 11, 15 and 19 position); 5.7–5.8 (2H, multiplet, H at the 9 and 10 position).

EXAMPLE 151

13-[2-(S)-Phenylpropionyloxy]-25-ethylmilbemycin (Compound of formula (IIb) wherein: R$^1$=ethyl, Z=(S)-α-methylbenzyl, Y=—OH).

Mass Spectrum (m/Z): 690(M+), 672, 632, 562, 540, 522.

Nuclear Magnetic Resonance Spectrum (CDCl$_3$) δ ppm: 3.94 (1H, doublet, H at the 6 position, J=6.0 Hz); 4.04 (1H, singlet, OH at the 7 position); 4.88 (1H, doublet, H at the 13 position, J=10.5 Hz).

EXAMPLE 152

13-[2-(R)-Phenylpropionyloxy]-25-ethylmilbemycin (Compound of formula (IIb) wherein: R$^1$=ethyl, Z=(R)-α-methylbenzyl, Y=—OH).

Mass Spectrum (m/z): 690(M+), 672, 632, 562, 540, 522.

Nuclear Magnetic Resonance Spectrum (CDCl$_3$) δ ppm: 3.95 (1H, doublet, H at the 6 position, J=6.0 Hz); 4.08 (1H, broad singlet, OH at the 7 position); 4.89 (1H, doublet, H at the 13 position, J=10.3 Hz).

EXAMPLE 153

13-(2-p-Aminophenylpropionyloxy)-25-ethylmilbemycin (Compound of formula (IIb) wherein: R$^1$=ethyl, Z=α-methyl-p-aminophenyl, Y=—OH).

A solution of 131.8 mg of 13-(2-methyl-2-p-nitrophenylpropionyloxy)-25-ethylmilbemycin in 8 ml of methanol was hydrogenated for 6 hours, with stirring, at room temperature in the presence of 3 mg of 5% palladium-on-charcoal. At the end of this time, the reaction mixture was filtered and the filtrate was concentrated under reduced pressure. The residue was purified by column chromatography through silica gel to give 65.0 mg (yield: 51.4%) of the title compound.

Mass Spectrum (m/z); 705(M+), 687, 671, 540, 522, 504.

Nuclear Magnetic Resonance Spectrum (CDCl$_3$) δ ppm: 3.98 (1H, doublet, H at the 6 position, J=6.1 Hz); 4.05 (1H, singlet, OH at the 7 position); 4.30 (1H, doublet, H at the 6 position J=6.1 Hz): 4.65–4.8 (2H, multiplet, 2H at the 27 position); 5.16 (1H, doublet, H at the 13 position, J=10.4 Hz); 5.3–5.5 (4H, multiplet); 5.8–5.95 (2H, multiplet); 6.66 (2H, doublet, J=8.5 Hz); 7.85 (2H, doublet, J=8.5 Hz).

EXAMPLE 154

13-[2-(2-Pyridon-1-yl)propionyloxy]-25-ethylmilbemycin (Compound of formula (IIb) wherein: $R^1$=ethyl, Z=1-(2-pyridon-1-yl)ethyl, Y=—OH).

Mass Spectrum (m/z): 707(M+), 689, 540, 522, 504, 460, 442, 412, 394.

Nuclear Magnetic Resonance Spectrum (CDCl$_3$) δ ppm: 3.96 (1H, doublet, H at the 6 position, J=6.0 Hz); 4.04 (1H, singlet, OH at the 7 position); 4.96 and 4.98 (1H, doublet, H at the 13 position, J=10.6 Hz).

EXAMPLE 155

13-[2-(2-Piperidon-1-yl)propionyloxy]-25-ethylmilbemycin (Compound of formula (IIb) wherein: $R^1$=ethyl, Z=1-(2-piperidon-1-yl)ethyl, Y=—OH).

Mass Spectrum (m/z): 540(M+-171), 522, 504, 412, 394, 195, 167, 154.

Nuclear Magnetic Resonance Spectrum (CDCl$_3$) δ ppm: 3.71 (1H, singlet, OH at the 7 position); 3.97 (1H, doublet, H at the 6 position, J=6.1 Hz); 4.93 and 4.96 (1H, doublet H at the 13 position. J=10.5 Hz).

EXAMPLE 156

13-[2-(2-Pyridyl)propionyloxy]-25-ethylmilbemycin (Compound of formula (IIb) wherein: $R^1$=ethyl, Z=1-(2-piridyl)ethyl, Y=—OH).

Mass Spectrum (m/Z): 691(M+), 673, 540, 522, 504.

Nuclear Magnetic Resonance Spectrum (CDCl$_3$) δ ppm: 3.70 (1H, singlet, OH at the 7 position); 3.92 (1H, doublet, H at the 6 position, J=6.5 Hz); 4.12 and 4.28 (1H, triplet, H at the 5 position, J=6.5 Hz); 4.62–4.73 (2H, multiplet, 2H at the 27 position).

EXAMPLE 157

13-(2-Phenylpropionyloxy)-23-hydroxy-25-(1,3-dimethyl-1-butenyl)milbemycin (Compound of formula (IIb) wherein: $R^1$=1,3-dimethyl-1-butenyl, Z=α-methylbenzyl, X=—OH, Y=—OH).

Mass Spectrum (m/z): 760(M+), 742, 725, 710, 331.

Nuclear Magnetic Resonance Spectrum (CDCl$_3$) δ ppm: 3.94 (1H, doublet, H at the 6 position, J=6.4 Hz); 4.28 (1H, triplet, H at the 5 position, J=6.4 Hz); 4.65 (2H, broad singlet, 2H at the 27 position); 4.88 (1H, doublet, H at the 13 position, J=10.5 Hz).

Examples 158 to 163 illustrate the preparation of compounds of formula (IIc) from starting materials of formula (IIb), by the reaction of Step C in Reaction Scheme No. 2 above.

EXAMPLE 158

13-(2-Methyl-2-phenylproyionyloxy)-5-O-propionyl-25-ethylmilbemycin (Compound of formula (IIc) wherein: $R^1$=ethyl, Z=α,α-dimethylbenzyl, Y=propionyloxy).

51 μl of propionyl chloride and 38 μl of pyridine were added, under ice-cooling, to a solution of 91 mg of 13-(2-methyl-2-phenylpropionyloxy)-25-ethylmilbemycin in methylene chloride, and then the mixture was stirred at room temperature for 3 hours. At the end of this time, the reaction mixture was poured into water and extracted with ethyl acetate. The extract was washed, in turn, with water and a saturated aqueous solution of sodium chloride, dried over magnesium sulfate and concentrated by evaporation. The residue was purified by column chromatography through silica gel to give 75 mg (yield: 76%) of the title compound.

Mass Spectrum (M/z): 760(M+), 686, 596, 540, 522, 504.

Nuclear Magnetic Resonance Spectrum (CDCl$_3$) δ ppm: 3.99 (1H, broad singlet, OH at the 7 position); 4.04 (1H, doublet, H at the 6 position, J=5.9 Hz); 4.53 (1H, doublet, H at the 27 position, J=14.3 Hz); 4.62 (1H, doublet, H at the 27 position, J=14.3 Hz); 4.87 (1H, doublet, H at the 13 position, J=10.3 Hz); 5.25–5.45 (3H, multiplet); 5.5–5.6 (2H, multiplet); 5.65–5.8 (4H, multiplet); 7.2–7.4 (5H, multiplet).

EXAMPLE 159

5O-(3-Carboxypropionyl)-13-(2-methyl-2-phenylpropionyloxy)-25-ethylmilbemycin (Compound of formula (IIc) wherein: $R^1$=ethyl, Z=α,α-dimethylbenzyl, Y=3-carboxypropionyloxy).

Following the procedure of Example 158, but using 76 mg of 13-(2-methyl-2-phenylpropionyloxy)-25-ethylmilbemycin and 100 mg of succinic acid anhydride, there were obtained 61 mg (yield: 70%) of the title compound.

Mass Spectrum (m/z): 804(M+), 704, 686, 668.

Nuclear Magnetic Resonance Spectrum (CDCl$_3$) δ ppm: 4.03 (1H, doublet, H at the 6 position, J=5.9 Hz); 4.53 (1H, doublet, H at the 27 position, J=14.2 Hz); 4.62 (1H, doublet, H at the 27 position, J=14.2 Hz); 4.87 (1H, doublet H at the 13 position, J=10.3 Hz); 5.35–5.5 (3H, multiplet); 5.5–5.6 (2H, multiplet); 5.65–5.8 (2H, multiplet); 7.3 (5H, multiplet).

The compounds of Examples 160 to 162 were also prepared by following the procedure of Example 158.

EXAMPLE 160

13-(2-o-Chlorophenylpropionyloxv)-5-O-chloroacetyl-25-ethylmilbemycin (Compound of formula (IIc) wherein: $R^1$=ethyl, Z=α-methyl-o-chlorobenzyl, Y=chloroacetoxy.

Mass Spectrum (m/z): 800(M+), 782, 616, 522.

Nuclear Magnetic Resonance Spectrum (CDCl$_3$) δ ppm: 4.57 (1H, doublet, H at the 27 position, J=15.1 Hz); 4.62 (1H, doublet, H at the 27 position, J=15.1 Hz); 4.92 (1H, doublet, H at the 13 position, J=10.6 Hz); 5.27–5.41 (3H, multipler, H at the 11, 15 and 19 position); 5.56 (1H, multiplet, H at the 3 position); 5.72–5.82 (2H, multiplet, H at the 9 and 10 position.

EXAMPLE 161

13-(2-o-Chlorophenylpropionyloxy)-5-O-ethoxycarbonyl-25-ethylmilbemycin (Compound of formula (IIc) wherein: $R^1$=ethyl, Z=α-methyl-o-chlorobenzyl, Y=ethoxycarbonyloxy.

Mass Spectrum (m/z): 796($M^+$-18), 738, 688, 612, 522, 504.

Nuclear Magnetic Resonance Spectrum ($CDCl_3$) δ ppm: 4.06 (1H, broad singlet, OH at the 7 position); 4.10 (1H, doublet, H at the 6 position, J=6.2 Hz); 4.90 and 4.91 (1H, doublet, H at the 13 position, J=10.6 Hz).

EXAMPLE 162

13-(2-Methyl-2-phenylpropionyloxy)-5-O-chloroacetyl-25-ethylmilbemycin (Compound of formula (IIc) wherein: $R^1$=ethyl, Z=α,α-dimethylbenzyl, Y=chloroacetoxy.

Mass Spectrum (m/z): 780($M^+$), 616, 597, 522.

Nuclear Magnetic Resonance Spectrum ($CDCl_3$) δ ppm: 4.03 (1H, singlet, OH at the 7 position); 4.08 (1H, doublet, H at the 6 position, J=6.5 Hz); 4.87 (1H, doublet, H at the 13 position, J=10.5 Hz).

EXAMPLE 163

13-(2-Methyl-2-phenylpropionyloxy)-5-O-acetoxyacetyl-25-ethylmilbemycin (Compound of formula (IIc) wherein: $R^1$=ethyl, Z=α,α-dimethylbenzyl, Y=acetoxyacetoxy.

123 mg of sodium iodide were added to a solution of 129 mg of 13-(2-methyl-2-phenylpropionyloxy)-5-O-chloroacetyl-25-ethylmilbemycin in methylene chloride, and the mixture was stirred at room temperature for 4 hours. At the end of this time, the reaction mixture was poured into water and then extracted with ethyl acetate. The extract was washed, in turn, with water and a saturated aqueous solution of sodium chloride, dried over magnesium sulfate and concentrated to give a crude 13-(2-methyl-2-phenylpropionyloxy)-5-O-iodoacetyl-25-ethylmilbemycin.

This crude product was dissolved in 15 ml of N,N-dimethylacetamide, 135 mg of sodium acetate were added, and the mixture was stirred at room temperature for 3 hours. At the end of this time, the reaction mixture was poured into water and extracted with ethyl acetate. The extract was washed, in turn, with water and a saturated aqueous solution of sodium chloride and then concentrated. The residue was purified by preparative thin layer chromatography (Merck Art 5717, 20×20 cm, thickness 2 mm), developed with a 1:1 by volume mixture of hexane and ethyl acetate, to give 93.8 mg (yield: 70.6%) of the title compound.

Mass Spectrum (m/z): 804($M^+$), 640, 622, 540, 522, 504.

Nuclear Magnetic Resonance Spectrum ($CDCl_3$) δ ppm: 4.03 (1H, singlet, OH at the 7 position); 4.05 (1H, doublet, H at the 6 position, J=6.1 Hz); 4.5–4.7 (4H, multiplet); 4.87 (1H, doublet, H at the 13 position, J=10.4 Hz); 5.25–5.4 (2H, multiplet); 5.5–5.6 (2H, multiplet); 5.7–5.8 (2H, multiplet); 7.2–7.35 (5H, multiplet).

Preparations 1 to 4 illustrate the synthesis of starting materials for use in preparing the compounds of the invention by the reactions described above.

PREPARATION 1

13-p-Fluorophenoxyacetoxy-5-keto-25-ethylmilbemycin (Compound of formula (III) wherein: $R^1$=ethyl, $R^2$=p-fluorophenoxymethyl, n=0).

23 mg of 1,3-dicyclohexylcarbodiimide, 62 mg of 13-hydroxy-5-keto-25-ethylmilbemycin and a trace of 4-pyrrolidinopyridine were added successively to a solution of 17 mg of p-fluorophenoxyacetic acid in 15 ml of methylene chloride, and the resulting mixture was then stirred for 30 minutes at room temperature. After completion of the reaction, the mixture was filtered and the filtrate was poured into water, followed by extraction with ethyl acetate. The ethyl acetate extracts were washed with saturated aqueous sodium chloride solution and dried over magnesium sulfate. The solvent was distilled off from the extract, and the residue was subjected to column chromatography over silica gel, giving 44 mg of the desired compound.

Mass Spectrum (m/z): 708($M^+$).

Nuclear Magnetic Resonance Spectrum (270 MHz, $CDCl_3$) δ ppm: 3.86 (1H, singlet, OH at the 7 position); 4.01 (1H, singlet, H at the 6 position); 5.06 (1H, doublet, H at the 13 position, J=10.3 Hz).

PREPARATION 2

5-Keto-23-hydroxy-25-(1,3-dimethyl-1-butenyl)milbemycin 0.64 g of activated manganese dioxide was added to a solution of 61.2 mg of 23-hydroxy-25-(1,3-dimethyl-1-butenyl)milbemycin in 5 ml of acetone, and the resulting mixture was stirred vigorously for 30 minutes. The mixture was then filtered over "Celite" filter aid, and the filtrate was concentrated, giving 59.3 mg of the crude desired compound.

Mass Spectrum (m/z): 610, 592, 574.

Nuclear Magnetic Resonance Spectrum ($CDCl_3$) δ ppm: 3.78 (1H, singlet, OH at the 7 position); 3.84 (1H, singlet, H at the 6 position).

PREPARATION 3

13,23-Dihydroxy-5-keto-25-(1,3-dimethyl-1-butenyl)-milbemycin

The crude 5-keto-23-hydroxy-25-(1,3-dimethyl-1-butenyl)milbemycin, obtained in Preparation 2 above, was dissolved in 3 ml of formic acid, then 13 mg of selenium dioxide were added to the solution, and the resulting mixture was stirred for 1.5 hours at room temperature. The mixture was then filtered over "Celite" filter aid, and the filtrate was poured into water and then extracted with ethyl acetate. The extract was dried over magnesium sulfate and concentrated. The residue was dissolved in a mixture of 2 ml of methanol, 3 ml of dioxane and 1 ml of 2N hydrochloric acid. The solution was kept stirred overnight at room temperature, then poured into water and extracted with ethyl acetate. The extract was dried over magnesium sulfate and concentrated. The residue was purified by preparative thin layer chromatography (Merck, Art 5715, 20×20 cm, 2 mm thick), developed with a 1:1 by volume mixture of hexane and ethyl acetate, to give 13.2 mg of the desired compound (yield: 21.7%).

Mass Spectrum (m/z): 626($M^+$-36), 608, 590, 349, 331, 259, 242, 179.

Nuclear Magnetic Resonance Spectrum (CDCl$_3$+D$_2$O) δ ppm: 3.73 (1H, doublet, H at the 13 position, J=9.7 Hz); 3.75 (1H, doublet, H at the 25 position, J=10.5 Hz); 3.84 (1H, singlet, H at the 6 position).

PREPARATION 4

13-(2-Methyl-2-phenylpropionyloxy)-5-keto-25-ethylmilbemycin 1.6 g of 2-methyl-2-phenylpropionyl chloride and 0.73 ml of pyridine were added, in turn to a solution of 557 mg of 13-hydroxy-5-keto-25-ethylmilbemycin in 20 ml of chloroform, and then the mixture was stirred at 60° C. for 3 hours. At the end of this period, the reaction mixture was poured into water and extracted with ethyl acetate. The extract was washed, in turn, with an aqueous solution of sodium bicarbonate, water and a saturated aqueous solution of sodium chloride, dried over magnesium sulfate and concentrated by evaporation. The residue was purified by column chromatography through silica gel to give 353 mg (yield: 50%) of the title compound.

Mass Spectrum (m/z): 702(M+), 684, 538, 520.

Nuclear Magnetic Resonance Spectrum (CDCl$_3$) δ ppm: 3.84 (1H, singlet, H at the 6 position); 4.01 (1H, singlet, OH at the 7 position); 4.80 (2H, multiplet, H at the 27 position); 4.87 (1H, doublet, H at the 13 position, J=10.3 Hz); 5.3-5.5 (3H, multiplet, H at the 11, 15 and 19 position); 5.7-5.9 (2H, multiplet, H at the 9 and 10 position); 6.53 (1H, multiplet, H at the 3 position); 7.3 (5H, multiplet).

EXAMPLE 164

Acaricidal activity against Tetranychus urticae

The primary leaves of cowpea plants of the species *Vigna sinensis* Savi were infected with organic phosphate-sensitive mites (*Tetranychus urticae*). One day after infection, the infested plants were sprayed, using a Mizuho rotary sprayer, with 7 ml of a test solution containing the compound under test at a concentration of 3 ppm, at a rate of 3.5 mg of the test solution per 1 cm$^2$ of leaf. The plants were assessed after 3 days by examining adult mites, under a binocular microscope, to determine living and dead individuals. Two plants were used for each concentration and each test compound. The plants were kept during the test in greenhouse compartments at 25° C. The results are reported in the following Table.

| Compound of Example No. | Mortality (%) |
|---|---|
| 2 | 99 |
| 10 | 93 |
| 11 | 97 |
| 12 | 100 |
| 13 | 94 |
| 17 | 93 |
| 18 | 100 |
| 19 | 97 |
| 41 | 93 |
| 44 | 92 |
| 62 | 100 |
| 66 | 96 |
| 68 | 90 |
| 71 | 100 |
| 72 | 100 |
| 73 | 100 |
| 74 | 100 |
| 76 | 100 |
| 78 | 100 |
| 79 | 95 |
| 80 | 100 |
| 82 | 100 |
| 83 | 100 |
| 84 | 93 |
| 86 | 98 |
| 87 | 100 |
| 88 | 97 |
| 89 | 97 |
| 90 | 100 |
| 91 | 100 |
| 98 | 94 |
| 101 | 91 |
| 102 | 97 |
| 103 | 100 |
| 104 | 94 |
| 105 | 100 |
| 106 | 96 |
| 109 | 100 |
| 110 | 100 |
| 112 | 92 |
| 114 | 100 |
| 115 | 100 |
| 116 | 98 |
| Control Compound 1 | 40 |
| Control Compound 2 | 3 |
| Control Compound 3 | 12 |
| Control Compound 4 | 45 |

The Control Compounds were as follows:
1. 25-Ethylmilbemycin (milbemycin A$_4$).
2. 5-Keto-25-ethylmilbemycin 5-oxime.
3. 5-Keto-25-ethylmilbemycin 5-O-dimethylcarbamoyloxime.
4. 5-Keto-25-ethylmilbemycin 5-O-pivaloyloxime.

As can be seen clearly from the above results, the compounds of the present invention have a far stronger acaricidal activity than that of Control Compound No. 1 (i.e. the naturally produced milbemycin A$_4$), and also of the other milbemycin derivatives unsubstituted at the 13-position used as Control Compounds 2, 3 and 4.

EXAMPLE 165

Acaricidal activity against Tetranychus urticae

The procedures of Example 164 were repeated with a different set of test compounds, except that the concentration of the compound in the test solution was 0.3 ppm. The results obtained are shown in the following table.

| Compound of Example No. | Mortality (%) |
|---|---|
| 129 | 100 |
| 130 | 95 |
| 131 | 95 |
| 132 | 100 |
| 133 | 95 |
| 134 | 100 |
| 135 | 70 |
| 136 | 100 |
| 137 | 70 |
| 139 | 70 |
| 140 | 85 |
| 141 | 100 |
| 142 | 100 |
| 145 | 95 |
| 158 | 80 |
| Control Compound 1 | 20 |
| Control Compound 5 | 45 |
| Control Compound 6 | 45 |

| Compound of Example No. | Mortality (%) |
|---|---|
| Control Compound 7 | 30 |

The Control Compounds were as follows:
1. 25-Ethylmilbemycin (milbemycin A₄).
5. 13-Benzoyloxy-25-ethylmilbemycin.
6. 13-Pivaloyloxy-25-ethylmilbemycin.
7. 13-Phenylacetoxy-25-ethylmilbemycin.

These results clearly demonstrate the markedly superior acaricidal activity of the compounds of the invention, as compared with Control Compound No. 1 (i.e. the naturally produced milbemycin A₄), and also as compared with the 13-substituted derivatives used as Control Compounds 5, 6 and 7.

EXAMPLE 166

Acaricidal activity against *Boophilus microplus*

Groups of 10 engorged female ticks of the species *Boophilus microplus* were immobilized on polyvinyl chloride panels by means of double-sided adhesive tape. The test compounds were administered to each group at varying dosages ranging from 0.0005 μg to 5 μg, dissolved in 2 or 1 μl of solvent, in order to determine their IR₉₀ value—i.e. the concentration of the test compound which would result in 90% inhibition of reproduction by division, 3 days after treatment.

The compounds of Examples 2, 3, 6, 7, 9, 10, 11, 18 and 19 were found to exhibit an IR₉₀ value of 0.5 μg/group.

EXAMPLE 167

Activity against *Dermanyssus gallinae*

Compounds of the invention were tested for activity against mites of the species *Dermanyssus gallinae*. Groups consisting of 100–200 mites, at various stages of growth, were transferred into test tubes containing 2–3 ml of a solution of the test compound at a concentration of 100 ppm. The test tubes were stoppered with cotton wool and shaken for 10 minutes, then the solution was sucked out through the cotton wool and the tubes with the treated mites allowed to stand for 3 days at room temperature.

The compounds of Examples 6–13, 15, 17–20, 22–25, 27, 31–36, 38, 39, 43–47, 51–53, 56, 57, 64, 65, 67, 68, 74, 75, 77–79, 81, 82, 84, 87–89, 91, 98, 102–106, 109–119, 124, 127, 129–131, 134–137, 140–142, 146–151, 158 and 159 were tested in this way and each produced 100% mortality in the test groups.

EXAMPLE 168

Activity against *Lucilia sericata*

Groups consisting of 30–50 eggs from the species *Lucilia sericata*, collected immediately after oviposition, were added to test tubes each containing 1 ml of a liquid culture medium and 1 ml of the test compound in solution at a concentration of 100 ppm. The test tubes were stoppered with cotton wool and allowed to stand for 4 days at 30° C. The percentage mortality in each test group was assessed at the end of the 4 days.

The compounds of Examples 6, 7, 9, 13, 17, 19, 20, 23–29, 31–36, 38, 41, 43–45, 47, 51–53, 56–58, 62, 65, 66, 68–70, 73 74, 76–79, 81–84, 87–91, 96, 101, 105, 108, 111–114, 116, 124, 127, 129–137, 140–143, 146, 147, 149–151 and 158–161 were tested in this way and each produced 100% mortality in the test groups.

We claim:
1. Compounds having the formula

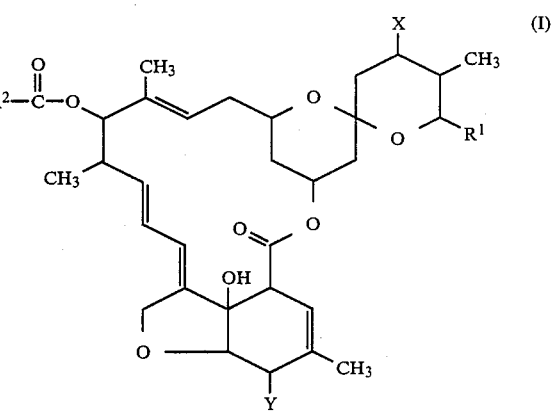

in which:
the broken line represents a carbon-carbon single or double bond between the atoms at the 22 and 23 positions;

X represents
a hydrogen atom or a hydroxyl group, or together with the carbon atom to which it is attached represents the group C=O; provided that X represents a hydrogen atom when the broken line represents a double bond between the carbon atoms at the 22 and 23 positions;

Y represents
the group =N—OR³,
wherein R³ represents a hydrogen atom, an alkyl group having from 1 to 6 carbon atoms and which may optionally be substituted with at least one carboxy group, a cycloalkyl group having from 3 to 10 ring carbon atoms, or an aralkyl group having from 6 to 10 ring carbon atoms in the aryl moiety and from 1 to 6 carbon atoms in the alkyl moiety;

R¹ represents
an alkyl, alkenyl, alkynyl, alkoxyalkyl or alkylthioalkyl group, each having up to 8 carbon atoms;
a cycloalkyl-substituted alkyl group wherein the cycloalkyl moiety has from 3 to 6 ring carbon atoms and the alkyl moiety has from 1 to 5 carbon atoms:
a cycloalkyl or cycloalkenyl group having from 3 to 8 ring carbon atoms and optionally substituted with at least one substituent selected from halogen atoms and alkyl groups having from 1 to 4 carbon atoms;
a heterocyclic group having from 3 to 6 ring atoms of which at least one is an oxygen or sulfur atom and which may optionally be substituted with at least one substituent selected from halogen atoms and alkyl groups having from 1 to 4 carbon atoms;

R² represents
the group R⁵—(O)ₙ—
wherein n=0 or 1;
R⁵ represents a hydrogen atom, an alkyl group having from 1 to 22 carbon atoms, an alkenyl or alkynyl group having from 2 to 6 carbon atoms, a cycloalkyl group having from 3 to 10 carbon atoms, an aryl group having from 6 to 10 ring carbon atoms, an aralkyl group having from 6 to 10 ring carbon atoms in the aryl moiety and from 1 to 6 carbon atoms in the alkyl moiety, wherein said alkyl group of $R^5$ may optionally be substituted with at least one substituent selected from:

(a) cycloalkyl groups having from 3 to 10 carbon atoms; alkoxy groups having from 1 to 6 carbon atoms; alkoxycarbonyl groups having from 2 to 7 carbon atoms; halogen atoms; aryloxy and arylthio groups having from 6 to 10 ring carbon toms, which may themselves optionally be substituted with at least one halogen atom; protected or unprotected hydroxy; carboxy; amino; monoalkylamino and dialkylamino groups having from 1 to 6 carbon atoms in the or each alkyl moiety; aliphatic acylamino groups having from 1 to 6 carbon atoms; aromatic acylamino groups; cyano; carbamoyl; monoalkylcarbamoyl and dialkylcarbamoyl groups having from 1 to 6 carbon atoms in the or each alkyl moiety; mercapto; alkylthio, alkylsulfinyl and alkylsulfonyl groups, in each case having from 1 to 6 carbon atoms; nitro;

and wherein said alkenyl and alkynyl groups of $R^5$ may optionally be substituted with at least one substituent selected from the group consisting of:

(b) the said substituent (a); and acyl groups having from 6 to 10 ring carbon atoms; and the said cycloalkyl, aryl, aralkyl;

and salts and esters of said compounds of formula (I).

2. Compounds as claimed in claim 2, wherein $R^3$ represents a hydrogen atom.

3. Compounds as claimed in claim 1, wherein $R^1$ represents a methyl, ethyl, isopropyl, sec-butyl, 1-methyl-1-propenyl, 1-methyl-1-butenyl or 1,3-dimethyl-1-butenyl group.

4. Compounds as claimed in claim 1, wherein $R^1$ represents a methyl, ethyl, isopropyl or sec-butyl group, X represents a hydrogen atom, and there is a carbon-carbon single bond between the atoms at the 22 and 23 positions.

5. Compounds as claimed in claim 1, wherein $R^5$ represents an alkyl or haloalkyl group having from 4 to 7 carbon atoms, phenyl, benzyl or a phenyl or benzyl group substituted with one or two substituents selected from trifluoromethyl, halogen, methyl and amino.

6. Compounds according to claim 1, wherein $R^2$ represents a t-butyl, fluoro-t-butyl, 2,6-difluorophenyl or o-(trifluoromethyl)phenyl group.

7. An anthelmintic acaricidal and insecticidal composition, which comprises an effective amount of a compound as claimed in claim 1 in admixture with a pharmaceutically, agriculturally, veterinarily or horticulturally acceptable carrier or diluent.

8. A method of protecting animals or plants from damage by parasites selected from acarids, helminths and insects, which comprises applying to said animals or plants, or to said seeds of said plants or to a locus including said animals, plants or seeds, and effective amount of a compound as claimed in claim 1.

9. A compound selected from the group consisting of:
13-pivaloyloxy-5-keto-25-ethylmilbemycin 5-oxime,
13-(2,2-dimethyl-1,3-dioxolanyl)methoxycarbonyloxy-5-keto-25-ethylmilbemycin-5-oxime,
13-o-trifluoromethylbenzoyloxy-5-keto-25-ethylmilbemycin-5-oxime
13-(2-furoyloxy)-5-keto-25-ethylmilbemycin 5-oxime,
13-(3-chloro-2,2-dimethylpropionyloxy)-5-keto-25-ethylmilbemycin 5-oxime,
13-(3-fluoro-2,2-dimethylpropionyloxy)-5-keto-25-ethylmilbemycin 5-oxime,
13-(2,6-difluorobenzoyloxy)-5-keto-25-ethylmilbemycin 5-oxime,
13-(2-phenylpropionyloxy)-5-keto-25-ethylmilbemycin 5-oxime,
13-(2-methyl-2-phenylpropionyloxy)-5-keto-25-ethylmilbemycin 5-oxime,
13-(2-p-aminophenylpropionyloxy)-5-keto-25-ethylmilbemycin 5-oxime, and
13-(2-phenylbutyryloxy)-5-keto-25-ethylmilbemycin 5-oxime.

10. The compound as claimed in claim 9 selected from the group consisting of:
13-pivaloyloxy-5-keto-25-ethylmilbemycin 5-oxime,
13-(2,2-dimethyl-1,3-dioxolanyl)methoxycarbonyloxy-5-keto-25-ethylmilbemycin 5-oxime,
13-(2-furoyloxy-5-keto-25-ethylmilbemycin 5-oxime,
13-(3-chloro-2,2-dimethylpropionyloxy)-5-keto-25-ethylmilbemycin 5-oxime,
13-(3-fluoro-2,2-dimethylpropionyloxy)-5-keto-25-ethylmilbemycin 5-oxime,
13-(2-phenylpropionyloxy)-5-keto-25-ethylmilbemycin 5-oxime,
13-(2-methyl-2-phenylpropionyloxy)-5-keto-25-ethylmilbemycin 5-oxime,
13-(2-p-aminophenylpropionyloxy)-5-keto-25-ethylmilbemycin 5-oxime, and
13-(2-phenylbutyryloxy)-5-keto-25-ethylmilbemycin 5-oxime.

11. The compound as claimed in claim 9, selected from the group consisting of:
13-(2,6-difluorobenzoyloxy)-5-keto-25-ethylmilbemycin and 5-oxime, and
13-o-trifluoromethylbenzoyloxy-5-keto-25-ethylmilbemycin 5-oxime.

12. The compound as claimed in claim 9, selected from the group consisting of:
13-(2,6-difluorobenzoyloxy)-5-keto-25-ethylmilbemycin 5-oxime.

* * * * *

UNITED STATES PATENT AND TRADEMARK OFFICE
CERTIFICATE OF CORRECTION

PATENT NO. : 4,963,582

DATED : October 16, 1990

INVENTOR(S) : SATO et al

It is certified that error appears in the above-identified patent and that said Letters Patent is hereby corrected as shown below:

```
Column 73, line 31 (claim 1), change "acyl" to --aryl--.

Column 73, line 33 (claim 1), change "aryl, aralkyl" to
     --aryl and aralkyl--.

Column 73, line 36 (claim 2), change "claim 2" to
     --claim 1--.

Column 73, line 55 (claim 6), change "o-(trifluoro..." to
     --o-(trifluoro...--.

Column 74, line 13 (claim 9), change "13-o-trifluoro..."
     to --13-o-trifluoro...--.

Column 74, line 26 (claim 9), change "13-(2-p-amino..."
     to --13-(2-p-amino...--.
```

UNITED STATES PATENT AND TRADEMARK OFFICE
CERTIFICATE OF CORRECTION

PATENT NO. : 4,963,582

DATED : October 16, 1990

INVENTOR(S) : SATO et al

It is certified that error appears in the above-identified patent and that said Letters Patent is hereby corrected as shown below:

```
Column 74, line 44 (claim 10), change "13-(2-p-amino..."
     to --13-(2-p-amino...--.

Column 74, line 52 (claim 11), change "13-o-trifluoro..."
     to --13-o-trifluoro...--.
```

Signed and Sealed this

Twentieth Day of October, 1992

Attest:

DOUGLAS B. COMER

*Attesting Officer*     *Acting Commissioner of Patents and Trademarks*